US007816556B2

(12) United States Patent
Wonders et al.

(10) Patent No.: US 7,816,556 B2
(45) Date of Patent: *Oct. 19, 2010

(54) POLYCARBOXYLIC ACID PRODUCTION SYSTEM EMPLOYING ENHANCED MULTISTAGE OXIDATIVE DIGESTION

(75) Inventors: Alan George Wonders, Kingsport, TN (US); Ronald Buford Sheppard, Kingsport, TN (US); Thomas Earl Woodruff, Kingsport, TN (US); Martin De Boer, Barendrecht (NL); Raymond Elbert Fogle, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 1021 days.

This patent is subject to a terminal disclaimer.

(21) Appl. No.: 11/365,248

(22) Filed: Mar. 1, 2006

(65) Prior Publication Data
US 2007/0208191 A1    Sep. 6, 2007

(51) Int. Cl.
*C07C 51/16* (2006.01)
(52) U.S. Cl. ..................... 562/412; 562/409
(58) Field of Classification Search .............. None
See application file for complete search history.

(56) References Cited
U.S. PATENT DOCUMENTS

| | | | |
|---|---|---|---|
| 2,694,622 A | 11/1954 | Reed et al. | |
| 3,057,909 A | 10/1962 | Sebelist et al. | |
| 3,064,044 A | 11/1962 | Baldwin | |
| 3,452,088 A | 6/1969 | Olsen et al. | |
| 3,584,039 A | 6/1971 | Meyer | |
| 3,626,001 A | 12/1971 | Keith et al. | |
| 3,629,321 A | 12/1971 | Longland, Jr. | |
| 3,850,983 A | 11/1974 | Park | |
| 3,899,485 A | 8/1975 | Immel et al. | |
| 3,931,305 A | 1/1976 | Fisher | |
| 3,996,271 A | 12/1976 | Yokota et al. | |
| 4,158,738 A | 6/1979 | Scott et al. | |
| 4,356,319 A | 10/1982 | Roffia et al. | |
| 4,500,732 A | 2/1985 | Petty-Weeks et al. | |
| 4,594,449 A | 6/1986 | Takuma et al. | |
| 4,719,247 A | 1/1988 | Lin et al. | |
| 4,772,748 A | 9/1988 | Hashizume et al. | |
| 4,892,970 A | 1/1990 | Nowicki et al. | |

(Continued)

FOREIGN PATENT DOCUMENTS

DE    27 33 917 A1    2/1978

(Continued)

OTHER PUBLICATIONS

USPTO Notice of Allowance dated Jan. 3, 2008 for copending U.S. Appl. No. 11/366,004.

(Continued)

*Primary Examiner*—Karl J Puttlitz
(74) *Attorney, Agent, or Firm*—Steven A. Owen; Bernard J. Graves, Jr.

(57) ABSTRACT

Disclosed is an optimized system for more efficiently and economically producing terephthalic acid. The system includes a multi-stage oxidative digestion system for processing an improved initial slurry from primary oxidation. The multi-stage digestion system is capable of adequately purifying the improved initial slurry without requiring significant liquor exchange between primary oxidation and oxidative digestion.

36 Claims, 23 Drawing Sheets

U.S. PATENT DOCUMENTS

| | | | |
|---|---|---|---|
| 4,898,717 A | 2/1990 | Hsia et al. | |
| 4,939,297 A | 7/1990 | Browder et al. | |
| 5,095,145 A | 3/1992 | Rosen | |
| 5,095,146 A | 3/1992 | Zeitlin et al. | |
| 5,171,548 A | 12/1992 | Rossiter et al. | |
| 5,175,355 A | 12/1992 | Streich et al. | |
| 5,260,239 A | 11/1993 | Hsia | |
| 5,359,133 A | 10/1994 | Nazimok et al. | |
| 5,510,521 A | 4/1996 | McGehee et al. | |
| 5,540,847 A | 7/1996 | Stultz et al. | |
| 5,567,842 A | 10/1996 | Izumisawa et al. | |
| 5,583,254 A | 12/1996 | Turner et al. | |
| 5,756,833 A | 5/1998 | Rosen et al. | |
| 5,763,648 A | 6/1998 | Hashizume et al. | |
| 5,770,629 A | 6/1998 | Degeorge et al. | |
| 5,821,270 A | 10/1998 | Chang et al. | |
| 5,958,986 A | 9/1999 | Mart et al. | |
| 5,994,567 A | 11/1999 | Kingsley et al. | |
| 6,080,372 A | 6/2000 | Machado | |
| 6,137,001 A | 10/2000 | Broeker et al. | |
| 6,201,030 B1 | 3/2001 | Beer | |
| 6,297,348 B1 | 10/2001 | Rodden et al. | |
| 6,355,835 B1 | 3/2002 | Kulsrestha et al. | |
| 6,392,091 B2 | 5/2002 | Lin | |
| 6,436,720 B1 | 8/2002 | Oberbeck et al. | |
| 6,504,051 B1 | 1/2003 | Miller, Jr. et al. | |
| 6,562,997 B2 | 5/2003 | Sikkenga et al. | |
| 6,689,903 B2 | 2/2004 | O'Meadhra et al. | |
| 6,765,113 B2 | 7/2004 | Graham et al. | |
| 6,800,664 B1 | 10/2004 | Espinoza et al. | |
| 6,846,848 B2 | 1/2005 | Wittenbrink et al. | |
| 6,949,673 B2 | 9/2005 | Housley et al. | |
| 7,132,566 B2 * | 11/2006 | Sumner et al. | 562/486 |
| 2002/0092584 A1 | 7/2002 | Soininen et al. | |
| 2002/0127167 A1 | 9/2002 | Satchell et al. | |
| 2002/0183546 A1 | 12/2002 | Sheppard et al. | |
| 2002/0193630 A1 | 12/2002 | Lin et al. | |
| 2003/0229247 A1 | 12/2003 | Housley et al. | |
| 2003/0229248 A1 | 12/2003 | Housley et al. | |
| 2004/0087814 A1 | 5/2004 | Gnagnetti et al. | |
| 2004/0110980 A1 * | 6/2004 | Sheppard et al. | 562/413 |
| 2004/0110981 A1 | 6/2004 | Sheppard et al. | |
| 2004/0215036 A1 | 10/2004 | Lin et al. | |
| 2004/0234435 A1 | 11/2004 | Bickham et al. | |
| 2004/0244536 A1 | 12/2004 | Lin | |
| 2004/0245176 A1 | 12/2004 | Parker et al. | |
| 2004/0260052 A1 | 12/2004 | Nagao et al. | |
| 2005/0038288 A1 | 2/2005 | Lin et al. | |
| 2005/0065373 A1 | 3/2005 | Sumner, Jr. et al. | |
| 2005/0084432 A1 | 4/2005 | Lin et al. | |
| 2005/0107630 A1 | 5/2005 | Belmonte et al. | |
| 2005/0159616 A1 | 7/2005 | Parker et al. | |
| 2005/0240055 A1 | 10/2005 | Lavoie | |
| 2005/0283022 A1 | 12/2005 | Sheppard | |
| 2006/0014979 A1 | 1/2006 | Numata et al. | |
| 2006/0047142 A1 | 3/2006 | Wonders et al. | |
| 2006/0047143 A1 | 3/2006 | Wonders et al. | |
| 2006/0047144 A1 | 3/2006 | Wonders et al. | |
| 2006/0047146 A1 | 3/2006 | Wonders et al. | |
| 2006/0047147 A1 | 3/2006 | Wonders et al. | |
| 2006/0047151 A1 | 3/2006 | Wonders et al. | |
| 2006/0047159 A1 | 3/2006 | Wonders et al. | |
| 2006/0047160 A1 | 3/2006 | Wonders et al. | |
| 2006/0047161 A1 | 3/2006 | Wonders et al. | |
| 2006/0047163 A1 | 3/2006 | de Vreede et al. | |
| 2006/0047166 A1 | 3/2006 | Lin et al. | |
| 2006/0205976 A1 | 9/2006 | Wonders et al. | |
| 2006/0205977 A1 | 9/2006 | Sumner et al. | |

FOREIGN PATENT DOCUMENTS

| | | |
|---|---|---|
| EP | 121 438 A1 | 10/1984 |
| EP | 0111784 B1 | 2/1986 |
| EP | 1188476 A2 | 3/2002 |
| GB | 983677 A | 2/1965 |
| GB | 1152575 | 5/1969 |
| GB | 1237298 | 6/1971 |
| GB | 1309451 | 3/1973 |
| GB | 1358520 A | 7/1974 |
| GB | 1373230 | 11/1974 |
| GB | 1454478 A | 11/1976 |
| GB | 2 032 920 A | 5/1980 |
| GB | 1589310 | 5/1981 |
| GB | 2204581 A | 11/1988 |
| GB | 2310210 A | 8/1997 |
| JP | 52-004277 | 2/1977 |
| JP | 54-025292 | 2/1979 |
| JP | 57 188543 A | 11/1982 |
| JP | 11343264 A | 11/1990 |
| JP | 5-015788 | 1/1993 |
| JP | 9-157214 | 6/1997 |
| JP | 2001/247511 | 9/2001 |
| JP | 2001247511 A | 9/2001 |
| JP | 2001/288139 | 10/2001 |
| JP | 2004/168716 | 6/2004 |
| WO | WO 98/08605 A1 | 3/1998 |
| WO | WO 99/31038 A1 | 6/1999 |
| WO | 2004/052820 A1 | 6/2004 |
| WO | WO 2005/049873 A1 | 6/2005 |
| WO | WO 2005/075403 A1 | 8/2005 |

OTHER PUBLICATIONS

USPTO Notice of Allowance dated Dec. 31, 2008 for copending U.S. Appl. No. 11/365,176.
USPTO Office Action dated Jan. 11, 2008 for copending U.S. Appl. No. 11/366,005.
USPTO Office Action dated Jan. 18, 2008 for copending U.S. Appl. No. 11/365,176.
USPTO Office Action dated Jan. 23, 2008 for copending U.S. Appl. No. 11/365,258.
USPTO Office Action dated Apr. 13, 2007 for copending U.S. Appl. No. 11/365,258.
USPTO Office Action dated Apr. 2, 2009 for copending U.S. Appl. No. 11/325,295.
USPTO Office Action dated Apr. 20, 2007 for copending U.S. Appl. No. 11/366,005.
USPTO Office Action dated Apr. 20, 2007 for copending U.S. Appl. No. 11/365,699.
USPTO Office Action dated Apr. 16, 2008 for copending U.S. Appl. No. 11/365,176.
USPTO Office Action dated May 7, 2009 for copending U.S. Appl. No. 11/846,846.
Smith, J.M., "Deviations from Ideal Reactor Performance," Chemical Engineering Kinetics, 1970, second edition, Chapter 6, McGraw-Hill.
Partenheimer, W., "Catalysis Today" 23 (1995) p. 81.
Copending U.S. Appl. No. 11/366,005, filed Mar. 1, 2006.
Copending U.S. Appl. No. 11/365,698, filed Mar. 1, 2006.
Copending U.S. Appl. No. 11/365,176, filed Mar. 1, 2006.
Copending U.S. Appl. No. 11/365,699, filed Mar. 1, 2006.
Copending U.S. Appl. No. 11/366,004, filed Mar. 1, 2006.
Copending U.S. Appl. No. 11/365,929, filed Mar. 1, 2006.
Copending U.S. Appl. No. 11/365,258, filed Mar. 1, 2006.
U.S. Appl. No. 10/975,252, filed Oct. 28, 2004.
U.S. Appl. No. 10/975,256, filed Oct. 28, 2004.
U.S. Appl. No. 11/154,116, filed Jun. 16, 2005.
U.S. Appl. No. 11/154,140, filed Jun. 16, 2005.
U.S. Appl. No. 11/154,163, filed Jun. 16, 2005.
U.S. Appl. No. 11/154,202, filed Jun. 16, 2005.
U.S. Appl. No. 11/154,219, filed Jun. 16, 2005.

U.S. Appl. No. 11/154,220, filed Jun. 16, 2005.
U.S. Appl. No. 11/154,221, filed Jun. 16, 2005.
U.S. Appl. No. 11/154,448, filed Jun. 16, 2005.
U.S. Appl. No. 11/154,478, filed Jun. 16, 2005.
U.S. Appl. No. 11/154,479, filed Jun. 16, 2005.
U.S. Appl. No. 11/154,480, filed Jun. 16, 2005.
U.S. Appl. No. 11/154,481, filed Jun. 16, 2005.
U.S. Appl. No. 11/154,482, filed Jun. 16, 2005.
U.S. Appl. No. 11/154,484, filed Jun. 16, 2005.
U.S. Appl. No. 11/191,766, filed Jul. 28, 2005.
U.S. Appl. No. 11/201,512, filed Aug. 11, 2005.
U.S. Appl. No. 11/201,799, filed Aug. 11, 2005.
U.S. Appl. No. 11/271,308, filed Nov. 10, 2005.
U.S. Appl. No. 11/325,295, filed Jan. 4, 2006.
U.S. Appl. No. 11/365,054, filed Mar. 1, 2006.
U.S. Appl. No. 11/365,055, filed Mar. 1, 2006.
U.S. Appl. No. 11/365,074, filed Mar. 1, 2006.
U.S. Appl. No. 11/365,079, filed Mar. 1, 2006.
U.S. Appl. No. 11/365,080, filed Mar. 1, 2006.
U.S. Appl. No. 11/365,117, filed Mar. 1, 2006.
U.S. Appl. No. 11/365,255, filed Mar. 1, 2006.
U.S. Appl. No. 11/365,256, filed Mar. 1, 2006.
U.S. Appl. No. 11/365,350, filed Mar. 1, 2006.
U.S. Appl. No. 11/365,439, filed Mar. 1, 2006.
U.S. Appl. No. 11/365,440, filed Mar. 1, 2006.
U.S. Appl. No. 11/365,441, filed Mar. 1, 2006.
U.S. Appl. No. 11/365,461, filed Mar. 1, 2006.
U.S. Appl. No. 11/365,652, filed Mar. 1, 2006.
Copending U.S. Appl. No. 11/325,295, filed Jan. 4, 2006.
Arun Pal Aneja and Viney Pal Aneja, "The Effect of Water and Air Contamination on Poly(Ethylene Terephthalate) Formation", Polymer Engineering Reviews, 1982, pp. 123-133, vol. 2, No. 2.
V. F. Nazimok et al., "Tere-or Isophthalic Acids," Chemical Abstracts, Mar. 3, 1986, pp. 657, vol. 104, No. 9, Columbus, Ohio.
USPTO office action dated Jun. 25, 2007 for copending U.S. Appl. No. 11/325,295.
USPTO Notice of Allowance dated Jul. 3, 2008 for copending U.S. Appl. No. 11/365,258.
USPTO Office Action dated Jul. 16, 2008 for copending U.S. Appl. No. 11/366,005.
USPTO Office Action dated Jul. 16, 2008 for copending U.S. Appl. No. 11/846,846.
Nauman, E.B., "Chemical Reactor Design, Optimization, and Scaleup," 2001, p. 17, McGraw-Hill Professional.
Copending U.S. Appl. No. 11/846,846, filed Aug. 29, 2007, Thomas Woodruff et al.
USPTO Notice of Allowance dated Sep. 28, 2007 for copending U.S. Appl. No. 11/365,699.
USPTO Notice of Allowance dated Sep. 28, 2007 for copending U.S. Appl. No. 11/365,258.
USPTO Office Action dated Oct. 3, 2007 for copending U.S. Appl. No. 11/365,929.
USPTO Office Action dated Oct. 3, 2007 for copending U.S. Appl. No. 11/365,176.
USPTO Notice of Allowance dated Sep. 28, 2007 for copending U.S. Appl. No. 11/366,005.
USPTO Office Action dated Oct. 30, 2008 for copending U.S. Appl. No. 11/325,295.
USPTO Office Action dated Nov. 2, 2007 for copending U.S. Appl. No. 11/366,005.
USPTO Office Action dated Nov. 2, 2007 for copending U.S. Appl. No. 11/365,258.
USPTO Office Action dated Nov. 6, 2007 for copending U.S. Appl. No. 11/325,295.
USPTO Notice of Allowance dated Nov. 20, 2007 for copending U.S. Appl. No. 11/365,176.
USPTO Notice of Allowance dated Dec. 5, 2007 for copending U.S. Appl. No. 11/365,929.
USPTO Office Action dated Dec. 5, 2008 for copending U.S. Appl. No. 11/846,846.
USPTO Office Action dated Dec. 19, 2008 for copending U.S. Appl. No. 11/365,698.
New Copending U.S. Appl. No. 12/709,547, filed Feb. 22, 2010, Thomas Earl Woodruff, et al.
USPTO Office Action dated Aug. 5, 2009 for copending U.S. Appl. No. 11/365,698.
USPTO Office Action dated Feb. 25, 2010 for copending U.S. Appl. No. 11/846,846.
USPTON Notice of Allowance dated May 27, 2010 for copending U.S. Appl. No. 11/365,698.

* cited by examiner

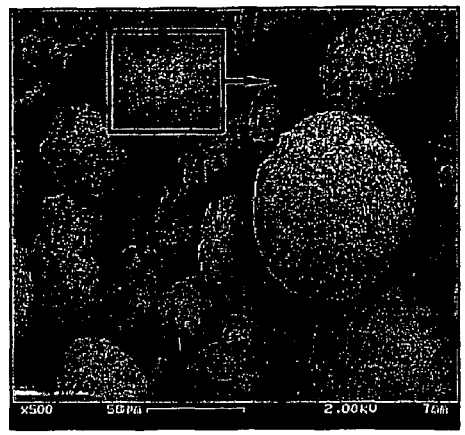 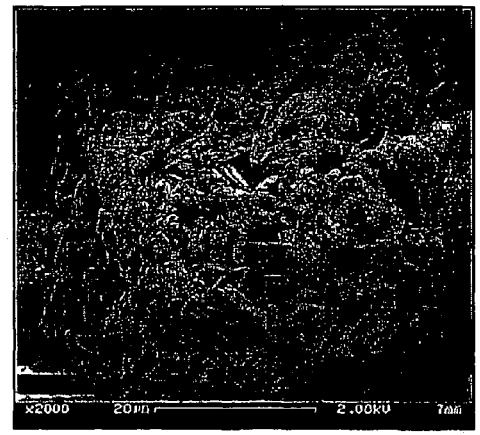
FIG. 19A  FIG. 19B
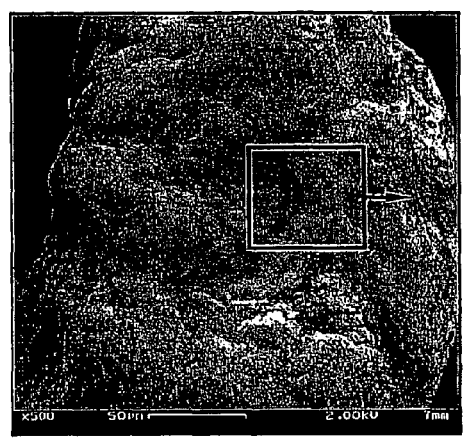 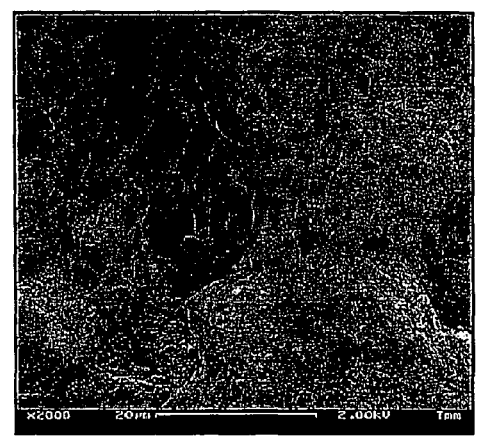
FIG. 20A  FIG. 20B

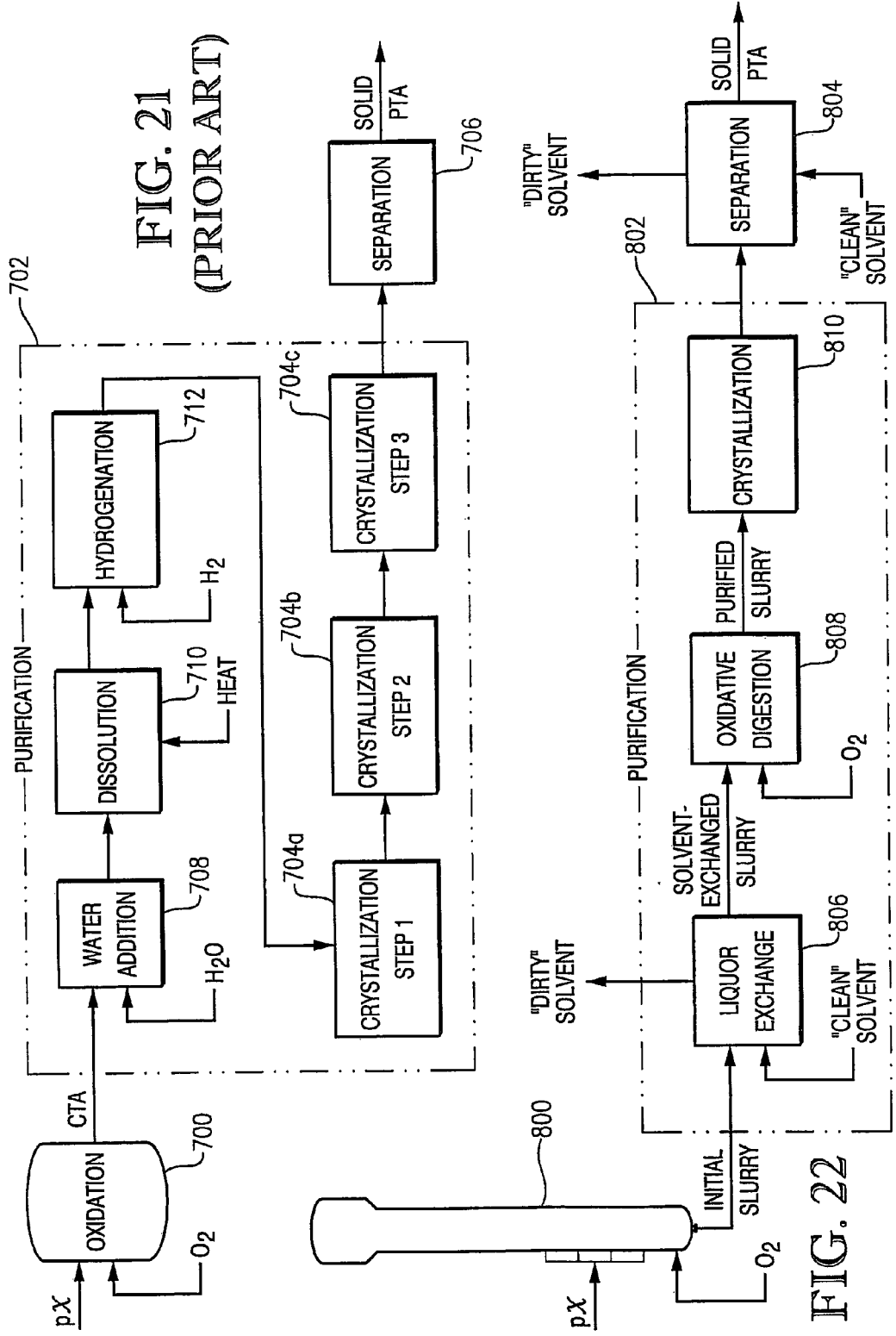

POLYCARBOXYLIC ACID PRODUCTION SYSTEM EMPLOYING ENHANCED MULTISTAGE OXIDATIVE DIGESTION

FIELD OF THE INVENTION

This invention relates generally to a process for the production of polycarboxylic acids. One aspect of the invention concerns a process in which a dialkyl aromatic compound (e.g., para-xylene) is oxidized to produce a crude aromatic dicarboxylic acid (e.g., crude terephthalic acid), and the resulting crude aromatic dicarboxylic acid is thereafter subjected to purification and separation to produce a purified aromatic dicarboxylic acid (e.g., purified terephthalic acid).

BACKGROUND OF THE INVENTION

A wide variety of processes for producing purified terephthalic acid (PTA) have been disclosed in the prior art. However, only a handful of these prior processes are widely practiced commercially. One such commercial process employs two stages of oxidation, with liquor exchange between the oxidation stages. In the first stage of oxidation, referred to herein as "primary oxidation," para-xylene is oxidized to terephthalic acid (TPA). The product of primary oxidation is a crude slurry containing a liquid mother liquor and crude terephthalic acid (CTA) particles. This crude slurry produced in primary oxidation is subjected to a liquor exchange process that replaces a substantial portion of the original mother liquor with a cleaner solvent. The resulting liquor-exchanged slurry is then purified in the second stage of oxidation, referred to herein as "oxidative digestion." Oxidative digestion produces purer TPA particles through a process that involves the continuous dissolution and reprecipitation of TPA particles under oxidation conditions. The TPA particles produced from oxidative digestion are purer than the CTA particles introduced into oxidative digestion for two main reasons: (1) reaction intermediates (e.g., 4-carboxybenzaldehyde (4-CBA) and para-toluic acid (PTAC)) originally trapped in the CTA particles are further oxidized to TPA during oxidative digestion; and (2) the dissolution and reprecipitation associated with oxidative digestion partitions a portion of the relatively unreactive aromatic impurities (e.g. isophthalic acid (IPA)) out of the solid phase and into the liquid phase. In addition to increasing the purity of the TPA particles, oxidative digestion also has the advantage of producing TPA particles that are larger than the CTA particles subjected to oxidative digestion. These larger TPA particles produced by oxidative digestion facilitate more efficient and effective downstream processing.

The liquor exchange step between primary oxidation and oxidative digestion serves two main functions: (1) removal of soluble, relatively unreactive aromatic impurities (e.g., IPA) from the solid CTA; and (2) removal of catalyst compounds present in the liquid phase of the crude slurry. The removal of relatively unreactive aromatic impurities provided by liquor exchange allows the CTA to be adequately purified without hydrogenation, which is very expensive. The catalyst removal provided by liquor exchange reduces chemical activity during oxidative digestion, leading to reduced carbon burn losses while still retaining reactivity necessary for further conversion of aromatic reaction intermediate compounds to TPA. The reduction of catalyst concentrations provided by liquor exchange also makes removal of catalyst compounds more efficient and more complete during subsequent isolation of solid PTA product.

Although liquor exchange between the primary oxidation and oxidative digestion steps has its advantages, it can be expensive and difficult to continuously remove the hot, flammable, corrosive, mother liquor from the crude slurry and continuously replace the removed mother liquor with the hot, flammable, corrosive, cleaner solvent. A particularly significant expense associated with this type of liquor exchange step is the liquor exchange that typically takes place in one or more large centrifuges or pressure filters made of expensive metals (e.g., titanium) or metal alloys.

In the past, several sources have proposed that PTA could be made without employing a liquor exchange step between primary oxidation and oxidative digestion. However, in such proposed systems, the increased catalyst concentrations in the feed to oxidative digestion dramatically increases carbon burn losses associated with oxidative digestion. In addition, the proposed PTA production systems that eliminate liquor exchange between primary oxidation and oxidative digestion typically employ a liquor exchange step downstream of oxidative digestion. In this type of system, the mother liquor removed downstream of oxidative digestion has a higher concentration of relatively unreactive aromatic impurities (e.g., IPA) than the mother liquor upstream of the second stage of oxidation. This is because oxidative digestion increases partitioning of relatively unreactive aromatic impurities into the liquid phase. In a continuous PTA production process employing recycled solvent (i.e., recovered and purified solvent originating from mother liquor produced from primary oxidation) as a feed to primary oxidation, the relatively unreactive aromatic impurities not exiting with solid PTA product accumulate in the recycled solvent until otherwise removed or destroyed. Unless auxiliary process steps for purification of the recycled solvent are increased in scope, the concentrations of relatively unreactive aromatic impurities (e.g., IPA) in the recycled solvent continue to rise over time, setting off a cascade of chemical and process consequences such as, for example, an undesirable increase in the formation rate of colored aromatic impurities in primary oxidation and an eventual increase in the color of solid TPA product. The particulars of auxiliary process steps for purification of the recycled solvent have a number of complex interactions with the primary oxidation and oxidative digestion steps and can influence operating costs and product quality significantly. For example, increased recycle of uncolored IPA will actually increase the formation rate of highly colored 2,7 dicarboxyfluorenone (2,7-DCF) with considerable eventual adverse affect on solid TPA product color as the levels of IPA and 2,7-DCF slowly rise to a new steady state concentrations throughout the process.

In view of the foregoing, prior art processes employing two stage oxidation without intermediate liquor exchange have not proven to be commercially viable because, for example, (1) they exhibit increased carbon burn losses during oxidative digestion, (2) they can not use recycled solvent, and/or (3) if recycled solvent is used, they require additional expensive purification systems to control the increased contaminant levels in the recycled solvent.

OBJECTS OF THE INVENTION

One object of the present invention is to provide an improved primary oxidation system that produces a crude product slurry having improved purity over conventional primary oxidation systems.

Another object of the invention is to provide a bubble column reactor that facilitates improved liquid-phase oxidation of para-xylene to terephthalic acid (TPA) with reduced formation of impurities.

Still another object of the present invention is to provide a system for producing purified terephthalic acid (PTA) that eliminates the need for liquor exchange upstream of oxidative digestion.

Yet another object of the present invention is to provide a PTA production process that minimizes carbon burn during oxidative digestion, without requiring liquor exchange upstream of oxidative digestion.

Yet still another object of the present invention is to provide a PTA production system that promotes precipitation of relatively unreactive aromatic impurities (e.g., IPA) downstream of oxidative digestion, so that the unreactive aromatic impurities exit the process with the TPA particles and do not need to be purged from the recycled solvent.

It should be noted that the scope of the present invention, as defined in the appended claims, is not limited to processes or apparatuses capable of realizing all of the objects listed above. Rather, the scope of the claimed invention may encompass a variety of systems that do not accomplish all or any of the above-listed objects. Additional objects and advantages of the present invention will be readily apparent to one skilled in the art upon reviewing the following detailed description and associated drawings.

SUMMARY OF THE INVENTION

One embodiment of the present invention concerns a process for making a polycarboxylic acid composition, the process comprising the following steps: (a) subjecting a multi-phase reaction medium to oxidation in a primary oxidation zone under primary oxidation conditions sufficient to produce an initial slurry comprising an initial solid and an initial liquid, wherein the primary oxidation conditions include a primary oxidation temperature in the range of from about 125 to about 200° C., wherein the initial solid comprises a plurality of crude terephthalic acid (CTA) particles, wherein a representative sample of the CTA particles dissolves in one minute to a concentration of at least about 500 ppm in THF when subjected to the timed dissolution test defined herein; (b) subjecting at least a portion of the initial slurry to oxidative digestion in a first digestion zone under first digestion conditions sufficient to produce a first digestion product slurry, wherein the first digestion conditions include a first digestion temperature that is within 20° C. of the primary oxidation temperature; and (c) subjecting at least a portion of the first digestion product slurry to oxidative digestion in a second digestion zone under second digestion conditions sufficient to produce a second digestion product slurry, wherein the second digestion conditions include a second digestion temperature that is greater than both the primary oxidation temperature and the first digestion temperature.

Another embodiment of the present invention a process for making a polycarboxylic acid composition, the process comprising the following steps: (a) subjecting a multi-phase reaction medium to oxidation in a primary oxidation zone under primary oxidation conditions sufficient to produce an initial slurry comprising an initial solid and an initial liquid, wherein the primary oxidation conditions include a primary oxidation temperature in the range of from about 125 to about 200° C., wherein the initial solid comprises a plurality of crude terephthalic acid (CTA) particles, wherein a representative sample of the initial slurry has one or more of the following characteristics based on the combined solid and liquid slurry components: (i) contains less than about 9,000 ppmw of isophthalic acid (IPA), (ii) contains less than about 15,000 ppmw of benzoic acid (BA), (iii) contains less than about 64 ppmw of 4,4'-dicarboxybiphenyl (4,4'-DCB), (iv) contains less than about 70 ppmw of 2,6-dicarboxyfluorenone (2,6-DCF), (v) contains less than about 12 ppmw of 2,7-dicarboxyfluorenone (2,7-DCF), (vi) contains less than about 12 ppmw of 9-fluorenone-2-carboxylic acid (9F-2CA), (vii) contains less than about 4 ppmw of 4,4'-dicarboxystilbene (4,4'-DCS), (viii) contains less than about 6 ppmw of 4,4'-dicarboxyanthraquinone (4,4'-DCA); (b) subjecting at least a portion of the initial slurry to oxidative digestion in a first digestion zone under first digestion conditions sufficient to produce a first digestion product slurry, wherein the first digestion conditions include a first digestion temperature that is within 20° C. of the primary oxidation temperature; and (c) subjecting at least a portion of the first digestion product slurry to oxidative digestion in a second digestion zone under second digestion conditions sufficient to produce a second digestion product slurry, wherein the second digestion conditions include a second digestion temperature that is greater than both the primary oxidation temperature and the first digestion temperature.

BRIEF DESCRIPTION OF THE DRAWINGS

Preferred embodiments of the invention are described in detail below with reference to the attached drawing figures, wherein;

FIGS. 19A and 19B are magnified views of crude terephthalic acid (CTA) particles produced in accordance with one embodiment of the present invention, particularly illustrating that each CTA particle is a low density, high surface area particle composed of a plurality of loosely-bound CTA sub-particles;

FIGS. 20A and 20B are magnified views of a conventionally-produced CTA, particularly illustrating that the conventional CTA particle has a larger particle size, higher density, and lower surface area than the inventive CTA particle of FIGS. 19A and 19B;

FIG. 21 is a simplified process flow diagram of a prior art process for making purified terephthalic acid (PTA), where the prior art process employs hydrogenation to purify the TPA;

FIG. 22 is a simplified process flow diagram of a process for making PTA, particularly illustrating a conventional purification system being use to process the initial slurry produced from a primary oxidation reactor configured and operated in accordance with an embodiment of the present invention;

DETAILED DESCRIPTION

Figure 1:
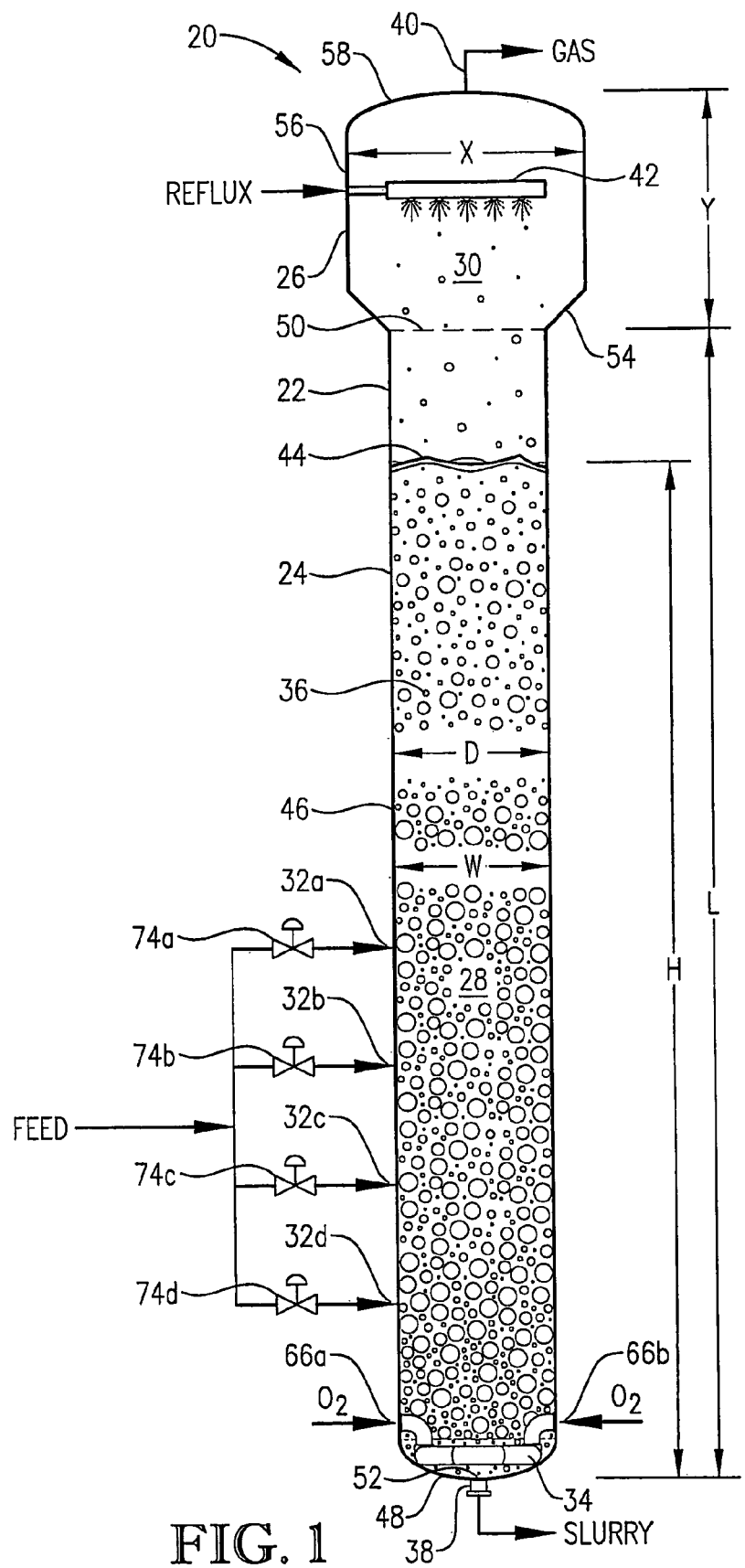
FIG. 1 is a side view of an oxidation reactor constructed in accordance with one embodiment of the present invention, particularly illustrating the introduction of feed, oxidant, and reflux streams into the reactor, the presence of a multi-phase reaction medium in the reactor, and the withdrawal of a gas and a slurry from the top and bottom of the reactor, respectively.

In accordance with one embodiment of the present invention, an improved primary oxidation system is provided. This improved primary oxidation system produces a purer initial slurry than conventional primary oxidation systems. The purer initial slurry produced by the improved primary oxidation system can be subsequently processed using novel techniques that are the subjected matter of certain embodiments of the present invention.

As used herein, the term "primary oxidation" denotes oxidation of an aromatic compound in at least one primary oxidation reactor/zone to produce a polycarboxylic acid, where at least 80 percent of the mass of the aromatic compound introduced into the primary oxidation reactor/zone is oxidized to the polycarboxylic acid in the primary oxidation reactor/zone. Although the primary oxidation reactor/zone can be formed by a plurality of vessels, conduits, and/or stages in a vessel, in a preferred embodiment of the present invention, primary oxidation is carried out in a single reaction vessel.

Primary oxidation is preferably carried out in the liquid phase of a multi-phase reaction medium contained in one or more agitated reactors. Suitable agitated reactors include, for example, bubble-agitated reactors (e.g., bubble column reactors), mechanically agitated reactors (e.g., continuous stirred tank reactors), and flow agitated reactors (e.g., jet reactors). In one embodiment of the invention, the primary oxidation is carried out using at least one bubble column reactor.

As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the term "agitation" shall denote work dissipated into the reaction medium causing fluid flow and/or mixing. As used herein, the terms "majority," "primarily," and "predominately" shall mean more than 50 percent. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. As used herein, the term "flow agitation" shall denote agitation of the reaction medium caused by high velocity injection and/or recirculation of one or more fluids in the reaction medium. For example, flow agitation can be provided by nozzles, ejectors, and/or eductors.

In a preferred embodiment of the present invention, less than about 40 percent of the agitation of the reaction medium in the primary oxidation reactor during oxidation is provided by mechanical and/or flow agitation, more preferably less than about 20 percent of the agitation is provided by mechanical and/or flow agitation, and most preferably less than 5 percent of the agitation is provided by mechanical and/or flow agitation. Preferably, the amount of mechanical and/or flow agitation imparted to the multi-phase reaction medium during oxidation is less than about 3 kilowatts per cubic meter of the reaction medium, more preferably less than about 2 kilowatts per cubic meter, and most preferably less than 1 kilowatt per cubic meter.

Referring now to FIG. 1, a preferred bubble column primary oxidation reactor 20 is illustrated as comprising a vessel shell 22 having a reaction section 24 and a disengagement section 26. Reaction section 24 defines a reaction zone 28, while disengagement section 26 defines a disengagement zone 30. A predominately liquid-phase feed stream is introduced into reaction zone 28 via feed inlets 32a,b,c,d. A predominately gas-phase oxidant stream is introduced into reaction zone 28 via an oxidant sparger 34 located in the lower portion of reaction zone 28. The liquid-phase feed stream and gas-phase oxidant stream cooperatively form a multi-phase reaction medium 36 within reaction zone 28. Multi-phase reaction medium 36 comprises a liquid phase and a gas phase. More preferably, multiphase reaction medium 36 comprises a three-phase medium having solid-phase, liquid-phase, and gas-phase components. The solid-phase component of the reaction medium 36 preferably precipitates within reaction zone 28 as a result of the oxidation reaction carried out in the liquid phase of reaction medium 36. Primary oxidation reactor 20 includes a slurry outlet 38 located near the bottom of reaction zone 28 and a gas outlet 40 located near the top of disengagement zone 30. A slurry effluent comprising liquid-phase and solid-phase components of reaction medium 36 is withdrawn from reaction zone 28 via slurry outlet 38, while a predominantly gaseous effluent is withdrawn from disengagement zone 30 via gas outlet 40. The slurry effluent of primary oxidation is referred to herein as "initial slurry."

The liquid-phase feed stream introduced into primary oxidation reactor 20 via feed inlets 32a,b,c,d preferably comprises an aromatic compound, a solvent, and a catalyst system.

The aromatic compound present in the liquid-phase feed stream preferably has at least one attached hydrocarbyl group or at least one attached substituted hydrocarbyl group or at least one attached heteroatom or at least one attached carboxylic acid function (—COOH). More preferably, the aromatic compound has at least one attached hydrocarbyl group or at least one attached substituted hydrocarbyl group with each attached group comprising from 1 to 5 carbon atoms. Still more preferably, the aromatic compound has exactly two attached groups with each attached group comprising exactly one carbon atom and consisting of methyl groups and/or substituted methyl groups and/or at most one carboxylic acid group. Even more preferably, the aromatic compound is para-xylene, meta-xylene, ortho-xylene, para-tolualdehyde, meta-tolualdehyde, terephthaldehyde, isophthaldehyde, para-toluic acid, meta-toluic acid, and/or acetaldehyde. Most preferably, the aromatic compound is para-xylene.

A "hydrocarbyl group," as defined herein, is at least one carbon atom that is bonded only to hydrogen atoms or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. Aromatic compounds, as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

If the aromatic compound present in the liquid-phase feed stream is a normally-solid compound (i.e., is a solid at standard temperature and pressure), it is preferred for the aromatic compound to be substantially dissolved in the solvent when introduced into reaction zone 28. It is preferred for the boiling point of the aromatic compound at atmospheric pressure to be at least about 50° C. More preferably, the boiling point of the aromatic compound is in the range of from about 80 to about 400° C., and most preferably in the range of from 125 to 155° C. The amount of aromatic compound present in the liquid-phase feed is preferably in the range of from about 2 to about 40 weight percent, more preferably in the range of from about 4 to about 20 weight percent, and most preferably in the range of from 6 to 15 weight percent.

It is now noted that the aromatic compound present in the liquid-phase feed may comprise a combination of two or more different oxidizable chemicals. These two or more different chemical materials can be fed commingled in the liquid-phase feed stream or may be fed separately in multiple feed streams. For example, an aromatic compound comprising para-xylene, meta-xylene, para-tolualdehyde, and para-toluic acid may be fed to the reactor via a single inlet or multiple separate inlets.

The solvent present in the liquid-phase feed stream preferably comprises an acid component and a water component. The solvent is preferably present in the liquid-phase feed stream at a concentration in the range of from about 60 to about 98 weight percent, more preferably in the range of from about 80 to about 96 weight percent, and most preferably in the range of from 85 to 94 weight percent. The acid component of the solvent is preferably primarily an organic low molecular weight monocarboxylic acid having 1-6 carbon atoms, more preferably 2 carbon atoms. Most preferably, the acid component of the solvent is primarily acetic acid. Preferably, the acid component makes up at least about 75 weight percent of the solvent, more preferably at least about 80 weight percent of the solvent, and most preferably 85 to 98 weight percent of the solvent, with the balance being primarily water. The solvent introduced into primary oxidation reactor 20 can include small quantities of impurities such as, for example, para-tolualdehyde, terephthaldehyde, 4-carboxybenzaldehyde (4-CBA), benzoic acid, para-toluic acid, para-toluic aldehyde, alpha-bromo-para-toluic acid, isophthalic acid, phthalic acid, trimellitic acid, polyaromatics, and/or suspended particulate. It is preferred that the total amount of impurities in the solvent introduced into primary oxidation reactor 20 is less than about 3 weight percent.

The catalyst system present in the liquid-phase feed stream is preferably a homogeneous, liquid-phase catalyst system capable of promoting oxidation (including partial oxidation) of the aromatic compound. More preferably, the catalyst system comprises at least one multivalent transition metal. Still more preferably, the multivalent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the liquid-phase feed stream to be such that the concentration of cobalt in the liquid phase of reaction medium 36 is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the liquid-phase feed stream to be such that the concentration of bromine in the liquid phase of reaction medium 36 is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the liquid-phase feed stream to be such that the concentration of manganese in the liquid phase of reaction medium 36 is maintained in the range of from about 20 to about 1,000 ppmw, more preferably in the range of from about 40 to about 500 ppmw, most preferably in the range of from 50 to 200 ppmw.

The concentrations of the cobalt, bromine, and/or manganese in the liquid phase of reaction medium 36, provided above, are expressed on a time-averaged and volume-averaged basis. As used herein, the term "time-averaged" shall denote an average of at least 10 measurements taken equally over a continuous period of at least 100 seconds. As used herein, the term "volume-averaged" shall denote an average of at least 10 measurements taken at uniform 3-dimensional spacing throughout a certain volume.

The weight ratio of cobalt to bromine (Co:Br) in the catalyst system introduced into reaction zone 28 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced into reaction zone 28 is preferably in the range of from about 0.3:1 to about 40:1, more preferably in the range of from about 5:1 to about 30:1, and most preferably in the range of from 10:1 to 25:1.

The liquid-phase feed stream introduced into primary oxidation reactor 20 can include small quantities of impurities such as, for example, toluene, ethylbenzene, para-tolualdehyde, terephthaldehyde, 4-carboxybenzaldehyde (4-CBA), benzoic acid, para-toluic acid, para-toluic aldehyde, alpha bromo para-toluic acid, isophthalic acid, phthalic acid, trimellitic acid, polyaromatics, and/or suspended particulate. When primary oxidation reactor 20 is employed for the production of terephthalic acid, meta-xylene and ortho-xylene are also considered impurities. It is preferred that the total amount of impurities in the liquid-phase feed stream introduced into primary oxidation reactor 20 is less than about 3 weight percent.

Although FIG. 1 illustrates an embodiment where the aromatic compound, the solvent, and the catalyst system are mixed together and introduced into primary oxidation reactor 20 as a single feed stream, in an alternative embodiment of the present invention, the aromatic compound, the solvent, and the catalyst can be separately introduced into primary oxidation reactor 20. For example, it is possible to feed a pure para-xylene stream into primary oxidation reactor 20 via an inlet separate from the solvent and catalyst inlet(s).

The predominately gas-phase oxidant stream introduced into primary oxidation reactor 20 via oxidant sparger 34 comprises molecular oxygen ($O_2$). Preferably, the oxidant stream comprises in the range of from about 5 to about 40 mole percent molecular oxygen, more preferably in the range of from about 15 to about 30 mole percent molecular oxygen, and most preferably in the range of from 18 to 24 mole percent molecular oxygen. It is preferred for the balance of the oxidant stream to be comprised primarily of a gas or gasses, such as nitrogen, that are inert to oxidation. More preferably, the oxidant stream consists essentially of molecular oxygen and nitrogen. Most preferably, the oxidant stream is dry air that comprises about 21 mole percent molecular oxygen and about 78 to about 81 mole percent nitrogen. In an alternative embodiment of the present invention, the oxidant stream can comprise substantially pure oxygen.

Referring again to FIG. 1, primary oxidation reactor 20 is preferably equipped with a reflux distributor 42 positioned above an upper surface 44 of reaction medium 36. Reflux distributor 42 is operable to introduce droplets of a predominately liquid-phase reflux stream into disengagement zone 30 by any means of droplet formation known in the art. More preferably, reflux distributor 42 produces a spray of droplets directed downwardly towards upper surface 44 of reaction medium 36. Preferably, this downward spray of droplets affects (i.e., engages and influences) at least about 50 percent of the maximum horizontal cross-sectional area of disengagement zone 30. More preferably, the spray of droplets affects at least about 75 percent of the maximum horizontal cross-sectional area of disengagement zone 30. Most preferably, the spray of droplets affects at least 90 percent of the maximum horizontal cross-sectional area of disengagement zone 30. This downward liquid reflux spray can help prevent foaming at or above upper surface 44 of reaction medium 36 and can also aid in the disengagement of any liquid or slurry droplets entrained in the upwardly moving gas that flows towards gas outlet 40. Further, the liquid reflux may serve to reduce the amount of particulates and potentially precipitating compounds (e.g., dissolved benzoic acid, para-toluic acid, 4-CBA, terephthalic acid, and catalyst metal salts) exiting in the gaseous effluent withdrawn from disengagement zone 30 via gas outlet 40. In addition, the introduction of reflux droplets into disengagement zone 30 can, by a distillation action, be used to adjust the composition of the gaseous effluent withdrawn via gas outlet 40.

The liquid reflux stream introduced into primary oxidation reactor 20 via reflux distributor 42 preferably has about the same composition as the solvent component of the liquid-phase feed stream introduced into primary oxidation reactor 20 via feed inlets 32$a,b,c,d$. Thus, it is preferred for the liquid reflux stream to comprise an acid component and water. The acid component of the reflux stream is preferably a low molecular weight organic monocarboxylic acid having 1-6 carbon atoms, more preferably 2 carbon atoms. Most preferably, the acid component of the reflux stream is acetic acid. Preferably, the acid component makes up at least about 75 weight percent of the reflux stream, more preferably at least about 80 weight percent of the reflux stream, and most preferably 85 to 98 weight percent of the reflux stream, with the balance being water. Because the reflux stream typically has substantially the same composition as the solvent in the liquid-phase feed stream, when this description refers to the "total solvent" introduced into the reactor, such "total solvent" shall include both the reflux stream and the solvent portion of the feed stream.

During liquid-phase oxidation in primary oxidation reactor 20, it is preferred for the feed, oxidant, and reflux streams to be substantially continuously introduced into reaction zone 28, while the gas and slurry effluent streams are substantially continuously withdrawn from reaction zone 28. As used herein, the term "substantially continuously" shall mean for a period of at least 10 hours interrupted by less than 10 minutes. During oxidation, it is preferred for the aromatic compound (e.g., para-xylene) to be substantially continuously introduced into reaction zone 28 at a rate of at least about 8,000 kilograms per hour, more preferably at a rate in the range of from about 15,000 to about 200,000 kilograms per hour, still more preferably in the range of from about 22,000 to about 150,000 kilograms per hour, and most preferably in the range of from 30,000 to 100,000 kilograms per hour. Although it is generally preferred for the flow rates of the incoming feed, oxidant, and reflux streams to be substantially steady, it is now noted that one embodiment of the presenting invention contemplates pulsing the incoming feed, oxidant, and/or reflux stream in order to improve mixing and mass transfer. When the incoming feed, oxidant, and/or reflux stream are introduced in a pulsed fashion, it is preferred for their flow rates to vary within about 0 to about 500 percent of the steady-state flow rates recited herein, more preferably within about 30 to about 200 percent of the steady-state flow rates recited herein, and most preferably within 80 to 120 percent of the steady-state flow rates recited herein.

The average space-time rate of reaction (STR) in primary oxidation reactor 20 is defined as the mass of the aromatic compound fed per unit volume of reaction medium 36 per unit time (e.g., kilograms of para-xylene fed per cubic meter per hour). In conventional usage, the amount of aromatic compound not converted to product would typically be subtracted from the amount of aromatic compound in the feed stream before calculating the STR. However, conversions and yields are typically high for many of the aromatic compounds preferred herein (e.g., para-xylene), and it is convenient to define the term herein as stated above. For reasons of capital cost and operating inventory, among others, it is generally preferred that the reaction be conducted with a high STR. However, conducting the reaction at increasingly higher STR may affect the quality or yield of the partial oxidation. Primary oxidation reactor 20 is particularly useful when the STR of the aromatic compound (e.g., para-xylene) is in the range of from about 25 kilograms per cubic meter per hour to about 400 kilograms per cubic meter per hour, more preferably in the range of from about 30 kilograms per cubic meter per hour to about 250 kilograms per cubic meter per hour, still more preferably from about 35 kilograms per cubic meter per hour to about 150 kilograms per cubic meter per hour, and most preferably in the range of from 40 kilograms per cubic meter per hour to 100 kilograms per cubic meter per hour.

The oxygen-STR in primary oxidation reactor 20 is defined as the weight of molecular oxygen consumed per unit volume of reaction medium 36 per unit time (e.g., kilograms of molecular oxygen consumed per cubic meter per hour). For reasons of capital cost and oxidative consumption of solvent, among others, it is generally preferred that the reaction be conducted with a high oxygen-STR. However, conducting the reaction at increasingly higher oxygen-STR eventually reduces the quality or yield of the partial oxidation. Without being bound by theory, it appears that this possibly relates to the transfer rate of molecular oxygen from the gas phase into the liquid at the interfacial surface area and thence into the bulk liquid. Too high an oxygen-STR possibly leads to too low a dissolved oxygen content in the bulk liquid phase of the reaction medium.

The global-average-oxygen-STR is defined herein as the weight of all oxygen consumed in the entire volume of reaction medium 36 per unit time (e.g., kilograms of molecular oxygen consumed per cubic meter per hour). Primary oxidation reactor 20 is particularly useful when the global-average-oxygen-STR is in the range of from about 25 kilograms per cubic meter per hour to about 400 kilograms per cubic meter per hour, more preferably in the range of from about 30 kilograms per cubic meter per hour to about 250 kilograms per cubic meter per hour, still more preferably from about 35 kilograms per cubic meter per hour to about 150 kilograms per cubic meter per hour, and most preferably in the range of from 40 kilograms per cubic meter per hour to 100 kilograms per cubic meter per hour.

During oxidation in primary oxidation reactor 20, it is preferred for the ratio of the mass flow rate of the total solvent (from both the feed and reflux streams) to the mass flow rate of the aromatic compound entering reaction zone 28 to be maintained in the range of from about 2:1 to about 50:1, more preferably in the range of from about 5:1 to about 40:1, and most preferably in the range of from 7.5:1 to 25:1. Preferably, the ratio of the mass flow rate of solvent introduced as part of the feed stream to the mass flow rate of solvent introduced as part of the reflux stream is maintained in the range of from about 0.5:1 to no reflux stream flow whatsoever, more preferably in the range of from about 0.5:1 to about 4:1, still more preferably in the range of from about 1:1 to about 2:1, and most preferably in the range of from 1.25:1 to 1.5:1.

During liquid-phase oxidation in primary oxidation reactor 20, it is preferred for the oxidant stream to be introduced into primary oxidation reactor 20 in an amount that provides molecular oxygen somewhat exceeding the stoichiometric oxygen demand. The amount of excess molecular oxygen required for best results with a particular aromatic compound affects the overall economics of the liquid-phase oxidation. During liquid-phase oxidation in primary oxidation reactor 20, it is preferred that the ratio of the mass flow rate of the oxidant stream to the mass flow rate of the oxidizable aromatic compound (e.g., para-xylene) entering reactor 20 is maintained in the range of from about 0.5:1 to about 20:1, more preferably in the range of from about 1:1 to about 10:1, and most preferably in the range of from 2:1 to 6:1.

Referring again to FIG. 1, the feed, oxidant, and reflux streams introduced into primary oxidation reactor 20 cooperatively form at least a portion of multi-phase reaction medium 36. Reaction medium 36 is preferably a three-phase medium comprising a solid phase, a liquid phase, and a gas phase. As mentioned above, oxidation of the aromatic compound (e.g., para-xylene) takes place predominately in the liquid phase of reaction medium 36. Thus, the liquid phase of reaction medium 36 comprises dissolved oxygen and the aromatic compound. The exothermic nature of the oxidation reaction that takes place in primary oxidation reactor 20 causes a portion of the solvent (e.g., acetic acid and water) introduced via feed inlets 32a,b,c,d to boil/vaporize. Thus, the gas phase of reaction medium 36 in reactor 20 is formed primarily of vaporized solvent and an undissolved, unreacted portion of the oxidant stream.

Certain prior art oxidation reactors employ heat exchange tubes/fins to heat or cool the reaction medium. However, such heat exchange structures may be undesirable in the inventive reactor and process described herein. Thus, it is preferred for primary oxidation reactor 20 to include substantially no surfaces that contact reaction medium 36 and exhibit a time-averaged heat flux greater than 30,000 watts per meter squared. In addition, it is preferred for less than about 50 percent of the time-averaged heat of reaction of reaction medium 36 to be removed by heat exchange surfaces, more preferably less than about 30 percent of the heat of reaction is removed by heat exchange surfaces, and most preferably less than 10 percent of the heat or reaction is removed by heat exchange surfaces.

The concentration of dissolved oxygen in the liquid phase of reaction medium 36 is a dynamic balance between the rate of mass transfer from the gas phase and the rate of reactive consumption within the liquid phase (i.e. it is not set simply by the partial pressure of molecular oxygen in the supplying gas phase, though this is one factor in the supply rate of dissolved oxygen and it does affect the limiting upper concentration of dissolved oxygen). The amount of dissolved oxygen varies locally, being higher near bubble interfaces. Globally, the amount of dissolved oxygen depends on the balance of supply and demand factors in different regions of reaction medium 36. Temporally, the amount of dissolved oxygen depends on the uniformity of gas and liquid mixing relative to chemical consumption rates. In designing to match appropriately the supply of and demand for dissolved oxygen in the liquid phase of reaction medium 36, it is preferred for the time-averaged and volume-averaged oxygen concentration in the liquid phase of reaction medium 36 to be maintained above about 1 ppm molar, more preferably in the range from about 4 to about 1,000 ppm molar, still more preferably in the range from about 8 to about 500 ppm molar, and most preferably in the range from 12 to 120 ppm molar.

The liquid-phase oxidation reaction carried out in primary oxidation reactor 20 is preferably a precipitating reaction that generates solids. More preferably, the liquid-phase oxidation carried out in primary oxidation reactor 20 causes at least about 10 weight percent of the aromatic compound (e.g., para-xylene) introduced into reaction zone 28 to form the solid polycarboxylic acid compound (e.g., crude terephthalic acid particles) in reaction medium 36. Still more preferably, the liquid-phase oxidation causes at least about 50 weight percent of the aromatic compound to form the solid polycarboxylic acid compound in reaction medium 36. Most preferably, the liquid-phase oxidation causes at least 90 weight percent of the aromatic compound to form the solid polycarboxylic acid in reaction medium 36. It is preferred for the total amount of solids in reaction medium 36 to be greater than about 3 percent by weight on a time-averaged and volume-averaged basis. More preferably, the total amount of solids in reaction medium 36 is maintained in the range of from about 5 to about 40 weight percent, still more preferably in the range of from about 10 to about 35 weight percent, and most preferably in the range of from 15 to 30 weight percent. It is preferred for a substantial portion of the polycarboxylic acid product (e.g., terephthalic acid) produced in primary oxidation reactor 20 to be present in reaction medium 36 as solids, as opposed to remaining dissolved in the liquid phase of reaction medium 36. The amount of the solid phase polycarboxylic acid product present in reaction medium 36 is preferably at least about 25 percent by weight of the total polycarboxylic acid product (solid and liquid phase) in reaction medium 36, more preferably at least about 75 percent by weight of the total polycarboxylic acid product in reaction medium 36, and most preferably at least 95 percent by weight of the total polycarboxylic acid product in reaction medium 36. The numerical ranges provided above for the amount of solids in reaction medium 36 apply to substantially steady-state operation of primary oxidation 20 over a substantially continuous period of time, not to start-up, shut-down, or sub-optimal operation of primary oxidation reactor 20. The amount of solids in reaction medium 36 is determined by a gravimetric method. In this gravimetric method, a representative portion of slurry is withdrawn from the reaction medium and weighed. At conditions that effectively maintain the overall solid-liquid partitioning present within the reaction medium, free liquid is removed from the solids portion by sedimentation or filtration, effectively without loss of precipitated solids and with less than about 10 percent of the initial liquid mass remaining with the portion of solids. The remaining liquid on the solids is evaporated to dryness, effectively without sublimation of solids. The remaining portion of solids is weighed. The ratio of the weight of the portion of solids to the weight of the original portion of slurry is the fraction of solids, typically expressed as a percentage.

The precipitating reaction carried out in primary oxidation reactor 20 can cause fouling (i.e., solids build-up) on the surface of certain rigid structures that contact reaction medium 36. Thus, in one embodiment of the present invention, it is preferred for primary oxidation reactor 20 to include substantially no internal heat exchange, stirring, or baffling structures in reaction zone 28 because such structures would be prone to fouling. If internal structures are present in reaction zone 28, it is desirable to avoid internal structures having outer surfaces that include a significant amount of upwardly facing planar surface area because such upwardly facing planar surfaces would be highly prone to fouling. Thus, if any internal structures are present in reaction zone 28, it is preferred for less than about 20 percent of the total upwardly facing exposed outer surface area of such internal structures to be formed by substantially planar surfaces inclined less than about 15 degrees from horizontal. Internal structures with this type of configuration are referred to herein as having a "non-fouling" configuration.

Referring again to FIG. 1, the physical configuration of primary oxidation reactor 20 helps provide for optimized oxidation of the aromatic compound (e.g., para-xylene) with minimal impurity generation. It is preferred for elongated reaction section 24 of vessel shell 22 to include a substantially cylindrical main body 46 and a lower head 48. The upper end of reaction zone 28 is defined by a horizontal plane 50 extending across the top of cylindrical main body 46. A lower end 52 of reaction zone 28 is defined by the lowest internal surface of lower head 48. Typically, lower end 52 of reaction zone 28 is located proximate the opening for slurry outlet 38. Thus, elongated reaction zone 28 defined within primary oxidation reactor 20 has a maximum length "L" measured from the top end 50 to the bottom end 52 of reaction zone 28 along the axis of elongation of cylindrical main body 46. The length "L" of reaction zone 28 is preferably in the range of from about 10 to about 100 meters, more preferably in the range of from about 20 to about 75 meters, and most preferably in the range of from 25 to 50 meters. Reaction zone 28 has a maximum diameter (width) "D" that is typically equal to the maximum internal diameter of cylindrical main body 46. The maximum diameter "D" of reaction zone 28 is preferably in the range of from about 1 to about 12 meters, more preferably in the range of from about 2 to about 10 meters, still more preferably in the range of from about 3.1 to about 9 meters, and most preferably in the range of from 4 to 8 meters. In a preferred embodiment of the present invention, reaction zone 28 has a length-to-diameter "L:D" ratio in the range of from about 6:1 to about 30:1. Still more preferably, reaction zone 28 has an L:D ratio in the range of from about 8:1 to about 20:1. Most preferably, reaction zone 28 has an L:D ratio in the range of from 9:1 to 15:1.

As discussed above, reaction zone 28 of primary oxidation reactor 20 receives multi-phase reaction medium 36. Reaction medium 36 has a bottom end coincident with lower end 52 of reaction zone 28 and a top end located at upper surface 44. Upper surface 44 of reaction medium 36 is defined along a horizontal plane that cuts through reaction zone 28 at a vertical location where the contents of reaction zone 28 transitions from a gas-phase-continuous state to a liquid-phase-continuous state. Upper surface 44 is preferably positioned at the vertical location where the local time-averaged gas hold-up of a thin horizontal slice of the contents of reaction zone 28 is 0.9.

Reaction medium 36 has a maximum height "H" measured between its upper and lower ends. The maximum width "W" of reaction medium 36 is typically equal to the maximum diameter "D" of cylindrical main body 46. During liquid-phase oxidation in primary oxidation reactor 20, it is preferred that H is maintained at about 60 to about 120 percent of L, more preferably about 80 to about 110 percent of L, and most preferably 85 to 100 percent of L. In a preferred embodiment of the present invention, reaction medium 36 has a height-to-width "H:W" ratio greater than about 3:1. More preferably, reaction medium 36 has an H:W ratio in the range of from about 7:1 to about 25:1. Still more preferably, reaction medium 36 has an H:W ratio in the range of from about 8:1 to about 20:1. Most preferably, reaction medium 36 has an H:W ratio in the range of from 9:1 to 15:1. In one embodiment of the invention, L=H and D=W so that various dimensions or ratios provide herein for L and D also apply to H and W, and vice-versa.

The relatively high L:D and H:W ratios provided in accordance with an embodiment of the invention can contribute to several important advantages of the inventive system. As discussed in further detail below, it has been discovered that higher L:D and H:W ratios, as well as certain other features discussed below, can promote beneficial vertical gradients in the concentrations of molecular oxygen and/or the aromatic compound (e.g., para-xylene) in reaction medium 36. Contrary to conventional wisdom, which would favor a well-mixed reaction medium with relatively uniform concentrations throughout, it has been discovered that the vertical staging of the oxygen and/or the aromatic compound concentrations facilitates a more effective and economical oxidation reaction. Minimizing the oxygen and aromatic compound concentrations near the top of reaction medium 36 can help avoid loss of unreacted oxygen and unreacted aromatic compound through upper gas outlet 40. However, if the concentrations of aromatic compound and unreacted oxygen are low throughout reaction medium 36, then the rate and/or selectivity of oxidation are reduced. Thus, it is preferred for the concentrations of molecular oxygen and/or the aromatic compound to be significantly higher near the bottom of reaction medium 36 than near the top of reaction medium 36.

In addition, high L:D and H:W ratios cause the pressure at the bottom of reaction medium 36 to be substantially greater than the pressure at the top of reaction medium 36. This vertical pressure gradient is a result of the height and density of reaction medium 36. One advantage of this vertical pressure gradient is that the elevated pressure at the bottom of the vessel drives more oxygen solubility and mass transfer than would otherwise be achievable at comparable temperatures and overhead pressures in shallow reactors. Thus, the oxidation reaction can be carried out at lower temperatures than would be required in a shallower vessel. When primary oxidation reactor 20 is used for the partial oxidation of para-xylene to crude terephthalic acid (CTA), the ability to operate at lower reaction temperatures with the same or better oxygen mass transfer rates has a number of advantages. For example, low temperature oxidation of para-xylene reduces the amount of solvent burned during the reaction. As discussed in further detail below, low temperature oxidation also favors the formation of small, high surface area, loosely bound, easily dissolved CTA particles, which can be subjected to more economical purification techniques than the large, low surface area, dense CTA particles produced by conventional high temperature oxidation processes.

During primary oxidation in reactor 20, it is preferred for the time-averaged and volume-averaged temperature of reaction medium 36 to be maintained in the range of from about 125 to about 200° C., more preferably in the range of from about 140 to about 180° C., and most preferably in the range of from 150 to 170° C. The overhead pressure above reaction medium 36 is preferably maintained in the range of from about 1 to about 20 bar gauge (barg), more preferably in the range of from about 2 to about 12 barg, and most preferably in the range of from 4 to 8 barg. Preferably, the pressure difference between the top of reaction medium 36 and the bottom of reaction medium 36 is in the range of from about 0.4 to about 5 bar, more preferably the pressure difference is in the range of from about 0.7 to about 3 bars, and most preferably the pressure difference is 1 to 2 bar. Although it is generally preferred for the overhead pressure above reaction medium 36 to be maintained at a relatively constant value, one embodiment of the present invention contemplates pulsing the overhead pressure to facilitate improved mixing and/or mass transfer in reaction medium 36. When the overhead pressure is pulsed, it is preferred for the pulsed pressures to range between about 60 to about 140 percent of the steady-state overhead pressure recited herein, more preferably between about 85 and about 115 percent of the steady-state overhead pressure recited herein, and most preferably between 95 and 105 percent of the steady-state overhead pressure recited herein.

A further advantage of the high L:D ratio of reaction zone 28 is that it can contribute to an increase in the average superficial velocity of reaction medium 36. The term "superficial velocity" and "superficial gas velocity," as used herein with reference to reaction medium 36, shall denote the volumetric flow rate of the gas phase of reaction medium 36 at an elevation in the reactor divided by the horizontal cross-sectional area of the reactor at that elevation. The increased superficial velocity provided by the high L:D ratio of reaction zone 28 can promote local mixing and increase the gas hold-up of reaction medium 36. The time-averaged superficial velocities of reaction medium 36 at one-quarter height, half height, and/or three-quarter height of reaction medium 36 are preferably greater than about 0.3 meters per second, more preferably in the range of from about 0.4 to about 5 meters per second, still more preferably in the range of from about 0.8 to about 4 meters per second, and most preferably in the range of from 1 to 3 meters per second.

Referring again to FIG. 1, disengagement section 26 of primary oxidation reactor 20 is simply a widened portion of vessel shell 22 located immediately above reaction section 24. Disengagement section 26 reduces the velocity of the upwardly-flowing gas phase in primary oxidation reactor 20 as the gas phase rises above the upper surface 44 of reaction medium 36 and approaches gas outlet 40. This reduction in the upward velocity of the gas phase helps facilitate removal of entrained liquids and/or solids in the upwardly flowing gas phase and thereby reduces undesirable loss of certain components present in the liquid phase of reaction medium 36.

Disengagement section 26 preferably includes a generally frustoconical transition wall 54, a generally cylindrical broad sidewall 56, and an upper head 58. The narrow lower end of transition wall 54 is coupled to the top of cylindrical main body 46 of reaction section 24. The wide upper end of transition wall 54 is coupled to the bottom of broad sidewall 56. It is preferred for transition wall 54 to extend upwardly and outwardly from its narrow lower end at an angle in the range of from about 10 to about 70 degrees from vertical, more preferably in the range of about 15 to about 50 degrees from vertical, and most preferably in the range of from 15 to 45 degrees from vertical. Broad sidewall 56 has a maximum diameter "X" that is generally greater than the maximum diameter "D" of reaction section 24, though when the upper portion of reaction section 24 has a smaller diameter than the overall maximum diameter of reaction section 24, then X may actually be smaller than D. In a preferred embodiment of the present invention, the ratio of the diameter of broad sidewall 56 to the maximum diameter of reaction section 24 "X:D" is in the range of from about 0.8:1 to about 4:1, most preferably in the range of from 1.1:1 to 2:1. Upper head 58 is coupled to the top of broad sidewall 56. Upper head 58 is preferably a generally elliptical head member defining a central opening that permits gas to escape disengagement zone 30 via gas outlet 40. Alternatively, upper head 58 may be of any shape, including conical. Disengagement zone 30 has a maximum height "Y" measured from the top 50 of reaction zone 28 to the uppermost portion of disengagement zone 30. The ratio of the length of reaction zone 28 to the height of disengagement zone 30 "L:Y" is preferably in the range of from about 2:1 to about 24:1, more preferably in the range of from about 3:1 to about 20:1, and most preferably in the range of from 4:1 to 16:1.

Figure 2:
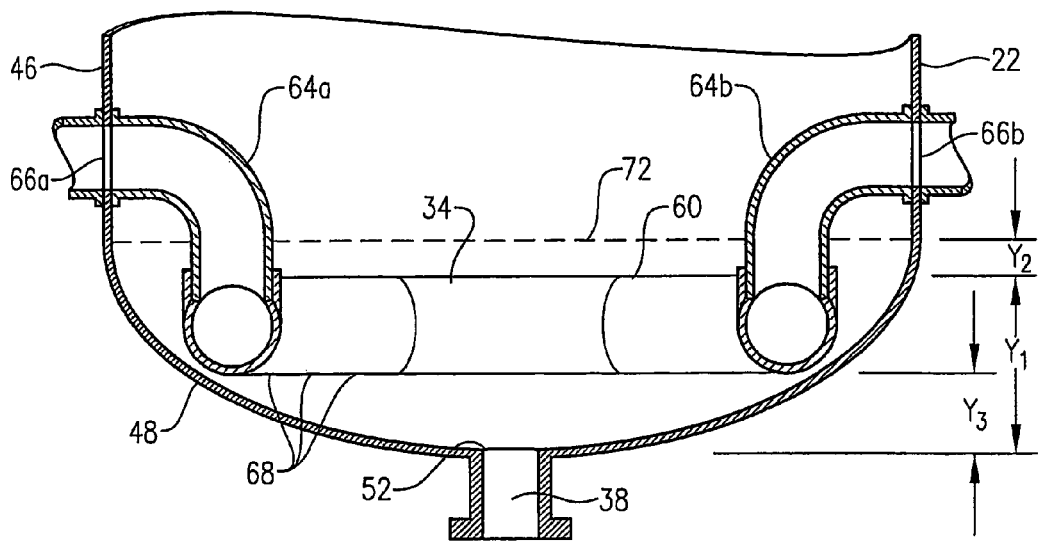
FIG. 2 is an enlarged sectional side view of the bottom of the bubble column reactor taken along line 2-2 in FIG. 3, particularly illustrating the location and configuration of a oxidant sparger used to introduce the oxidant stream into the reactor.
Figure 3:
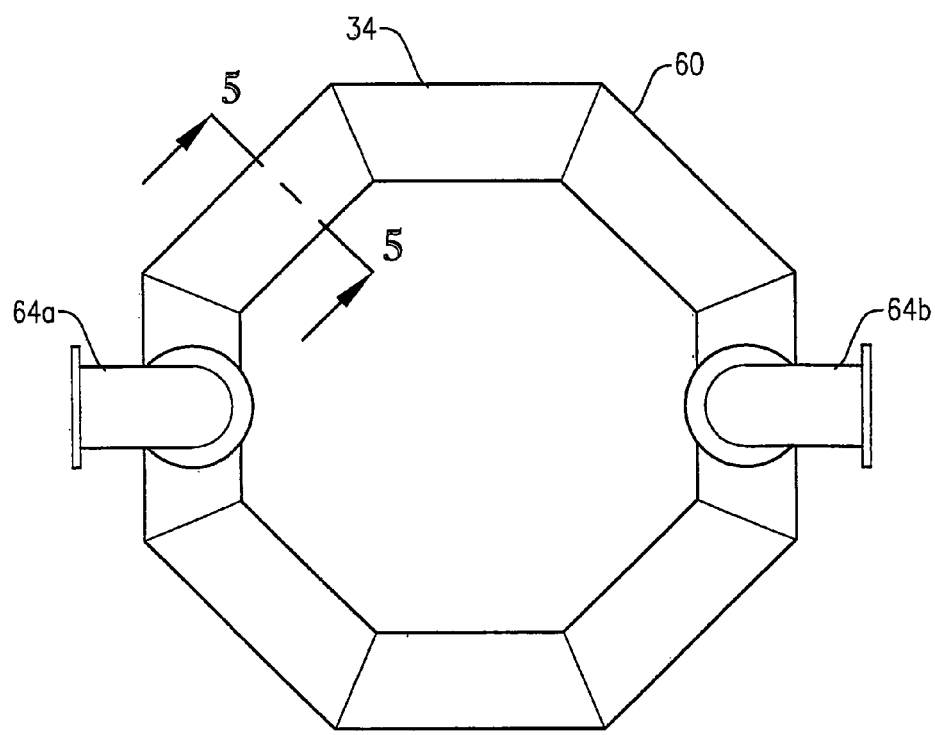
FIG. 3 is a top view of the oxidant sparger of FIG. 2, particularly illustrating that there are no oxidant discharge openings in the top of the oxidant sparger.

Referring now to FIGS. 1-5, the location and configuration of oxidant sparger 34 will now be discussed in greater detail. FIGS. 2 and 3 show that oxidant sparger 34 can include a ring member 60 and a pair of oxidant entry conduits 64a,b. Conveniently, these oxidant entry conduits 64a,b can enter the vessel at an elevation above the ring member 60 and then turn downwards as shown in FIG. 2. Alternatively, an oxidant entry conduit may enter the vessel below the ring member 60 or on about the same horizontal plane as ring member 60. Each oxidant entry conduit 64a,b includes a first end coupled to a respective oxidant inlet 66a,b formed in the vessel shell 22 and a second end fluidly coupled to ring member 60. Ring member 60 is preferably formed of conduits, more preferably of a plurality of straight conduit sections, and most preferably a plurality of straight pipe sections, rigidly coupled to one another to form a tubular polygonal ring. Preferably, ring member 60 is formed of at least 3 straight pipe sections, more preferably 6 to 10 pipe sections, and most preferably 8 pipe sections. Accordingly, when ring member 60 is formed of 8 pipe sections, it has a generally octagonal configuration. It is preferred for the pipe sections that make up oxidant entry conduits 64a,b and ring member 60 to have a nominal diameter greater than about 0.1 meter, more preferable in the range of from about 0.2 to about 2 meters, and most preferably in the range of from 0.25 to 1 meters. As perhaps best illustrated in FIG. 3, it is preferred that substantially no openings are formed in the upper portion of sparger ring 60.

Figure 4:
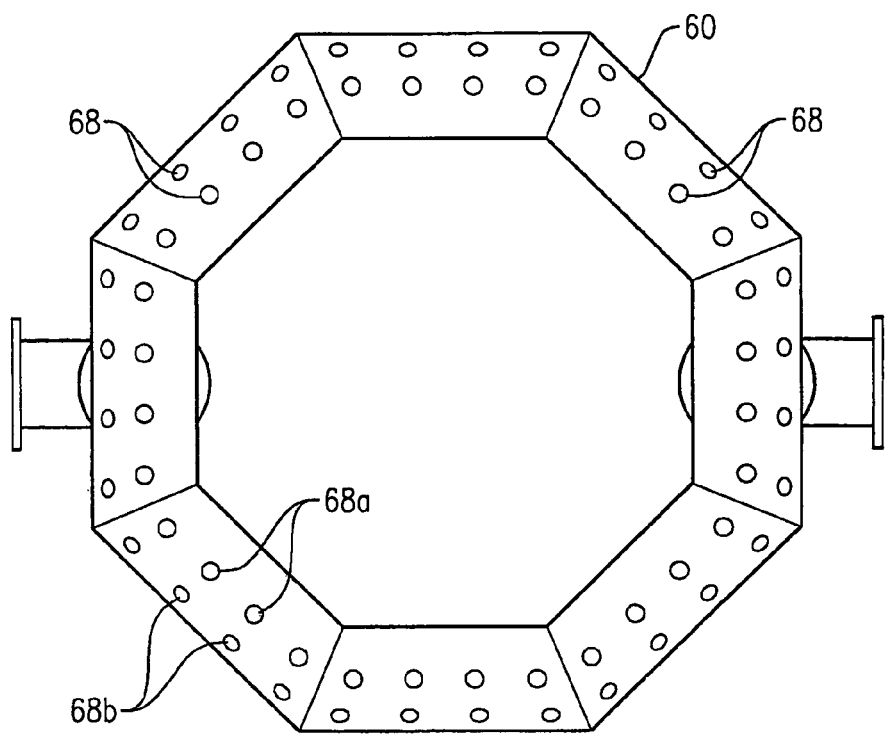
FIG. 4 is a bottom view of the oxidant sparger of FIG. 2, particularly illustrating the oxidant discharge openings in the bottom of the oxidant sparger.
Figure 5:
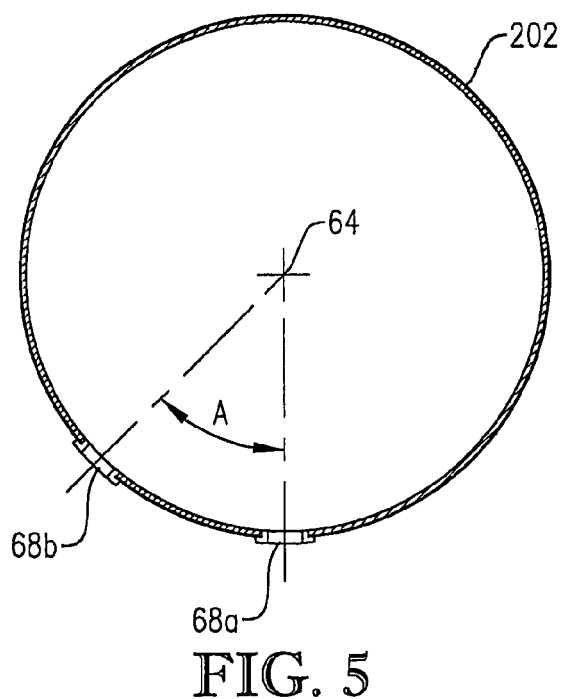
FIG. 5 is a sectional side view of the oxidant sparger taken along line 5-5 in FIG. 3, particularly illustrating the orientation of the oxidant discharge openings in the bottom of the oxidant sparger.

As perhaps best illustrated in FIGS. 4 and 5, the bottom portion of oxidant sparger ring 60 presents a plurality of oxidant openings 68. Oxidant openings 68 are preferably configured such that at least about 1 percent of the total open area defined by oxidant openings 68 is located below the centerline 64 (FIG. 5) of ring member 60, where centerline 64 is located at the elevation of the volumetric centroid of ring member 60. More preferably, at least about 5 percent of the total open area defined by all oxidant openings 68 is located below centerline 64, with at least about 2 percent of the total open area being defined by openings 68 that discharge the oxidant stream in a generally downward direction within about 30 degrees of vertical. Still more preferably, at least about 20 percent of the total open area defined by all oxidant openings 68 is located below centerline 64, with at least about 10 percent of the total open area being defined by openings 68 that discharge the oxidant stream in a generally downward direction within 30 degrees of vertical. Most preferably, at least about 75 percent of the total open area defined by all oxidant openings 68 is located below centerline 64, with at least about 40 percent of the total open area being defined by openings 68 that discharge the oxidant stream in a generally downward direction within 30 degrees of vertical. The fraction of the total open area defined by all oxidant openings 68 that are located above centerline 64 is preferably less than about 75 percent, more preferably less than about 50 percent, still more preferably less than about 25 percent, and most preferably less than 5 percent.

As illustrated in FIGS. 4 and 5, oxidant openings 68 include downward openings 68a and skewed openings 68b. Downward openings 68a are configured to discharge the oxidant stream generally downwardly at an angle within about 30 degrees of vertical, more preferably within about 15 degrees of vertical, and most preferably within 5 degrees of vertical. Referring now to FIG. 5, skewed openings 68b are configured to discharge the oxidant stream generally outwardly and downwardly at an angle "A" that is in the range of from about 15 to about 75 degrees from vertical, more preferably angle A is in the range of from about 30 to about 60 degrees from vertical, and most preferably angle A is in the range of from 40 to 50 degrees from vertical.

It is preferred for substantially all oxidant openings 68 to have approximately the same diameter. The diameter of oxidant openings 68 is preferably in the range of from about 2 to about 300 millimeters, more preferably in the range of from about 4 to about 120 millimeters, and most preferably in the range of from 8 to 60 millimeters. The total number of oxidant openings 68 in ring member 60 is selected to meet the low pressure drop criteria detailed below. Preferably, the total number of oxidant openings 68 formed in ring member 60 is at least about 10, more preferably the total number of oxidant openings 68 is in the range of from about 20 to about 200, and most preferably the total number of oxidant openings 68 is in the range of from 40 to 100.

Although FIGS. 1-5 illustrate a very specific configuration for oxidant sparger 34, it is now noted that a variety of oxidant sparger configurations can be employed to achieve the advantages described herein. For example, an oxidant sparger does not necessarily need to have the octagonal ring member configuration illustrated in FIGS. 1-5. Rather, it is possible for an oxidant sparger to be formed of any configuration of flow conduit(s) that employs a plurality of spaced-apart openings for discharging the oxidant stream. The size, number, and discharge direction of the oxidant openings in the flow conduit are preferably within the ranges stated above. Further, the oxidant sparger is preferably configured to provide the azimuthal and radial distribution of molecular oxygen described above.

Regardless of the specific configuration of oxidant sparger 34, it is preferred for the oxidant sparger to be physically configured and operated in a manner that minimizes the pressure drop associated with discharging the oxidant stream out of the flow conduit(s), through the oxidant openings, and into the reaction zone. Such pressure drop is calculated as the time-averaged static pressure of the oxidant stream inside the flow conduit at oxidant inlets 66a,b of the oxidant sparger minus the time-averaged static pressure in the reaction zone at the elevation where one-half of the oxidant stream is introduced above that vertical location and one-half of the oxidant stream is introduced below that vertical location. In a preferred embodiment of the present invention, the time-averaged pressure drop associated with discharging the oxidant stream from the oxidant sparger is less than about 0.3 megapascal (MPa), more preferably less than about 0.2 MPa, still more preferably less than about 0.1 MPa, and most preferably less than 0.05 MPa.

Optionally, a continuous or intermittent flush can be provided to oxidant sparger 34 with a liquid (e.g., acetic acid, water, and/or para-xylene) to prevent fouling of the oxidant sparger with solids. When such a liquid flush is employed, it is preferred for an effective amount of the liquid (i.e., not just the minor amount of liquid droplets that might naturally be present in the oxidant stream) to be passed through the oxidant sparger and out of the oxidant openings for at least one period of more than one minute each day. When a liquid is continuously or periodically discharged from oxidant sparger 34, it is preferred for the time-averaged ratio of the mass flow rate of the liquid through the oxidant sparger to the mass flow rate of the molecular oxygen through the oxidant sparger to be in the range of from about 0.05:1 to about 30:1, or in the range of from about 0.1:1 to about 2:1, or even in the range of from 0.2:1 to 1:1.

In many conventional bubble column reactors containing a multi-phase reaction medium, substantially all of the reaction medium located below the oxidant sparger (or other mechanism for introducing the oxidant stream into the reaction zone) has a very low gas hold-up value. As known in the art, "gas hold-up" is simply the volume fraction of a multi-phase medium that is in the gaseous state. Zones of low gas hold-up in a medium can also be referred to as "unaerated" zones. In many conventional slurry bubble column reactors, a significant portion of the total volume of the reaction medium is located below the oxidant sparger (or other mechanism for introducing the oxidant stream into the reaction zone). Thus, a significant portion of the reaction medium present at the bottom of conventional bubble column reactors is unaerated.

It has been discovered that minimizing the amount of unaerated zones in a reaction medium subjected to oxidization in a bubble column reactor can minimize the generation of certain types of undesirable impurities. Unaerated zones of a reaction medium contain relatively few oxidant bubbles. This low volume of oxidant bubbles reduces the amount of molecular oxygen available for dissolution into the liquid phase of the reaction medium. Thus, the liquid phase in an unaerated zone of the reaction medium has a relatively low concentration of molecular oxygen. These oxygen-starved, unaerated zones of the reaction medium have a tendency to promote undesirable side reactions, rather than the desired oxidation reaction. For example, when para-xylene is partially oxidized to form terephthalic acid, insufficient oxygen availability in the liquid phase of the reaction medium can cause the formation of undesirably high quantities of benzoic acid and coupled aromatic rings, notably including highly undesirable colored molecules known as fluorenones and anthraquinones.

In accordance with one embodiment of the present invention, liquid-phase oxidation is carried out in a bubble column reactor configured and operated in a manner such that the volume fraction of the reaction medium with low gas hold-up values is minimized. This minimization of unaerated zones can be quantified by theoretically partitioning the entire volume of the reaction medium into 2,000 discrete horizontal slices of uniform volume. With the exception of the highest and lowest horizontal slices, each horizontal slice is a discrete volume bounded on its sides by the sidewall of the reactor and bounded on its top and bottom by imaginary horizontal planes. The highest horizontal slice is bounded on its bottom by an imaginary horizontal plane and on its top by the upper surface of the reaction medium. The lowest horizontal slice is bounded on its top by an imaginary horizontal plane and on its bottom by the lower end of the vessel. Once the reaction medium has been theoretically partitioned into 2,000 discrete horizontal slices of equal volume, the time-averaged and volume-averaged gas hold-up of each horizontal slice can be determined. When this method of quantifying the amount of unaerated zones is employed, it is preferred for the number of horizontal slices having a time-averaged and volume-averaged gas hold-up less than 0.1 to be less than 30, more preferably less than 15, still more preferably less than 6, even more preferably less than 4, and most preferably less than 2. It is preferred for the number of horizontal slices having a gas hold-up less than 0.2 to be less than 80, more preferably less than 40, still more preferably less than 20, even more preferably less than 12, and most preferably less than 5. It is preferred for the number of horizontal slices having a gas hold-up less than 0.3 to be less than 120, more preferably less than 80, still more preferably less than 40, even more preferably less than 20, and most preferably less than 15.

Referring again to FIGS. 1 and 2, it has been discovered that positioning oxidant sparger 34 lower in reaction zone 28 provides several advantages, including reduction of the amount of unaerated zones in reaction medium 36. Given a height "H" of reaction medium 36, a length "L" of reaction zone 28, and a maximum diameter "D" of reaction zone 28, it is preferred for a majority (i.e., >50 percent by weight) of the oxidant stream to be introduced into reaction zone 28 within about 0.025H, 0.022L, and/or 0.25D of lower end 52 of reaction zone 28. More preferably, a majority of the oxidant stream is introduced into reaction zone 28 within about 0.02H, 0.018L, and/or 0.2D of lower end 52 of reaction zone 28. Most preferably, a majority of the oxidant stream is introduced into reaction zone 28 within 0.015H, 0.013L, and/or 0.15D of lower end 52 of reaction zone 28.

In the embodiment illustrated in FIG. 2, the vertical distance "$Y_1$" between lower end 52 of reaction zone 28 and the outlet of upper oxidant openings 68 of oxidant sparger 34 is less than about 0.25H, 0.022L, and/or 0.25D, so that substantially all of the oxidant stream enters reaction zone 28 within about 0.25H, 0.022L, and/or 0.25D of lower end 52 of reaction zone 28. More preferably, $Y_1$ is less than about 0.02H, 0.018L, and/or 0.2D. Most preferably, $Y_1$ is less than 0.015H, 0.013L, and/or 0.15D, but more than 0.005H, 0.004L, and/or 0.06D. FIG. 2 illustrates a tangent line 72 at the location where the bottom edge of cylindrical main body 46 of vessel shell 22 joins with the top edge of elliptical lower head 48 of vessel shell 22. Alternatively, lower head 48 can be of any shape, including conical, and the tangent line is still defined as the bottom edge of cylindrical main body 46. The vertical distance "$Y_2$" between tangent line 72 and the top of oxidant sparger 34 is preferably at least about 0.0012H, 0.001L, and/or 0.01D; more preferably at least about 0.005H, 0.004L, and/or 0.05D; and most preferably at least 0.01H, 0.008L, and/or 0.1D. The vertical distance "$Y_3$" between lower end 52 of reaction zone 28 and the outlet of lower oxidant openings 70 of oxidant sparger 34 is preferably less than about 0.015H, 0.013L, and/or 0.15D; more preferably less than about 0.012H, 0.01L, and/or 0.1D; and most preferably less than 0.01H, 0.008L, and/or 0.075D, but more than 0.003H, 0.002L, and/or 0.025D.

In addition to the advantages provided by minimizing unaerated zones (i.e., zones with low gas hold-up) in reaction medium 36, it has been discovered that oxidation can be enhanced by maximizing the gas hold-up of the entire reaction medium 36. Reaction medium 36 preferably has time-averaged and volume-averaged gas hold-up in the range of from about 0.4 to about 0.9, more preferably in the range of from about 0.5 to about 0.8, and most preferably in the range of from 0.55 to 0.70. Several physical and operational attributes of primary oxidation reactor 20 contribute to the high gas hold-up discussed above. For example, for a given reactor size and flow of oxidant stream, the high L:D ratio of reaction zone 28 yields a lower diameter which increases the superficial velocity in reaction medium 36 which in turn increases gas hold-up. Additionally, the actual diameter of a bubble column and the L:D ratio are known to influence the average gas hold-up even for a given constant superficial velocity. In addition, the minimization of unaerated zones, particularly in the bottom of reaction zone 28, contributes to an increased gas hold-up value. Further, the overhead pressure and mechanical configuration of the bubble column reactor can affect operating stability at the high superficial velocities and gas hold-up values disclosed herein.

Referring again to FIG. 1, it has been discovered that improved distribution of the aromatic compound (e.g., para-xylene) in reaction medium 36 can be provided by introducing the liquid-phase feed stream into reaction zone 28 at multiple vertically-spaced locations. Preferably, the liquid-phase feed stream is introduced into reaction zone 28 via at least 3 feed openings, more preferably at least 4 feed openings. As used herein, the term "feed openings" shall denote openings where the liquid-phase feed stream is discharged into reaction zone 28 for mixing with reaction medium 36. It is preferred for at least 2 of the feed openings to be vertically-spaced from one another by at least about 0.5D, more preferably at least about 1.5D, and most preferably at least 3D. However, it is preferred for the highest feed opening to be vertically-spaced from the lowest oxidant opening by not more than about 0.75H, 0.65L, and/or 8D; more preferably not more than about 0.5H, 0.4L, and/or 5D; and most preferably not more than 0.4H, 0.35L, and/or 4D.

Although it is desirable to introduce the liquid-phase feed stream at multiple vertical locations, it has also been discovered that improved distribution of the aromatic compound in reaction medium 36 is provided if the majority of the liquid-phase feed stream is introduced into the bottom half of reaction medium 36 and/or reaction zone 28. Preferably, at least about 75 weight percent of the liquid-phase feed stream is introduced into the bottom half of reaction medium 36 and/or reaction zone 28. Most preferably, at least 90 weight percent of the liquid-phase feed stream is introduced into the bottom half of reaction medium 36 and/or reaction zone 28. In addition, it is preferred for at least about 30 weight percent of the liquid-phase feed stream to be introduced into reaction zone 28 within about 1.5D of the lowest vertical location where the oxidant stream is introduced into reaction zone 28. This lowest vertical location where the oxidant stream is introduced into reaction zone 28 is typically at the bottom of oxidant sparger; however, a variety of alternative configurations for introducing the oxidant stream into reaction zone 28 are contemplated by a preferred embodiment of the present invention. Preferably, at least about 50 weight percent of the liquid-phase feed is introduced within about 2.5D of the lowest vertical location where the oxidant stream is introduced into reaction zone 28. Preferably, at least about 75 weight percent of the liquid-phase feed stream is introduced within about 5D of the lowest vertical location where the oxidant stream is introduced into reaction zone 28.

Each feed opening defines an open area through which the feed is discharged. It is preferred that at least about 30 percent of the cumulative open area of all the feed inlets is located within about 1.5D of the lowest vertical location where the oxidant stream is introduced into reaction zone 28. Preferably, at least about 50 percent of the cumulative open area of all the feed inlets is located within about 2.5D of the lowest vertical location where the oxidant stream is introduced into reaction zone 28. Preferably, at least about 75 percent of the cumulative open area of all the feed inlets is located within about 5D of the lowest vertical location where the oxidant stream is introduced into reaction zone 28.

Referring again to FIG. 1, in one embodiment of the present invention, feed inlets 32a,b,c,d are simply a series of vertically-aligned openings along one side of vessel shell 22. These feed openings preferably have substantially similar diameters of less than about 7 centimeters, more preferably in the range of from about 0.25 to about 5 centimeters, and most preferably in the range of from 0.4 to 2 centimeters. Primary oxidation reactor 20 is preferably equipped with a system for controlling the flow rate of the liquid-phase feed stream out of each feed opening. Such flow control system preferably includes an individual flow control valve 74a,b,c,d for each respective feed inlet 32a,b,c,d. In addition, it is preferred for primary oxidation reactor 20 to be equipped with a flow control system that allows at least a portion of the liquid-phase feed stream to be introduced into reaction zone 28 at an elevated inlet superficial velocity of at least about 2 meters per second, more preferably at least about 5 meters per second, still more preferably at least about 6 meters per second, and most preferably in the range of from 8 to 20 meters per second. As used herein, the term "inlet superficial velocity" denotes the time-averaged volumetric flow rate of the feed stream out of the feed opening divided by the area of the feed opening. Preferably, at least about 50 weight percent of the feed stream is introduced into reaction zone 28 at an elevated inlet superficial velocity. Most preferably, substantially all the feed stream is introduced into reaction zone 28 at an elevated inlet superficial velocity.

Figure 6:
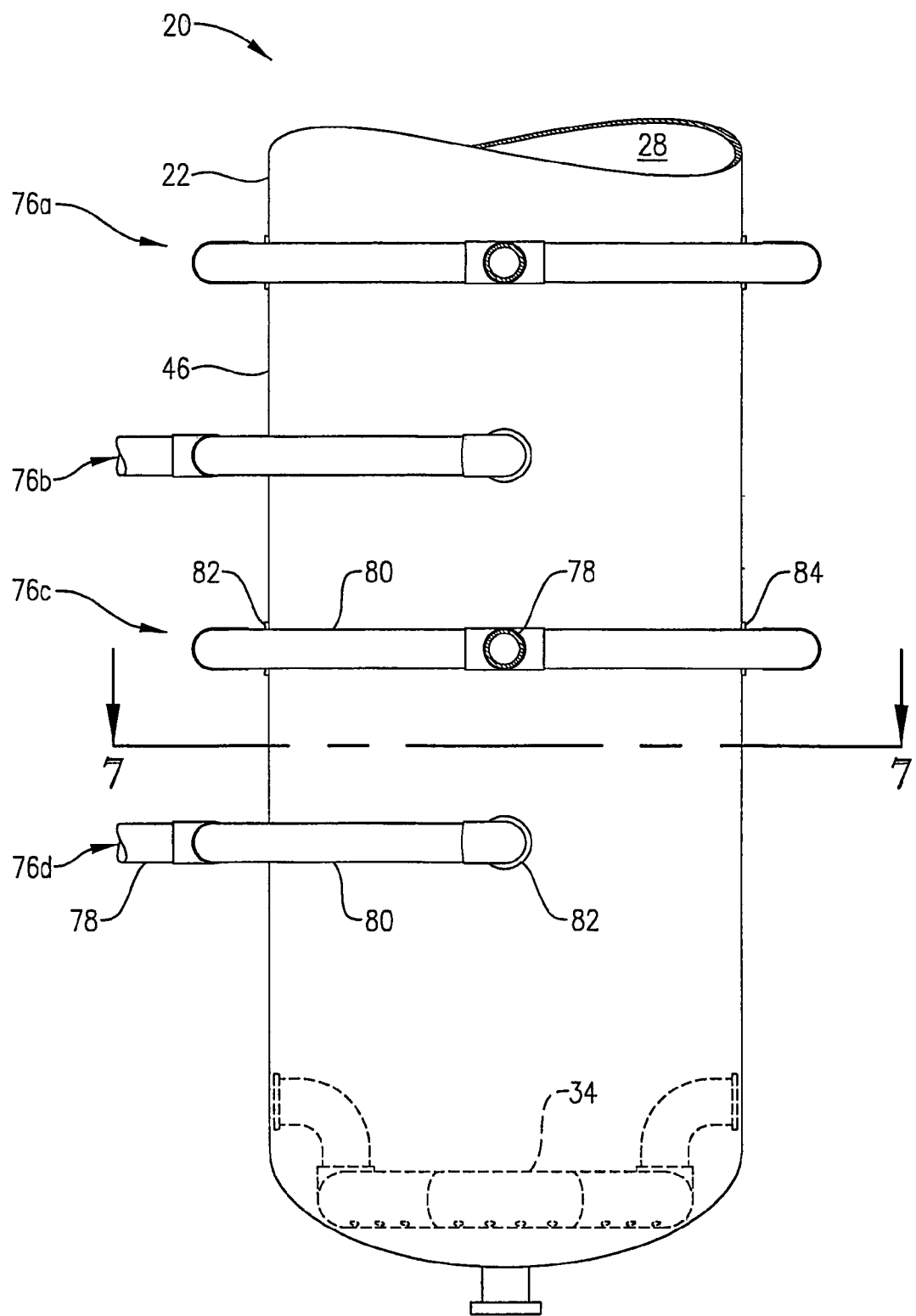
FIG. 6 is an enlarged side view of the bottom portion of the bubble column reactor, particular illustrating a system for introducing the feed stream into the reactor at multiple, vertically-space locations.
Figure 7:
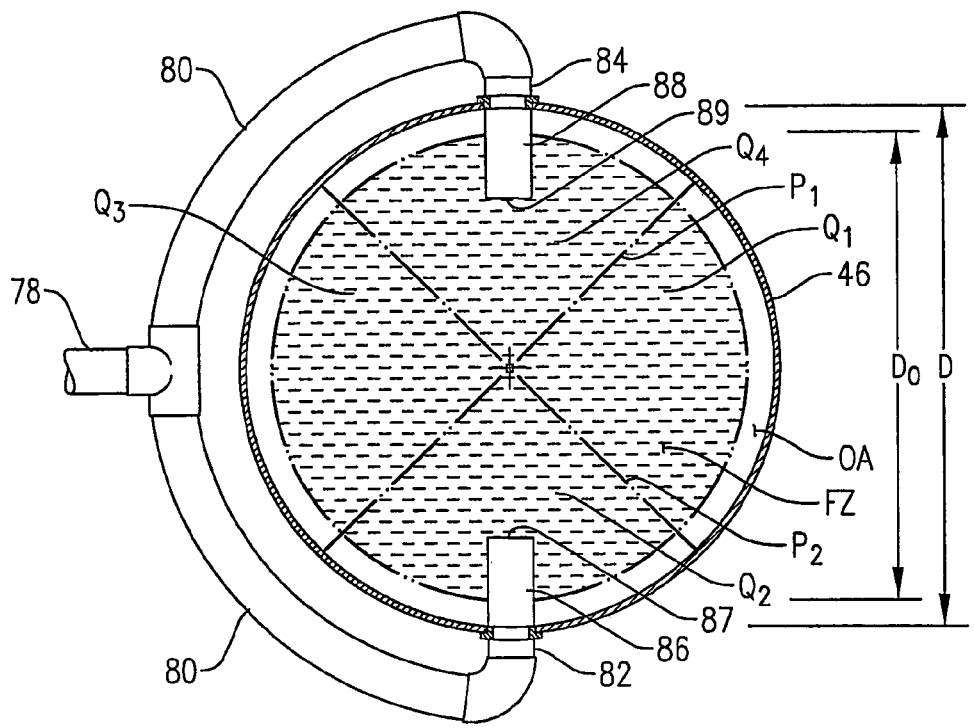
FIG. 7 is a sectional top view taken along line 7-7 in FIG. 6, particularly illustrating how the feed introduction system shown in FIG. 6 distributes the feed stream into in a preferred radial feed zone (FZ) and more than one azimuthal quadrant (Q1, Q2, Q3, Q4)

Referring now to FIGS. 6 and 7, an alternative system for introducing the liquid-phase feed stream into reaction zone 28 is illustrated. In this embodiment, the feed stream is introduced into reaction zone 28 at four different elevations. Each elevation is equipped with a respective feed distribution system 76a,b,c,d. Each feed distribution system 76 includes a main feed conduit 78 and a manifold 80. Each manifold 80 is provided with at least two outlets 82,84 coupled to respective insert conduits 86,88, which extend into reaction zone 28 of vessel shell 22. Each insert conduit 86,88 presents a respective feed opening 87,89 for discharging the feed stream into reaction zone 28. Feed openings 87,89 preferably have substantially similar diameters of less than about 7 centimeters, more preferably in the range of from about 0.25 to about 5 centimeters, and most preferably in the range of from 0.4 to 2 centimeters. It is preferred for feed openings 87,89 of each feed distribution system 76a,b,c,d to be diametrically opposed so as to introduce the feed stream into reaction zone 28 in opposite directions. Further, it is preferred for the diametrically opposed feed openings 86,88 of adjacent feed distribution systems 76 to be oriented at 90 degrees of rotation relative to one another. In operation, the liquid-phase feed stream is charged to main feed conduit 78 and subsequently enters manifold 80. Manifold 80 distributes the feed stream evenly for simultaneous introduction on opposite sides of reactor 20 via feed openings 87,89.

Figure 8:
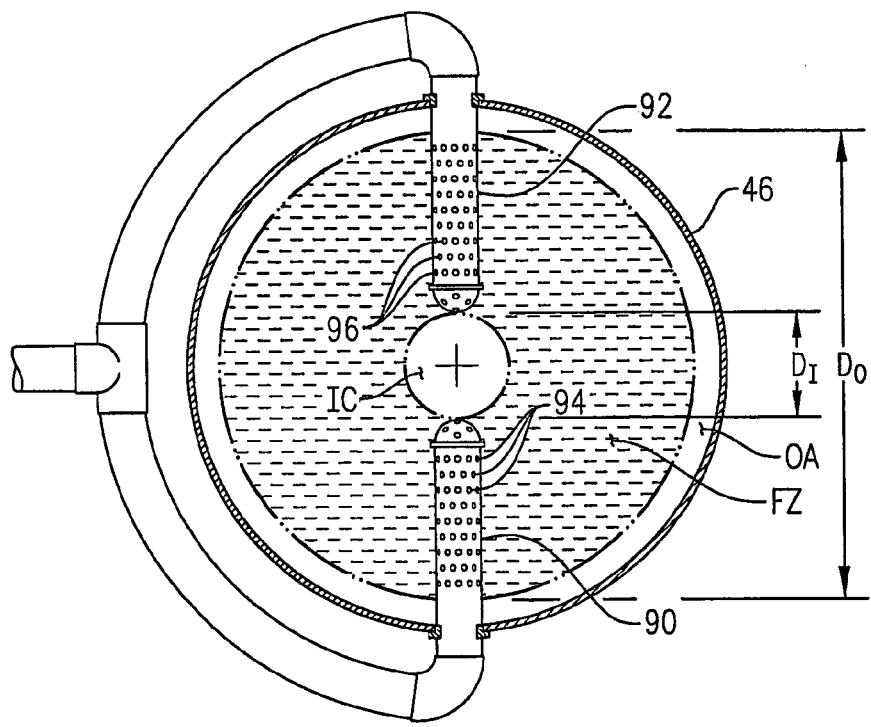
FIG. 8 is a sectional top view similar to FIG. 7, but illustrating an alternative means for discharging the feed stream into the reactor using bayonet tubes each having a plurality of small feed openings.

FIG. 8 illustrates an alternative configuration wherein each feed distribution system 76 is equipped with bayonet tubes 90,92 rather than insert conduits 86,88 (shown in FIG. 7). Bayonet tubes 90,92 project into reaction zone 28 and include a plurality of small feed openings 94,96 for discharging the liquid-phase feed into reaction zone 28. It is preferred for the small feed openings 94,96 of bayonet tubes 90,92 to have substantially the same diameters of less than about 50 millimeters, more preferably about 2 to about 25 millimeters, and most preferably 4 to 15 millimeters.

Figure 9:
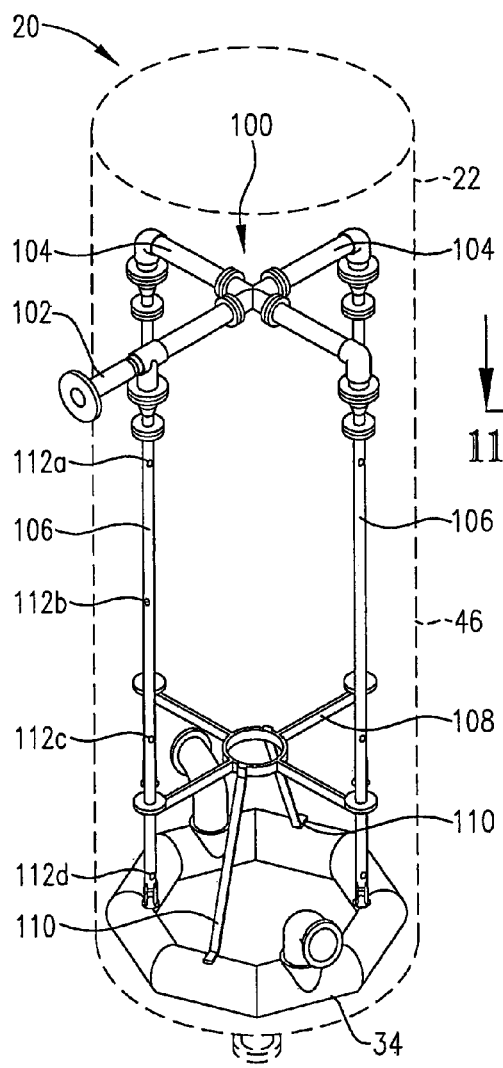
FIG. 9 is an isometric view of an alternative system for introducing the feed stream into the reaction zone at multiple vertically-space locations without requiring multiple vessel penetrations, particularly illustrating that the feed distribution system can be at least partly supported on the oxidant sparger.
Figure 11:
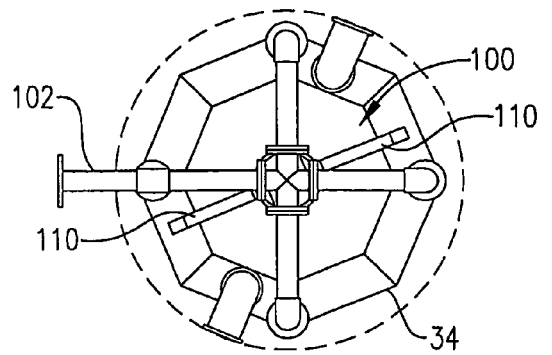
FIG. 11 is a sectional top view taken along line 11-11 in FIG. 10 and further illustrating the single-penetration feed distribution system supported on the oxidant sparger.
Figure 10:
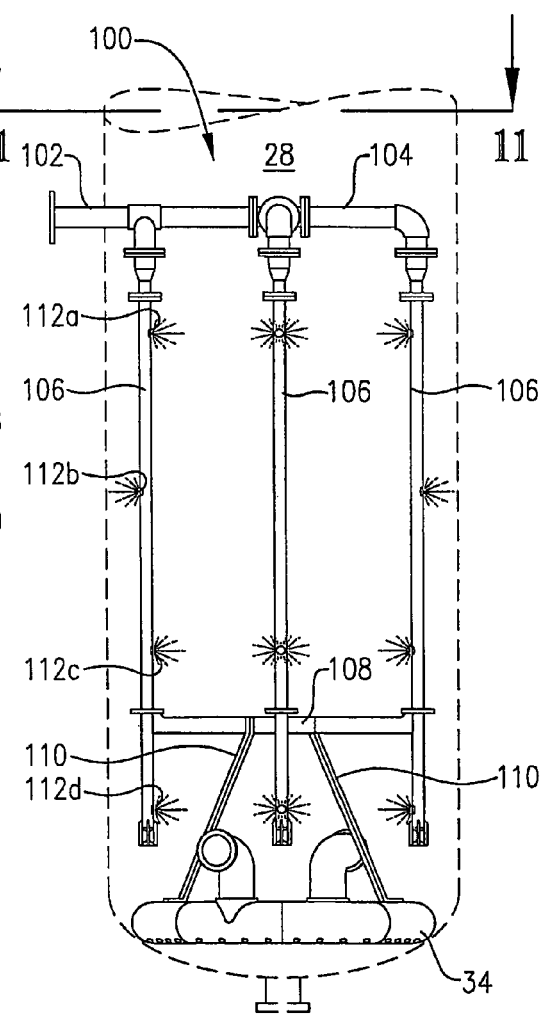
FIG. 10 is a side view of the single-penetration feed distribution system and oxidant sparger illustrated in FIG. 9.

FIGS. 9-11 illustrate an alternative feed distribution system 100. Feed distribution system 100 introduces the liquid-phase feed stream at a plurality of vertically-spaced and laterally-spaced locations without requiring multiple penetrations of the sidewall of primary oxidation reactor 20. Feed introduction system 100 generally includes a single inlet conduit 102, a header 104, a plurality of upright distribution tubes 106, a lateral support mechanism 108, and a vertical support mechanism 110. Inlet conduit 102 penetrates the sidewall of main body 46 of vessel shell 22. Inlet conduit 102 is fluidly coupled to header 104. Header 104 distributes the feed stream received from inlet conduit 102 evenly among upright distribution tubes 106. Each distribution tube 106 has a plurality of vertically-spaced feed openings 112a,b,c,d for discharging the feed stream into reaction zone 28. Lateral support mechanism 108 is coupled to each distribution tube 106 and inhibits relative lateral movement of distribution tubes 106. Vertical support mechanism 110 is preferably coupled to lateral support mechanism 108 and to the top of oxidant sparger 34. Vertical support mechanism 110 substantially inhibits vertical movement of distribution tubes 106 in reaction zone 28. It is preferred for feed openings 112 to have substantially the same diameters of less than about 50 millimeters, more preferably about 2 to about 25 millimeters, and most preferably 4 to 15 millimeters. The vertical spacing of feed openings 112 of feed distribution system 100 illustrated in FIGS. 9-11 can be substantially the same as described above with reference to the feed distribution system of FIG. 1. Optionally, feed openings can be elongated nozzles rather than simple holes. Optionally, one or more flow deflection apparatus can lie outside of the flow conduit and in path of fluids exiting therefrom into the reaction medium. Optionally, an opening near the bottom of a flow conduit can be sized to purge solids from inside the liquid-phase feed distribution system, either continuously or intermittently. Optionally, mechanical devices such as flapper assemblies, check valves, excess flow valves, power operated valves and the like may be used either to prevent ingress of solids during operational upsets or to discharge accumulated solids from within the liquid-phase feed distribution system.

It has been discovered that the flow patterns of the reaction medium in many bubble column reactors can permit uneven azimuthal distribution of the aromatic compound in the reaction medium, especially when the aromatic compound is primarily introduced along one side of the reaction medium. As used herein, the term "azimuthal" shall denote an angle or spacing around the upright axis of elongation of the reaction zone. As used herein, "upright" shall mean within 45° of vertical. In one embodiment of the present invention, the feed stream containing the aromatic compound (e.g., para-xylene) is introduced into the reaction zone via a plurality of azimuthally-spaced feed openings. These azimuthally-spaced feed openings can help prevent regions of excessively high and excessively low aromatic compound concentrations in the reaction medium. The various feed introduction systems illustrated in FIGS. 6-11 are examples of systems that provide proper azimuthal spacing of feed openings.

Referring again to FIG. 7, in order to quantify the azimuthally-spaced introduction of the liquid-phase feed stream into the reaction medium, the reaction medium can be theoretically partitioned into four upright azimuthal quadrants "$Q_1, Q_2, Q_3, Q_4$" of approximately equal volume. These azimuthal quadrants "$Q_1, Q_2, Q_3, Q_4$" are defined by a pair of imaginary intersecting perpendicular vertical planes "$P_1, P_2$" extending beyond the maximum vertical dimension and maximum radial dimension of the reaction medium. When the reaction medium is contained in a cylindrical vessel, the line of intersection of the imaginary intersecting vertical planes $P_1, P_2$ will be approximately coincident with the vertical centerline of the cylinder, and each azimuthal quadrant $Q_1, Q_2, Q_3, Q_4$ will be a generally wedge-shaped vertical volume having a height equal to the height of the reaction medium. It is preferred for a substantial portion of the aromatic compound to be discharged into the reaction medium via feed openings located in at least two different azimuthal quadrants.

In a preferred embodiment of the present invention, not more than about 80 weight percent of the aromatic compound is discharged into the reaction medium through feed openings that can be located in a single azimuthal quadrant. More preferably, not more than about 60 weight percent of the aromatic compound is discharged into the reaction medium through feed openings that can be located in a single azimuthal quadrant. Most preferably, not more than 40 weight percent of the aromatic compound is discharged into the reaction medium through feed openings that can be located in a single azimuthal quadrant. These parameters for azimuthal distribution of the aromatic compound are measured when the azimuthal quadrants are azimuthally oriented such that the maximum possible amount of aromatic compound is being discharged into one of the azimuthal quadrants. For example, if the entire feed stream is discharged into the reaction medium via two feed openings that are azimuthally spaced from one another by 89 degrees, for purposes of determining azimuthal distribution in four azimuthal quadrants, 100 weight percent of the feed stream is discharged into the reaction medium in a single azimuthal quadrant because the azimuthal quadrants can be azimuthally oriented in such a manner that both of the feed openings are located in a single azimuthal quadrant.

In addition to the advantages associated with the proper azimuthal-spacing of the feed openings, it has also been discovered that proper radial spacing of the feed openings in a bubble column reactor can also be important. It is preferred for a substantial portion of the aromatic compound introduced into the reaction medium to be discharged via feed openings that are radially spaced inwardly from the sidewall of the vessel. Thus, in one embodiment of the present invention, a substantial portion of the aromatic compound enters the reaction zone via feed openings located in a "preferred radial feed zone" that is spaced inwardly from the upright sidewalls defining the reaction zone.

Referring again to FIG. 7, the preferred radial feed zone "FZ" can take the shape of a theoretical upright cylinder centered in reaction zone 28 and having an outer diameter "$D_O$" of 0.9D, where "D" is the diameter of reaction zone 28. Thus, an outer annulus "OA" having a thickness of 0.05D is defined between the preferred radial feed zone FZ and the inside of the sidewall defining reaction zone 28. It is preferred for little or none of the aromatic compound to be introduced into reaction zone 28 via feed openings located in this outer annulus OA.

In another embodiment, it is preferred for little or none of the aromatic compound to be introduced into the center of reaction zone 28. Thus, as illustrated in FIG. 8, the preferred radial feed zone FZ can take the shape of a theoretical upright annulus centered in reaction zone 28, having an outer diameter $D_O$ of 0.9D, and having an inner diameter $D_I$ of 0.2D. Thus, in this embodiment, an inner cylinder IC having a diameter of 0.2D is "cut out" of the center of the preferred radial feed zone FZ. It is preferred for little or none of the aromatic compound to be introduced into reaction zone 28 via feed openings located in this inner cylinder IC.

In a preferred embodiment of the present invention, a substantial portion of the aromatic compound is introduced into reaction medium 36 via feed openings located in the preferred radial feed zone, regardless of whether the preferred radial feed zone has the cylindrical or annular shape described above. More preferably, at least about 25 weight percent of the aromatic compound is discharged into reaction medium 36 via feed openings located in the preferred radial feed zone. Still more preferably, at least about 50 weight percent of the aromatic compound is discharged into reaction medium 36 via feed openings located in the preferred radial feed zone. Most preferably, at least 75 weight percent of the aromatic compound is discharged into reaction medium 36 via feed openings located in the preferred radial feed zone.

Although the theoretical azimuthal quadrants and theoretical preferred radial feed zone illustrated in FIGS. 7 and 8 are described with reference to the distribution of the liquid-phase feed stream, it has been discovered that proper azimuthal and radial distribution of the gas-phase oxidant stream can also provide certain advantages. Thus, in one embodiment of the present invention, the description of the azimuthal and radial distribution of the liquid-phase feed stream, provided above, also applies to the manner in which the gas-phase oxidant stream is introduced into the reaction medium 36.

Figure 12:
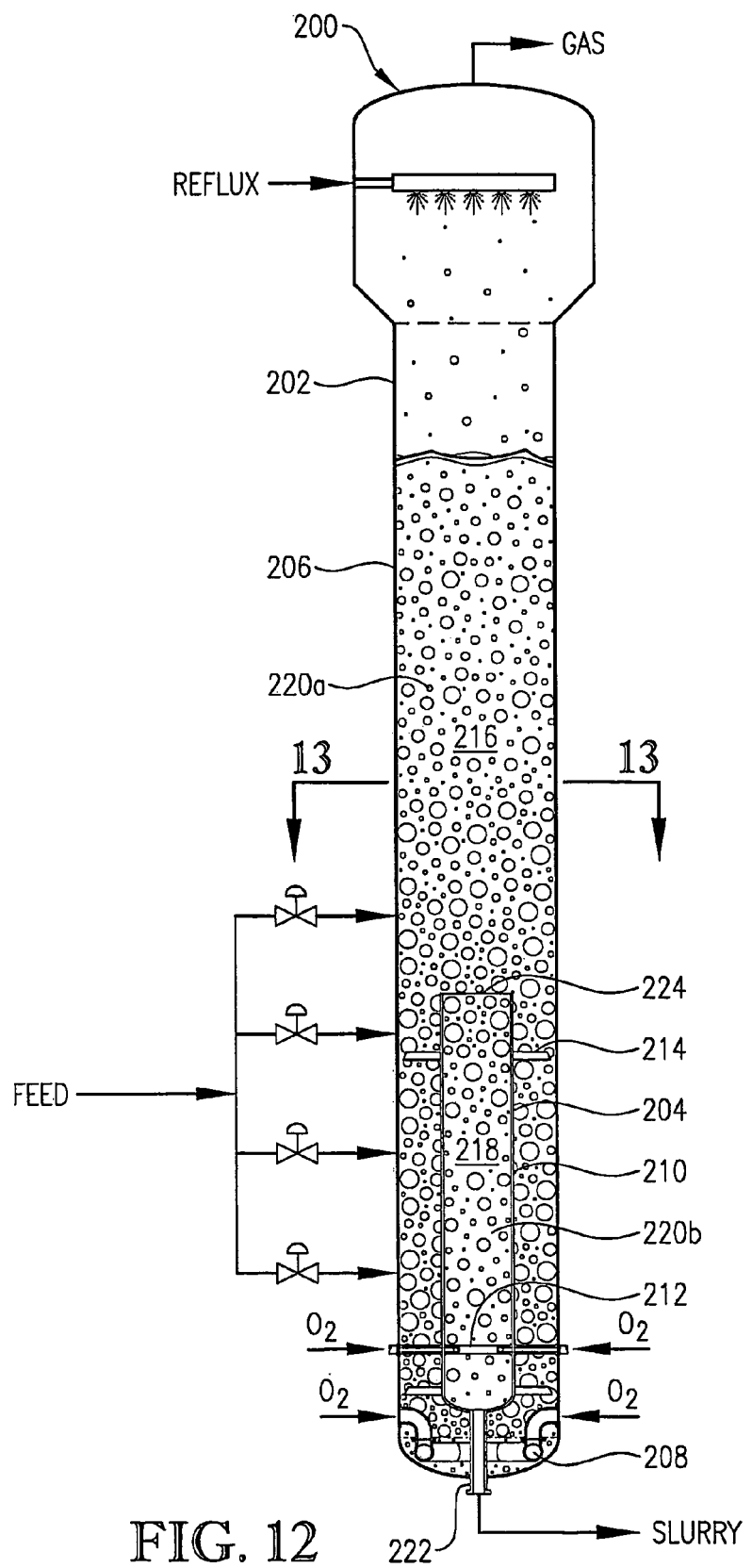
FIG. 12 is a side view of a bubble column reactor equipped with internal and external reaction vessels.
Figure 13:
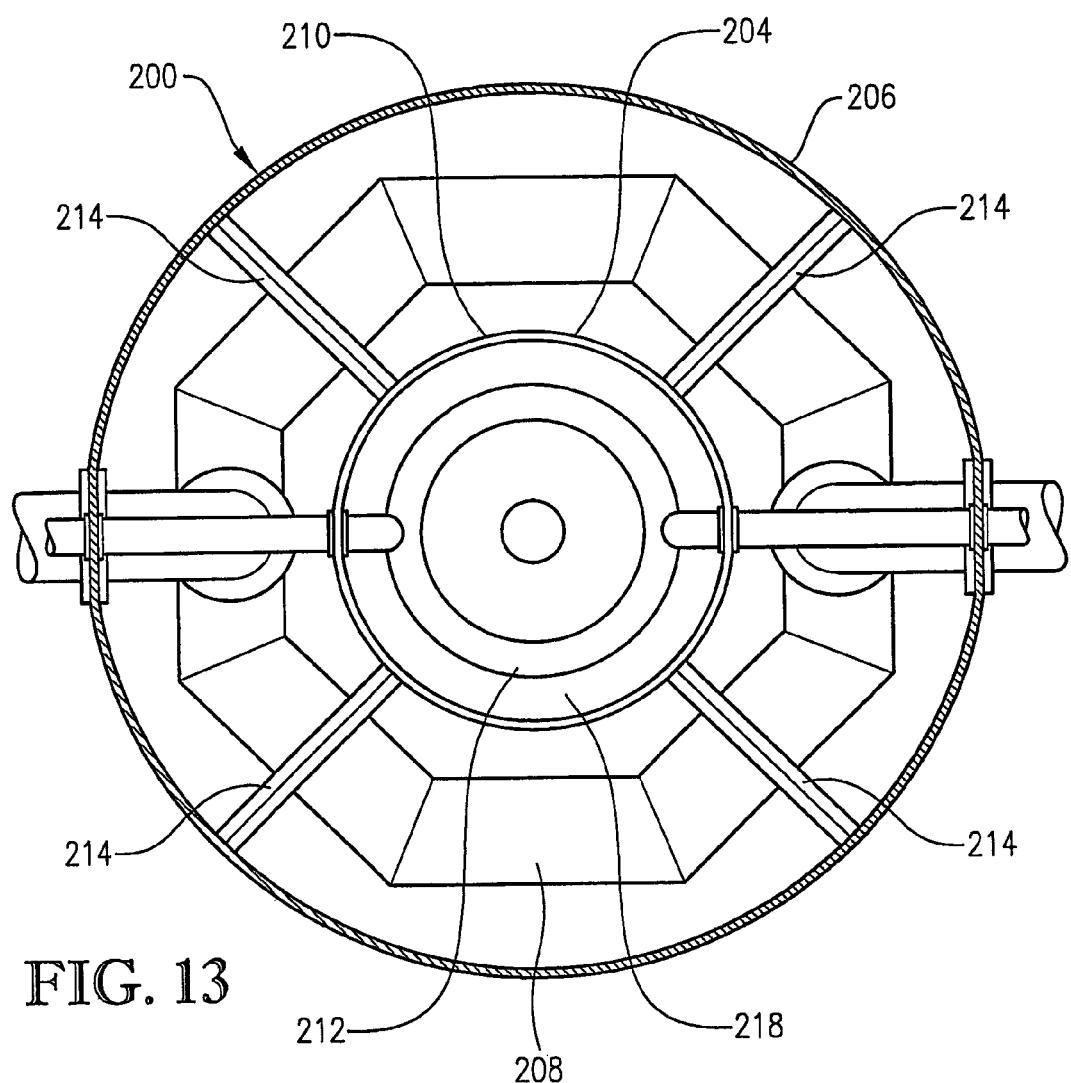
FIG. 13 is an enlarged sectional view of the bubble column reactor of FIG. 12 taken along line 13-13, particularly illustrating the relative orientation of the internal and external reaction vessels.

Referring now to FIGS. 12 and 13, there is illustrated an alternative oxidation bubble column reactor 200 having a reactor-in-reactor configuration. Oxidation reactor 200 includes an external reactor 202 and an internal reactor 204, with internal reactor 204 being at least partly disposed in external reactor 202. In a preferred embodiment, both external and internal reactors 202 and 204 are bubble column reactors. Preferably, external reactor 202 includes an external reaction vessel 206 and an external oxidant sparger 208, while internal reactor 204 includes an internal reaction vessel 210 and an internal oxidant sparger 212.

Although FIGS. 12 and 13 illustrate internal reaction vessel 210 as being fully disposed in external reaction vessel 206, it is possible for internal reaction vessel 210 to be only partial disposed in external reaction vessel 206. However, it is preferred for at least about 50, 90, 95, or 100 percent of the height of internal reaction vessel 210 to be located in external reaction vessel 206. Furthermore, it is preferred that a portion of each reaction vessel is elevated above a portion of the other reaction vessel by at least about 0.01, 0.2, 1, or 2 times the maximum diameter of the external reaction vessel.

In a preferred embodiment of the present invention, external and internal reaction vessels 206 and 210 each include a respective upright sidewall having a generally cylindrical configuration. Preferably, the upright sidewalls of external and internal reaction vessels 206 and 210 are substantially concentric and define an annulus therebetween. Internal reaction vessel 210 is supported vertically from external reaction vessel 206, preferably principally by upright supports between the lower portions of the respective vessels. In addition, internal reaction vessel 210 can be supported by external reaction vessel 206 via a plurality of lateral support members 214 extending between the upright sidewall of external and internal reaction vessels 206 and 210. Preferably, such lateral support members 214 have a non-fouling configuration with minimal upwardly-facing planar surface, as previously defined.

Although it is preferred for the upright sidewall of internal reaction vessel 210 to be substantially cylindrical, it is possible for certain portions of the upright sidewall of internal reaction vessel 210 to be concave with respect to an adjacent portion of second reaction zone 218. Preferably, any portion of the upright sidewall of internal reaction vessel 210 that is concave with respect to an adjacent portion of second reaction zone 218 accounts for less than about 25, 10, 5, or 0.1 percent of the total surface area of the upright sidewall of internal reaction vessel 210. Preferably, the ratio of the maximum height of the upright sidewall of internal reaction vessel 210 to the maximum height of the upright sidewall of external reaction vessel 206 is in the range of from about 0.1:1 to about 0.9:1, more preferably in the range of from about 0.2:1 to about 0.8:1, and most preferably in the range of from 0.3:1 to 0.7:1.

External reaction vessel 206 defines therein a first reaction zone 216, while internal reaction vessel 210 defines therein a second reaction zone 218. Preferably, external and internal reaction vessels 206 and 210 are aligned vertically such that the volumetric centroid of second reaction zone 218 is horizontally displaced from the volumetric centroid of first reaction zone 216 by less than about 0.4, 0.2, 0.1, or 0.01 times the maximum horizontal diameter of first reaction zone 216. Preferably, the ratio of the maximum horizontal cross sectional area of first reaction zone 216 to second reaction zone 218 is in the range of from about 0.01:1 to about 0.75:1, more preferably in the range of from about 0.03:1 to about 0.5:1, and most preferably in the range of from 0.05:1 to 0.3:1. Preferably, the ratio of the horizontal cross sectional area of second reaction zone 218 to the horizontal cross sectional area of the annulus defined between external and internal reaction vessels 206 and 210 is at least about 0.02:1, more preferably in the range of from about 0.05:1 to about 2:1, and most preferably in the range of from about 0.1:1 to about 1:1, where the cross sectional area is measured at ¼-height, ½-height, and/or ¾-height of second reaction zone 218. Preferably, at least about 50, 70, 90, or 100 percent of the volume of second reaction zone 218 is located in external reaction vessel 206. Preferably, the ratio of the volume of first reaction zone 216 to the volume of second reaction zone 218 is in the range of from about 1:1 to about 100:1, more preferably in the range of from about 4:1 to about 50:1, and most preferably in the range of from 8:1 to 30:1. Preferably, first reaction zone 216 has a ratio of maximum vertical height to maximum horizontal diameter in the range of from about 3:1 to about 30:1, more preferably about 6:1 to about 20:1, and most preferably in the range of from 9:1 to 15:1. Preferably, second reaction zone 218 has a ratio of maximum vertical height to maximum horizontal diameter in the range of from about 0.3:1 to about 100:1, more preferably in the range of from about 1:1 to about 50:1, and most preferably in the range of from 3:1 to 30:1. Preferably, the maximum horizontal diameter of second reaction zone 218 is in the range of from about 0.1 to about 5 meters, more preferably in the range of from about 0.3 to about 4 meters, and most preferably in the range of from 1 to 3 meters. Preferably, the maximum vertical height of second reaction zone 218 is in the range of from about 1 to about 100 meters, more preferably in the range of from about 3 to about 50 meters, and most preferably in the range of from 10 to 30 meters. Preferably, the ratio of the maximum horizontal diameter of second reaction zone 218 to the maximum horizontal diameter of first reaction zone 216 is in the range of from about 0.05:1 to about 0.8:1, more preferably in the range of from about 0.1:1 to about 0.6:1, and most preferably in the range of from 0.2:1 to 0.5:1. Preferably, the ratio of the maximum vertical height of second reaction zone 218 to the maximum vertical height of first reaction zone 216 is in the range of from about 0.03:1 to about 1:1, more preferably in the range of from about 0.1:1 to about 0.9:1, and most preferably in the range of from 0.3:1 to 0.8:1. Any parameters (e.g., height, width, area, volume, relative horizontal placement, and relative vertical placement) specified herein for external reaction vessel 206 and appurtenances are also construed as applying to first reaction zone 216 defined by external reaction vessel 206, and vice versa. Further, any parameters specified herein for internal reaction vessel 210 and appurtenances are also construed as applying to second reaction zone 218 defined by internal reaction vessel 210, and vice versa.

During operation of oxidation reactor 200, a multi-phase reaction medium 220 is first subjected to oxidation in first reaction zone 216 and then subjected to oxidation in second reaction zone 218. Thus, during normal operation, a first portion of reaction medium 220a is located in first reaction zone 216, while a second portion of reaction medium 220b is located in second reaction zone 218. After being processed in second reaction zone 218, a slurry phase (i.e., liquid and solid phases) of reaction medium 220b is withdrawn from second reaction zone 218 and discharged from oxidation reactor 200 via a slurry outlet 222 for subsequent downstream processing.

Internal reactor 204 preferably comprises at least one internal gas opening that permits additional molecular oxygen to be discharged into second reaction zone 218. Preferably, a plurality of internal gas openings are defined by internal oxidant sparger 212. The disclosures for oxidant sparger 34 of FIGS. 1-5 also apply to internal oxidant sparger 212 for conduit sizes and configurations, opening sizing and configuration, operating pressure drop, and liquid flushing. In notable distinction, it is preferable to locate oxidant sparger 212 relatively higher in order to use a lower portion of internal reaction vessel 210 as a deaeration zone. For example, embodiments disclosed herein for oxidation of para-xylene to form TPA provide a greatly diminished space time reaction rate near the bottom of second reaction zone 218, and this mitigates the effects of deaeration on impurity formation. Internal reaction vessel 210 has a maximum height "$H_i$". It is preferred for at least about 50, 75, 95, or 100 percent of the total open area defined by all of the internal gas openings to be spaced at least $0.05H_i$, $0.1H_i$, or $0.25H_i$ from the top of internal reaction vessel 210. It is also preferred for at least about 50, 75, 95, or 100 percent of the total open area defined by all of the internal gas openings to be spaced less than about $0.5H_i$, $0.25H_i$, or $0.1H_i$ above the bottom of internal reaction vessel 210. Preferably, at least about 50, 75, 95, or 100 percent of the total open area defined by all of the internal gas openings are spaced at least about 1, 5, or 10 meters from the top of internal reaction vessel 210 and at least about 0.5, 1, or 2 meters from the bottom of internal reaction vessel 210. It is preferred for at least about 50, 75, 95, or 100 percent of the total open area defined by all of the internal gas openings to communicate directly with second reaction zone 218 and not communicate directly with first reaction zone 216. As used herein, the term "open area" denotes the minimum surface area (planar or nonplanar) that would close off an opening.

In general, the manner in which the feed, oxidant, and reflux streams are introduced into external reactor 202 and the manner in which external reactor 202 is operated are substantially the same as described above with reference to primary oxidation reactor 20 of FIGS. 1-11. However, one difference between external reactor 202 (FIGS. 12 and 13) and primary oxidation reactor 20 (FIGS. 1-11) is that external reactor 202 does not include an outlet that permits the slurry phase of reaction medium 220a to be directly discharged from external reaction vessel 206 for downstream processing. Rather, oxidation reactor 200 requires the slurry phase of reaction medium 220a to first pass through internal reactor 204 before being discharged from oxidation reactor 200. As mentioned above, in second reaction zone 218 of internal reactor 204, reaction medium 220b is subjected to further oxidation to help purify the liquid and/or solid phases of reaction medium 220b.

In a process wherein para-xylene is fed to reaction zone 216, the liquid phase of reaction medium 220a that exits first reaction zone 216 and enters second reaction zone 218 typically contains at least some para-toluic acid. It is preferred for a substantial portion of the para-toluic acid entering second reaction zone 218 to be oxidized in second reaction zone 218. Thus, it is preferred for the time-averaged concentration of para-toluic acid in the liquid phase of reaction medium 220b exiting second reaction zone 218 to be less than the time-averaged concentration of para-toluic acid in the liquid phase of reaction medium 220a/b entering second reaction zone 218. Preferably, the time-averaged concentration of para-toluic acid in the liquid phase of reaction medium 220b exiting second reaction zone 218 is less than about 50, 10, or 5 percent of the time-averaged concentration of para-toluic acid in the liquid phase of reaction medium 220a/b entering second reaction zone 218. Preferably, the time-averaged concentration of para-toluic acid in the liquid phase of reaction medium 220a/b entering second reaction zone 218 is at least about 250 ppmw, more preferably in the range of from about 500 to about 6,000 ppmw, and most preferably in the range of from 1,000 to 4,000 ppmw. Preferably, the time-averaged concentration of para-toluic acid in the liquid phase of reaction medium 220b exiting second reaction zone 218 is less than about 1,000, 250, or 50 ppmw.

Internal reaction vessel 210 is equipped with at least one direct opening that permits reaction medium 220a/b to pass directly between reaction zone 216 and second reaction zone 218. It is preferred for substantially all of the direct openings in internal reaction vessel 210 to be located near the top of internal reaction vessel 210. Preferably, at least about 50, 75, 90, or 100 percent of the total open area defined by all of the direct openings is spaced less than about $0.5H_i$, $0.25H_i$, or $0.1H_i$ from the top of internal reaction vessel 210. Preferably, less than about 50, 25, 10, or 1 percent of the total open area defined by the direct openings in internal reaction vessel 210 is spaced more than about $0.5H_i$, $0.25H_i$, or $0.1H_i$ from the top of internal reaction vessel 210. Most preferably, the direct opening defined by internal reaction vessel 210 is a single upper opening 224 located at the upper-most end of internal reaction vessel 210. The ratio of the open area of upper opening 224 to the maximum horizontal cross sectional area of second reaction zone 218 is preferably at least about 0.1:1, 0.2:1, or 0.5:1.

During normal operation of oxidation reactor 200, reaction medium 220 passes from first reaction zone 216, through the direct opening(s) (e.g., upper opening 224) in internal reaction vessel 210, and into second reaction zone 218. In second reaction zone 218, the slurry phase of reaction medium 220b travels in a generally downward direction through second reaction zone 218, while the gas phase of reaction medium 220b travels in a generally upward direction. Preferably, internal reaction vessel 210 defines at least one discharge opening that permits the slurry phase to exit second reaction zone 218. The slurry phase exiting the discharge opening of internal reaction vessel 210 then exits oxidation reactor 200 via slurry outlet 222. Preferably, discharge opening is located at or near the bottom of internal reaction vessel 210. Preferably at least about 50, 75, 90, or 100 percent of the total open area defined by all discharge openings in internal reaction vessel 210 is located within about $0.5H_i$, $0.25H_i$, or $0.1H_i$ of the bottom of internal reaction vessel 210.

As reaction medium 220b is processed in second reaction zone 218 of internal reactor 204, it is preferred for the gas hold-up of reaction medium 220b to decrease as the slurry phase of reaction medium 220b flows downwardly through second reaction zone 218. Preferably, the ratio of the time-averaged gas hold-up of reaction medium 220a/b entering second reaction zone 218 to reaction medium 220b exiting second reaction zone 218 is at least about 2:1, 10:1, or 25:1. Preferably, the time-averaged gas hold-up of reaction medium 220a/b entering second reaction zone 218 is in the range of from about 0.4 to about 0.9, more preferably in the range of from about 0.5 to about 0.8, and most preferably in the range of from 0.55 to 0.7. Preferably, the time-averaged gas hold-up of reaction medium 220b exiting second reaction zone 218 is less than about 0.1, 0.05, or 0.02. Preferably, the ratio of the time-averaged gas hold-up of reaction medium 220a in first reaction zone 216 to reaction medium 220b in second reaction zone 218 is greater than about 1:1, more preferably in the range of from about 1.25:1 to about 5:1, and most preferably in the range of from 1.5:1 to 4:1, where the gas hold-up values are measured at any height of first and second reaction zones 216 and 218, at any corresponding heights of first and second reaction zones 216 and 218, at ¼-height of first and/or second reaction zones 216 and 218, at ½-height of first and/or second reaction zones 216 and 218, at ¾-height of first and/or second reaction zones 216 and 218, and/or are average values over the entire heights of first and/or second reaction zones 216 and 218. Preferably, the time-averaged gas hold-up of the portion of reaction medium 220a in first reaction zone 216 is in the range of from about 0.4 to about 0.9, more preferably in the range of from about 0.5 to about 0.8, and most preferably in the range of from 0.55 to 0.70, where the gas hold-up is measured at any height of first reaction zone 216, at ¼-height of first reaction zone 216, at ½-height of first reaction zone 216, at ¾-height of first reaction zone 216, and/or is an average over the entire height of first reaction zone 216. Preferably, the time-averaged gas hold-up of the portion of reaction medium 220b in second reaction zone 218 is in the range of from about 0.01 to about 0.6, more preferably in the range of from about 0.03 to about 0.3, and most preferably in the range of from 0.08 to 0.2, where the gas hold-up is measured at any height of second reaction zone 218, at ¼-height of second reaction zone 218, and ½-height of second reaction zone 218, at ¾-height of second reaction zone 218, and/or is an average over the entire height of second reaction zone 218.

The temperature of reaction medium 220 is preferably approximately the same in first and second reaction zones 216 and 218. Preferably, such temperature is in the range of from about 125 to about 200° C., more preferably in the range of from about 140 to about 180° C., and most preferably in the range of from 150 to 170° C. However, temperature differences preferably are formed within first reaction zone 216 that are the same as disclosed herein with reference to FIG. 28. Preferably, temperature differences of the same magnitudes also exist within second reaction zone 218 and also between first reaction zone 216 and second reaction zone 218. These additional temperature gradients relate to chemical reaction occurring in second reaction zone 218, the introduction additional oxidant to second reaction zone 218, and the static pressures extant in second reaction zone 218 compared to those in first reaction zone 216. As disclosed above, the bubble hold-up is preferably greater in first reaction zone 216 than in second reaction zone 218. Thus, at elevations below upper opening 224, the static pressure in reaction zone 216 is greater than in second reaction zone 218. The magnitude of this pressure difference depends on the magnitude of liquid or slurry density and on the difference in bubble hold-up between the two reaction zones. The magnitude of this pressure difference increases at elevations further below upper opening 224.

In one embodiment of the present invention, a portion of the aromatic compound (e.g., para-xylene) fed to oxidation reactor 200 is introduced directly into second reaction zone 218 of internal reactor 204. However, it is preferred for at least about 90, 95, 99, or 100 mole percent of the total aromatic compound fed to oxidation reactor 200 to be introduced into first reaction zone 216 (rather than second reaction zone 218). Preferably, the molar ratio of the amount of aromatic compound introduced into first reaction zone 216 to the amount of aromatic compound introduced into second reaction zone 218 is at least about 2:1, 4:1, or 8:1.

Although FIGS. 12 and 13 depict a configuration where a portion of the total molecular oxygen fed to oxidation reactor 200 is introduced into second reaction zone 218 of internal reactor 204 via internal oxidant sparger 212, it is preferred for the majority of the total molecular oxygen fed to oxidation reactor 200 to be introduced into first reaction zone 216, with the balance being introduced into the second reaction zone 218. Preferably, at least about 70, 90, 95, or 98 mole percent of the total molecular oxygen fed to oxidation reactor 200 is introduced into first reaction zone 216. Preferably, the molar ratio of the amount of molecular oxygen introduced into first reaction zone 216 to the amount of molecular oxygen introduced into second reaction zone 218 is at least about 2:1, more preferably in the range of from about 4:1 to about 200:1, most preferably in the range of from 10:1 to 100:1. Although it is possible for some of the solvent and/or aromatic compound (e.g., para-xylene) to be fed directly to second reaction zone 218, it is preferred for less than about 10, 5, or 1 weight percent of the total amount of solvent and/or aromatic compound fed to oxidation reactor 200 to be fed directly to second reaction zone 218.

The volume, residence time, and space time rate of medium 220a in first reaction zone 216 of external reaction vessel 206 are preferably substantially greater than the volume, residence time, and space time rate of reaction medium 220b in second reaction zone 218 of internal reaction vessel 210. Therefore, the majority of the aromatic compound (e.g., para-xylene) fed to oxidation reactor 200 is preferably oxidized in first reaction zone 216. Preferably, at least about 80, 90, or 95 weight percent of all the aromatic compound that is oxidized in oxidation reactor 200 is oxidized in first reaction zone 216. It is preferred for the time-averaged superficial gas velocity of reaction medium 220a in first reaction zone 216 to be at least about 0.2, 0.4, 0.8, or 1 meters per second, where the superficial gas velocity is measured at any height of first reaction zone 216, at ¼-height of first reaction zone 216, at ½-height of first reaction zone 216, at ¾-height of first reaction zone 216, and/or is an average over the entire height of first reaction zone 216.

Although reaction medium 220b in second reaction zone 218 can have the same superficial gas velocity as reaction medium 220a in first reaction zone 216, it is preferred that the time-averaged superficial gas velocity of reaction medium 220b in second reaction zone 218 is less than the time-averaged and volume-averaged superficial gas velocity of reaction medium 220b in second reaction zone 218. This reduced superficial gas velocity in second reaction zone 218 is made possible by, for example, the reduced demand for molecular oxygen in second reaction zone 218 compared to first reaction zone 216. Preferably, the ratio of the time-averaged superficial gas velocity of reaction medium 220a in first reaction zone 216 to reaction medium 220b in second reaction zone 218 is at least about 1.25:1, 2:1, or 5:1, where the superficial gas velocities are measured at any height of first and second reaction zones 216 and 218, at any corresponding heights of first and second reaction zones 216 and 218, at ¼-height of first and/or second reaction zones 216 and 218, at ½-height of first and/or second reaction zones 216 and 218, at ¾-height of first and/or second reaction zones 216 and 218, and/or are average values over the entire heights of first and/or second reaction zones 216 and 218. Preferably, the time-averaged and volume-averaged superficial gas velocity of reaction medium 220b in second reaction zone 218 is less than about 0.2, 0.1, or 0.06 meters per second, where the superficial gas velocity is measured at any height of second reaction zone 218, at ¼-height of second reaction zone 218, at ½-height of second reaction zone 218, at ¾-height of second reaction zones 218, and/or is an average over the entire height of second reaction zone 218. With these lower superficial gas velocities, downward flow of the slurry phase of reaction medium 220b in second reaction zone 218 can be made to move directionally toward plug flow. For example, during oxidation of para-xylene to form TPA, the relative vertical gradient of liquid phase concentration of para-toluic acid can be much greater in second reaction zone 218 than in first reaction zone 216. This is notwithstanding that second reaction zone 218 is a bubble column having axial mixing of liquid and of slurry compositions. The time-averaged superficial velocity of the slurry phase (solid+liquid) and the liquid phase of reaction medium 220b in second reaction zone 218 are preferably less than about 0.2, 0.1, or 0.06 meters per second, where the superficial velocity is measured at any height of second reaction zones 218, at ¼-height of second reaction zones 218, at ½-height of second reaction zones 218, at ¾-height of second reaction zones 218, and/or is an average over the entire height of second reaction zone 218.

In one embodiment of the present invention, oxidation reactor 200 is operated in a manner that permits solids sedimentation in internal reactor 204. If solids sedimentation is desired, it is preferred for the time-averaged and volume-averaged superficial gas velocity of reaction medium 220b in second reaction zone 218 to be less than about 0.05, 0.03, or 0.01 meters per second. Further, if solids sedimentation is desired, it is preferred for the time-averaged and volume-averaged superficial velocity of the slurry and liquid phases of reaction medium 220b in second reaction zone 218 to be less than about 0.01, 0.005, or 0.001 meters per second.

While it is possible for some of the slurry phase exiting internal reactor 204 to be directly recirculated back to first reaction zone 216 without further downstream processing, it is preferred for direct recirculation of reaction medium 220b from the lower elevations of second reaction zone 218 to first reaction zone 216 to be minimized. Preferably, the mass of reaction medium 220b (solid, liquid, and gas phases) exiting the lower 25 percent of the volume of second reaction zone 218 and directly recirculated back to first reaction zone 216 without further downstream processing is less than 10, 1, or 0.1 times the mass (solid, liquid, and gas phases) of reaction medium 220b exiting second reaction zone 218 and thereafter subjected to downstream processing. Preferably, the mass of reaction medium 220b exiting the lower 50 percent of the volume of second reaction zone 218 and directly recirculated back to first reaction zone 216 without further downstream processing is less than 20, 2, or 0.2 times the mass of reaction medium 220b exiting second reaction zone 218 and thereafter subjected to downstream processing. Preferably, less than about 50, 75, or 90 weight percent of the liquid phase of reaction medium 220b exiting second reaction zone 218 via openings in the lower 90, 60, 50, or 5 percent of the volume of second reaction zone 218 is introduced into first reaction zone 216 within 60, 20, 5, or 1 minutes after exiting second reaction zone 218. Preferably, the liquid phase of reaction medium 220b located in second reaction zone 218 has a mass-averaged residence time in second reaction zone 218 of at least about 1 minute, more preferably in the range of from about 2 to about 60 minutes, and most preferably in the range of from 5 to 30 minutes. Preferably, less than about 50, 75, or 90 weight percent of the liquid phase of reaction medium 220a/b introduced into second reaction zone 218 enters second reaction zone 218 in the lower 90, 60, or 30 percent of the volume of second reaction zone 218. Preferably, less than about 50, 75, or 90 weight percent of the total liquid phase of reaction medium 220a/b introduced as a liquid-phase feed stream into first reaction zone 216 enters first reaction zone 216 within 60, 20, 5, or 1 minutes after being withdrawn from second reaction zone 218 via slurry outlet 222. Preferably, at least about 75, 90, 95, or 99 weight percent of the liquid phase of reaction medium 220b withdrawn from second reaction zone 218 exits second reaction zone 218 via openings in the lower 90, 60, 30, or 5 percent of the volume of second reaction zone 218.

The design of reactor-in-reactor oxidation reactor 200 can be varied in many ways without departing from the ambit of the present invention. For example, internal reaction vessel 210 can have a greater height than external reaction vessel 206 if internal reaction vessel 210 extends below the lower end of external reaction vessel 206. External and internal reaction vessels 206 and 210 can be cylindrical, as illustrated, or can have another shape. External and internal reaction vessels 206 and 210 need not be axisymmetric, axially vertical, or concentric. The gas phase exiting internal reactor 204 can be routed outside oxidation reactor 200 without being commingled with reaction medium 220a in first reaction zone 216. However, for flammability safety, it is desirable to limit volumes of trapped gas pockets to less than about 10, 2, or 1 cubic meters. In addition, the slurry phase exiting internal reactor 204 need not exit via a single slurry opening in the bottom of internal reaction vessel 210. The slurry phase can exit oxidation reactor 200 though a side outlet in a pressure containing sidewall of external reactor 202.

Figure 14:
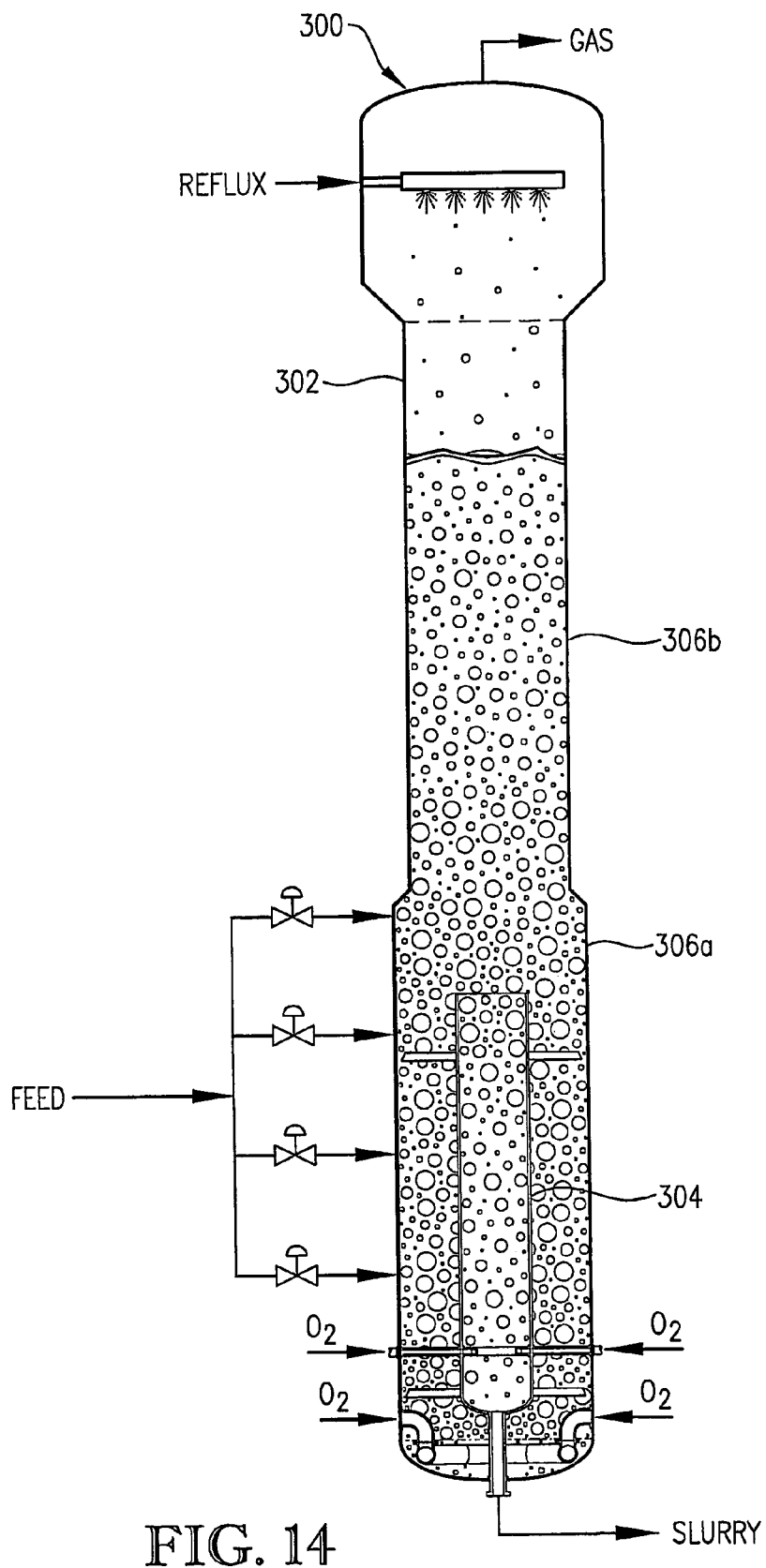
FIG. 14 is a side view of an alternative bubble column reactor equipped with internal and external reaction vessels, particularly illustrating that the external reaction vessel has a stepped diameter.

Referring now to FIG. 14, there is illustrated a oxidation reactor 300 having a reactor-in-reactor and staged-diameter configuration. Primary oxidation reactor 300 comprises an external reactor 302 and an internal reactor 304. External reactor 302 includes an external reaction vessel 306 having a broad lower section 306a and a narrow upper section 306b. Preferably, the diameter of narrow upper section 306b is smaller than the diameter of broad lower section 306a. With the exception of the staged-diameter configuration of the external reaction vessel, oxidation reactor 300 of FIG. 14 is preferably configured and operated in substantially the same manner as oxidation reactor 200 of FIGS. 12 and 13, described above.

Figure 15:
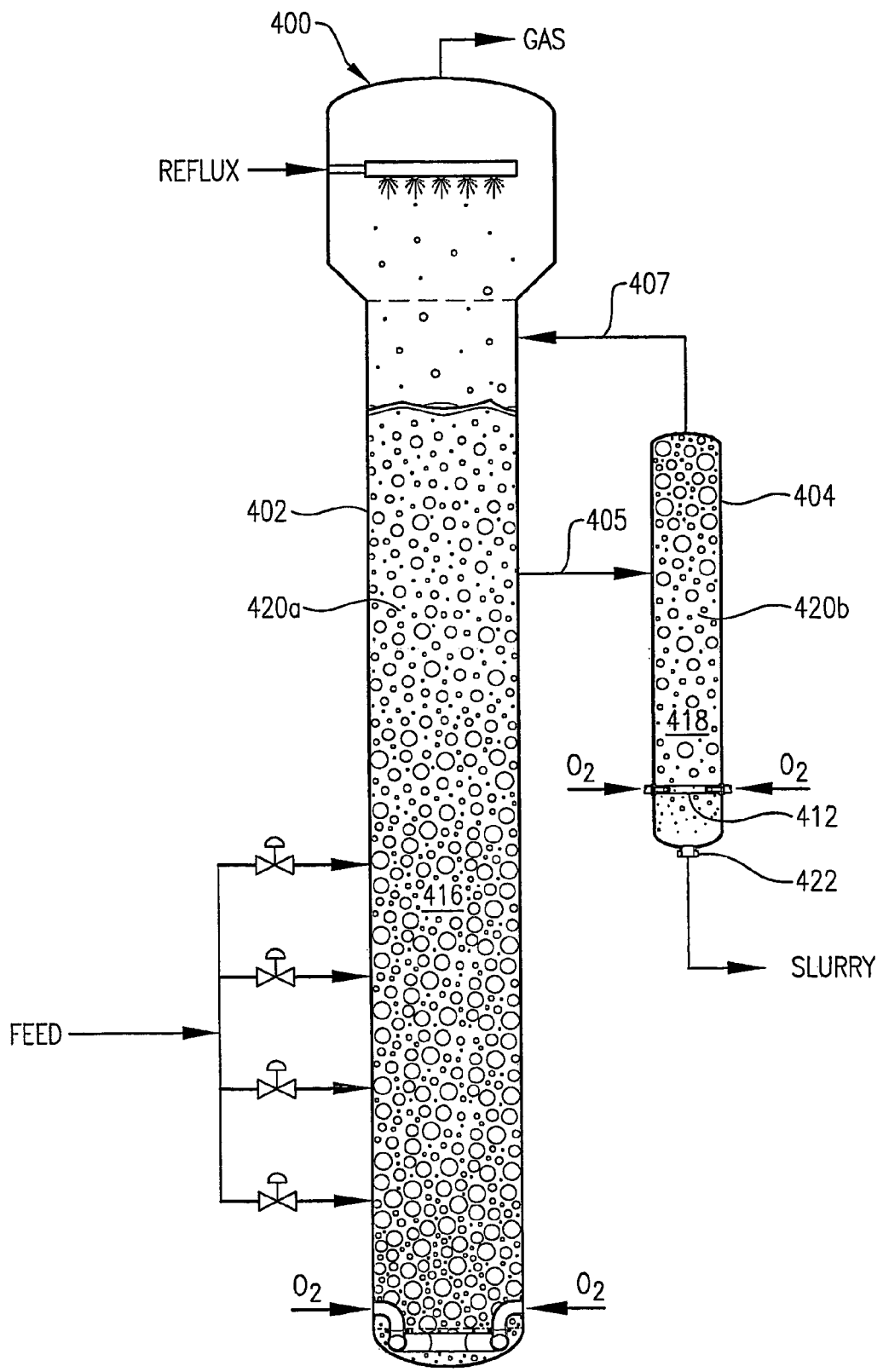
FIG. 15 is a side view of a bubble column reactor equipped with an external secondary oxidation reactor that receives a slurry from a sidedraw in the primary oxidation reactor.

Referring now to FIG. 15, there is illustrated a reactor system 400 comprising a primary oxidation reactor 402 and a secondary oxidation reactor 404. Primary oxidation reactor 402 is preferably configured and operated in substantially the same manner as external reactor 202 of FIGS. 12 and 13. Secondary oxidation reactor 404 is preferably configured and operated in substantially the same manner as internal reactor 204 of FIGS. 12 and 13. However, the main difference between reactor system 400 of FIG. 15 and oxidation reactor 200 of FIGS. 12 and 13 is that secondary oxidation reactor 404 of reactor system 400 is located outside of primary oxidation reactor 402. In reaction system 400 of FIG. 15, an inlet conduit 405 is employed to transfer a portion of the reaction medium 420 from primary oxidation reactor 402 to secondary oxidation reactor 404. Further, an outlet conduit 407 is used to transfer overhead gasses from the top of secondary oxidation reactor 404 to primary oxidation reactor 402.

During normal operation of reaction system 400, multiphase reaction medium 420 first undergoes primary oxidation in a primary reaction zone 416 of primary oxidation reactor 402. Reaction medium 420a is then withdrawn from primary reaction zone 416 and transferred to a secondary reaction zone 418 via conduit 405. In secondary reaction zone 418, the liquid and/or solid phases of reaction medium 420b are subjected to further oxidation. It is preferred for at least about 50, 75, 95, or 99 weight percent of liquid and/or solid phases withdrawn from primary reaction zone 416 to be processed in secondary reaction zone 416. Overhead gasses exit an upper gas outlet of secondary oxidation reactor 404 and are transferred back to primary oxidation reactor 402 via conduit 407. A slurry phase of reaction medium 420b exits a lower slurry outlet 422 of secondary oxidation reactor 404 and is thereafter subjected to further downstream processing.

Inlet conduit 405 may attach to primary oxidation reactor 402 at any height. Although not shown in FIG. 15, reaction medium 420 can be mechanically pumped to secondary reaction zone 418 if desired. However, it is more preferable to use elevation head (gravity) to transfer reaction medium 420 from primary reaction zone 416 through inlet conduit 405 and into secondary reaction zone 418. Accordingly it is preferable that inlet conduit 405 is connected on one end to the upper 50, 30, 20, or 10 percent of the total height and/or volume of primary reaction zone 416. Preferably, the other end of inlet conduit 405 is attached to the upper 30, 20, 10, or 5 percent of the total height and/or volume of secondary reaction zone 418. Preferably, inlet conduit 405 is horizontal and/or sloping downward from primary oxidation reactor 402 toward secondary oxidation reactor 404. Outlet conduit 407 may attach to any elevation in secondary oxidation reactor 404, but it is preferable that outlet conduit 407 is connected to secondary oxidation reactor 404 above the attachment elevation of inlet conduit 405. More preferably, outlet conduit 407 attaches to the top of secondary oxidation reactor 404. Outlet conduit 407 preferably attaches to primary oxidation reactor 402 above the attachment elevation of inlet conduit 405. More preferably, outlet conduit 407 attaches to the upper 30, 20, 10, or 5 percent of the total height and/or volume of primary reaction zone 416. Preferably, outlet conduit 407 is horizontal and/or sloping upward from reaction secondary oxidation reactor 404 toward primary oxidation reactor 402. Although not shown in FIG. 15, outlet conduit 407 may also attach directly to the gas outlet conduit that withdraws gaseous effluent from the top of primary oxidation reactor 402. The upper extent of secondary reaction zone 416 may be above or below the upper extent of primary reaction zone 418. More preferably, the upper extent of primary reaction zone 416 is within 10 meters above to 50 meters below, 2 meters below to 40 meters below, or 5 meters below to 30 meters below the upper extent of secondary reaction zone 418. Lower slurry outlet 422 may exit from any elevation of secondary oxidation reactor 404, but it is preferable that lower slurry outlet 422 is connected to secondary oxidation reactor 404 below the attachment elevation of inlet conduit 405. The attachment point of lower slurry outlet 422 is more preferably widely separated in elevation from the attachment point of inlet conduit 405, with the two attachments separated by at least about 50, 70, 90, or 95 percent of the height of secondary reaction zone 418. Most preferably, lower slurry outlet 422 attaches to the bottom of secondary oxidation reactor 404 as shown in FIG. 15. The lower extent of secondary reaction zone 418 may be elevated above or below the lower extent of primary reaction zone 416. More preferably, the lower extent of primary reaction zone 416 is elevated within about 40, 20, 5, or 2 meters above or below the lower extent of secondary reaction zone 418.

Parameters (e.g., height, width, area, volume, relative horizontal placement, and relative vertical placement) specified herein for primary oxidation reactor 402 and appurtenances are also construed as applying to primary reaction zone 416 defined by primary oxidation reactor 402, and vice versa. Any parameters specified herein for secondary oxidation reactor 404 and appurtenances are also construed as applying to secondary reaction zone 418 defined by secondary oxidation reactor 404, and vice versa.

As mentioned above, it is preferred for secondary oxidation reactor 404 to be located outside of primary oxidation reactor 402. Preferably, secondary oxidation reactor 404 is located alongside primary oxidation reactor 402 (i.e., at least a portion of primary and secondary oxidation reactors 402 and 404 share a common elevation). Primary reaction zone 416 of primary oxidation reactor 402 has a maximum diameter "$D_p$". The volumetric centroid of secondary reaction zone 418 is preferably horizontally spaced from the volumetric centroid of primary reaction zone 416 by at least about 0.5 $D_p$, 0.75 $D_p$, or 1.0 $D_p$ and by less than about 30 $D_p$, 10 $D_p$, or 3 $D_p$.

Figure 16:
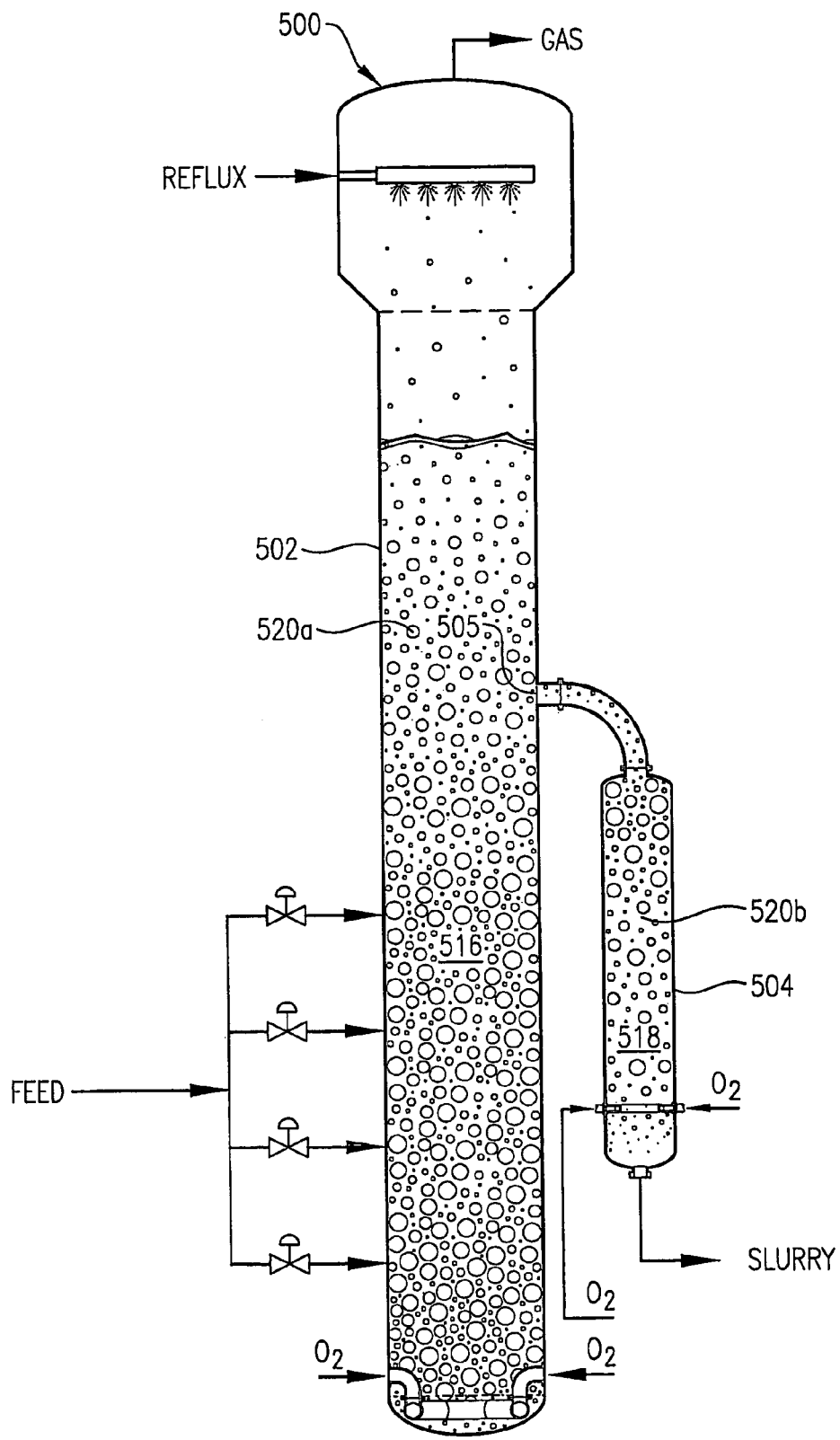
FIG. 16 is a side view of a bubble column reactor equipped with an open-ended external secondary oxidation reactor that receives slurry from an enlarged opening in the side of the primary oxidation reactor.

Referring now to FIG. 16, there is illustrated a reactor system 500 comprising a primary oxidation reactor 502 and a secondary oxidation reactor 504. Primary oxidation reactor defines therein a primary oxidation zone 516, while secondary oxidation reactor 504 defines therein a secondary oxidation zone 518. Each reaction zone 516 and 518 receives a portion of reaction medium 520.

The configuration and operation of reactor system 500 (FIG. 16) is preferably substantially the same as the configuration and of reactor system 400 (FIG. 15). However, in reactor system 500, the upright sidewall of primary oxidation reactor 502 defines at least one enlarged opening 505 that permits the transfer of reaction medium 520 from primary reaction zone 516 to secondary reaction zone 518, while simultaneously permitting the transfer of the disengaged gas phase from secondary reaction zone 518 to primary reaction zone 516. Preferably, the open area of enlarged opening 505 divided by the maximum horizontal cross sectional area of the upright portion of secondary reaction zone 218 is in the range of from about 0.01 to 2, 0.02 to 0.5, or 0.04 to 0.2. Primary reaction zone 516 of primary oxidation reactor 502 has a maximum height "$H_p$". It is preferred for the areal center of enlarged opening 505 to be vertically spaced at least about 0.1 $H_p$, 0.2 $H_p$, or 0.3 $H_p$ from the top and/or bottom of primary reaction zone 516.

Figure 17:
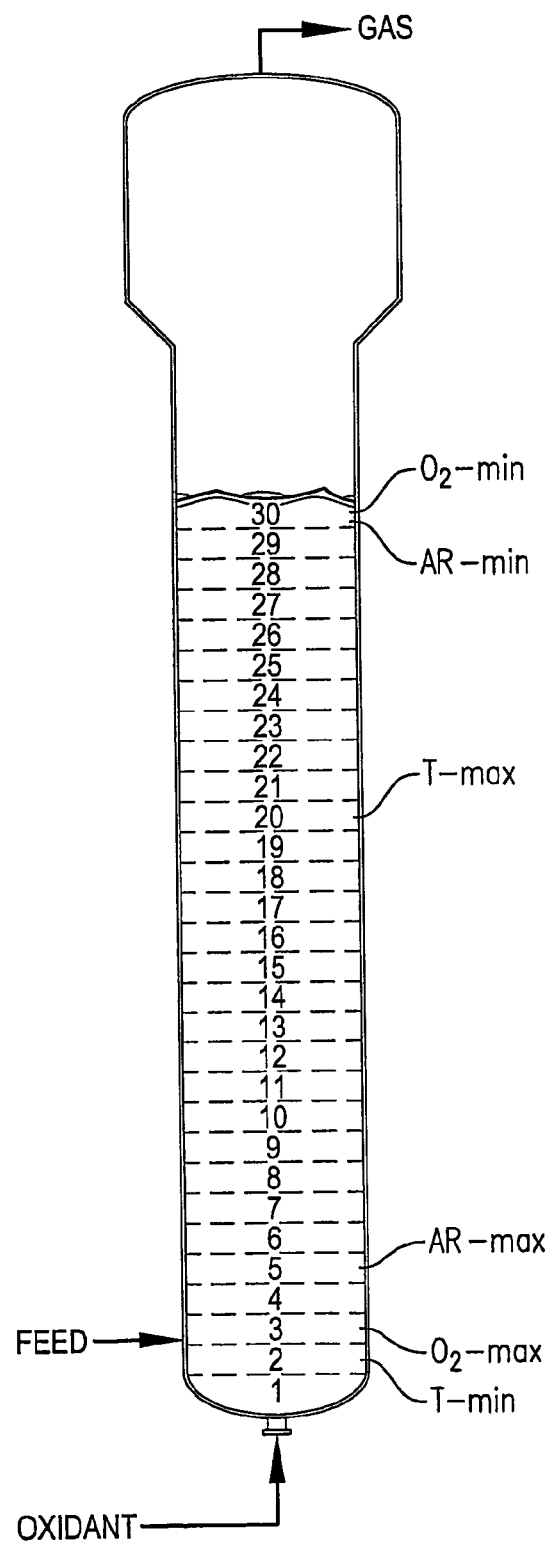
FIG. 17 is a side view of a bubble column reactor containing a multi-phase reaction medium, particularly illustrating the reaction medium being theoretically partitioned into 30 horizontal slices of equal volume in order to quantify certain gradients in the reaction medium.

Referring now to FIG. 17, in order to quantify the reactant concentration gradients existing in the primary reaction medium during oxidation in the primary oxidation reactor, the entire volume of the primary reaction medium can be theoretically partitioned into 30 discrete horizontal slices of equal volume. FIG. 17 illustrates the concept of dividing the primary reaction medium into 30 discrete horizontal slices of equal volume. With the exception of the highest and lowest horizontal slices, each horizontal slice is a discrete volume bounded on its top and bottom by imaginary horizontal planes and bounded on its sides by the wall of the reactor. The highest horizontal slice is bounded on its bottom by an imaginary horizontal plane and on its top by the upper surface of the primary reaction medium. The lowest horizontal slice is bounded on its top by an imaginary horizontal plane and on its bottom by the bottom of the vessel shell. Once the primary reaction medium has been theoretically partitioned into 30 discrete horizontal slices of equal volume, the time-averaged and volume-averaged concentration of each horizontal slice can then be determined. The individual horizontal slice having the maximum concentration of all 30 horizontal slices can be identified as the "C-max horizontal slice." The individual horizontal slice located above the C-max horizontal slice and having the minimum concentration of all horizontal slices located above the C-max horizontal slice can be identified as the "C-min horizontal slice." The vertical concentration gradient can then be calculated as the ratio of the concentration in the C-max Horizontal slice to the concentration in the C-min horizontal slice.

With respect to quantifying the oxygen concentration gradient, when the primary reaction medium is theoretically partitioned into 30 discrete horizontal slices of equal volume, an $O_2$-max horizontal slice is identified as having the maximum oxygen concentration of all the 30 horizontal slices and an $O_2$-min horizontal slice is identified as having the minimum oxygen concentration of the horizontal slices located above the $O_2$-max horizontal slice. The oxygen concentrations of the horizontal slices are measured in the gas phase of the primary reaction medium on a time-averaged and volume-averaged molar wet basis. It is preferred for the ratio of the oxygen concentration of the $O_2$-max horizontal slice to the oxygen concentration of the $O_2$-min horizontal slice to be in the range of from about 2:1 to about 25:1, more preferably in the range of from about 3:1 to about 15:1, and most preferably in the range of from 4:1 to 10:1.

Figure 26:
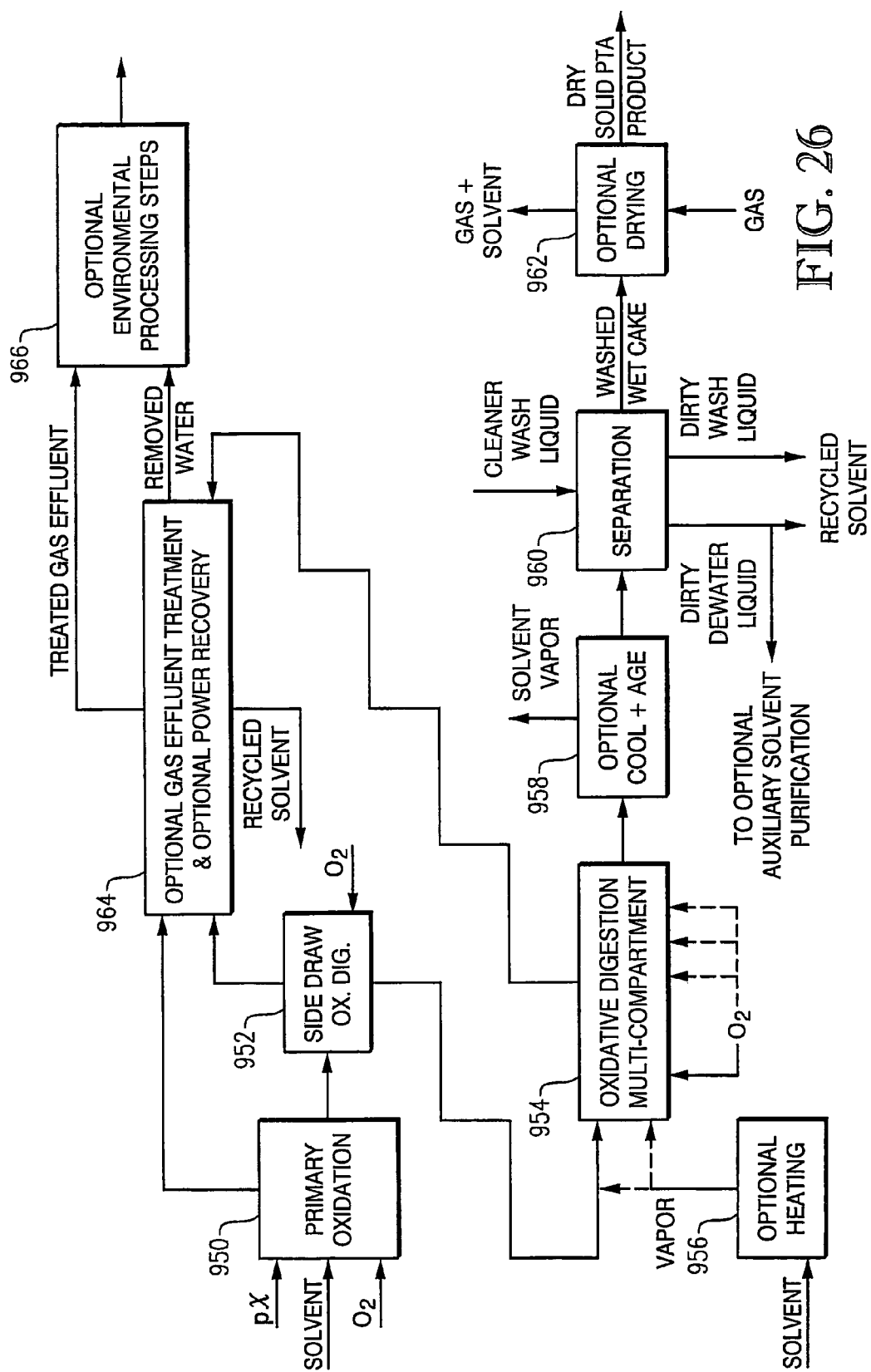
FIG. 26 is a simplified process flow diagram of a process for making PTA in accordance with one embodiment of the present invention, particularly illustrating a configuration employing an early sidedraw oxidative digestion stage, heating of the slurry fed to later oxidative digestion by vapor injection, and a system for treating overhead gasses of primary oxidation and oxidative digestion.

Typically, the $O_2$-max horizontal slice will be located near the bottom of the primary reaction medium, while the $O_2$-min horizontal slice will be located near the top of the primary reaction medium. Preferably, the $O_2$-min horizontal slice is one of the 5 upper-most horizontal slices of the 30 discrete horizontal slices. Most preferably, the $O_2$-min horizontal slice is the upper-most one of the 30 discrete horizontal slices, as illustrated in FIG. 17. Preferably, the $O_2$-max horizontal slice is one of the 10 lower-most horizontal slices of the 30 discrete horizontal slices. Most preferably, the $O_2$-max horizontal slice is one of the 5 lower-most horizontal slices of the 30 discrete horizontal slices. For example, FIG. 26 illustrates the $O_2$-max horizontal slice as the third horizontal slice from the bottom of the reactor. It is preferred for the vertical spacing between the $O_2$-min and $O_2$-max horizontal slices to be at least about 2W, more preferably at least about 4W, and most preferably at least 6W. It is preferred for the vertical spacing between the $O_2$-min and $O_2$-max horizontal slices to be at least about 0.2H, more preferably at least about 0.4H, and most preferably at least 0.6H The time-averaged and volume-averaged oxygen concentration, on a wet basis, of the $O_2$-min horizontal slice is preferably in the range of from about 0.1 to about 3 mole percent, more preferably in the range of from about 0.3 to about 2 mole percent, and most preferably in the range of from 0.5 to 1.5 mole percent. The time-averaged and volume-averaged oxygen concentration of the $O_2$-max horizontal slice is preferably in the range of from about 4 to about 20 mole percent, more preferably in the range of from about 5 to about 15 mole percent, and most preferably in the range of from 6 to 12 mole percent. The time-averaged concentration of oxygen, on a dry basis, in the gaseous effluent discharged from the reactor via the gas outlet is preferably in the range of from about 0.5 to about 9 mole percent, more preferably in the range of from about 1 to about 7 mole percent, and most preferably in the range of from 1.5 to 5 mole percent.

Because the oxygen concentration decays so markedly toward the top of the primary reaction medium, it is desirable that the demand for oxygen be reduced in the top of the primary reaction medium. This reduced demand for oxygen near the top of the primary reaction medium can be accomplished by creating a vertical gradient in the concentration of the aromatic compound (e.g., para-xylene), where the minimum concentration of aromatic compound is located near the top of the primary reaction medium.

With respect to quantifying the aromatic compound (e.g., para-xylene) concentration gradient, when the primary reaction medium is theoretically partitioned into 30 discrete horizontal slices of equal volume, an AR-max horizontal slice is identified as having the maximum aromatic compound concentration of all the 30 horizontal slices and an AR-min horizontal slice is identified as having the minimum aromatic compound concentration of the horizontal slices located above the AR-max horizontal slice. The aromatic compound concentrations of the horizontal slices are measured in the liquid phase on a time-averaged and volume-averaged mass fraction basis. It is preferred for the ratio of the aromatic compound concentration of the AR-max horizontal slice to the aromatic compound concentration of the AR-min horizontal slice to be greater than about 5:1, more preferably greater than about 10:1, still more preferably greater than about 20:1, and most preferably in the range of from 40:1 to 1000:1.

Typically, the AR-max horizontal slice will be located near the bottom of the primary reaction medium, while the AR-min horizontal slice will be located near the top of the primary reaction medium. Preferably, the AR-min horizontal slice is one of the 5 upper-most horizontal slices of the 30 discrete horizontal slices. Most preferably, the AR-min horizontal slice is the upper-most one of the 30 discrete horizontal slices, as illustrated in FIG. 17. Preferably, the AR-max horizontal slice is one of the 10 lower-most horizontal slices of the 30 discrete horizontal slices. Most preferably, the AR-max horizontal slice is one of the 5 lower-most horizontal slices of the 30 discrete horizontal slices. For example, FIG. 26 illustrates the AR-max horizontal slice as the fifth horizontal slice from the bottom of the reactor. It is preferred for the vertical spacing between the AR-min and AR-max horizontal slices to be at least about 2W, where "W" is the maximum width of the primary reaction medium. More preferably, the vertical spacing between the AR-min and AR-max horizontal slices is at least about 4W, and most preferably at least 6W. Given a height "H" of the primary reaction medium, it is preferred for the vertical spacing between the AR-min and AR-max horizontal slices to be at least about 0.2H, more preferably at least about 0.4H, and most preferably at least 0.6H.

The time-averaged and volume-averaged aromatic compound (e.g., para-xylene) concentration in the liquid phase of the AR-min horizontal slice is preferably less than about 5,000 ppmw, more preferably less than about 2,000 ppmw, still more preferably less than about 400 ppmw, and most preferably in the range of from 1 ppmw to 100 ppmw. The time-averaged and volume-averaged aromatic compound concentration in the liquid phase of the AR-max horizontal slice is preferably in the range of from about 100 ppmw to about 10,000 ppmw, more preferably in the range of from about 200 ppmw to about 5,000 ppmw, and most preferably in the range of from 500 ppmw to 3,000 ppmw.

Although it is preferred for the primary oxidation reactor to provide vertical gradients in the concentration of the aromatic compound, it is also preferred that the volume percent of the primary reaction medium having an aromatic compound concentration in the liquid phase above 1,000 ppmw be minimized. Preferably, the time-averaged volume percent of the primary reaction medium having an aromatic compound concentration in the liquid phase above 1,000 ppmw is less than about 9 percent, more preferably less than about 6 percent, and most preferably less than 3 percent. Preferably, the time-averaged volume percent of the primary reaction medium having an aromatic compound concentration in the liquid phase above 2,500 ppmw is less than about 1.5 percent, more preferably less than about 1 percent, and most preferably less than 0.5 percent. Preferably, the time-averaged volume percent of the primary reaction medium having an aromatic compound concentration in the liquid phase above 10,000 ppmw is less than about 0.3 percent, more preferably less than about 0.1 percent, and most preferably less than 0.03 percent. Preferably, the time-averaged volume percent of the primary reaction medium having an aromatic compound concentration in the liquid phase above 25,000 ppmw is less than about 0.03 percent, more preferably less than about 0.015 percent, and most preferably less than 0.007 percent. The inventors note that the volume of the primary reaction medium having the elevated levels of aromatic compound need not lie in a single contiguous volume. At many times, the chaotic flow patterns in a primary oxidation reaction vessel produce simultaneously two or more continuous but segregated portions of the primary reaction medium having the elevated levels of aromatic compound. At each time used in the time averaging, all such continuous but segregated volumes larger than 0.0001 volume percent of the total primary reaction medium are added together to determine the total volume having the elevated levels of aromatic compound concentration in the liquid phase.

In addition to the concentration gradients of oxygen and aromatic compound, discussed above, it is preferred for a temperature gradient to exist in the primary reaction medium. Referring again to FIG. 17, this temperature gradient can be quantified in a manner similar to the concentration gradients by theoretically partitioning the primary reaction medium into 30 discrete horizontal slices of equal volume and measuring the time-averaged and volume-averaged temperature of each slice. The horizontal slice with the lowest temperature out of the lowest 15 horizontal slices can then be identified as the T-min horizontal slice, and the horizontal slice located above the T-min horizontal slice and having the maximum temperature of all the slices above the T-min horizontal slice can then be identified as the "T-max horizontal slice." It is preferred for the temperature of the T-max horizontal slice to be at least about 1° C. higher than the temperature of the T-min horizontal slice. More preferably the temperature of the T-max horizontal slice is in the range of from about 1.25 to about 12° C. higher than the temperature of the T-min horizontal slice. Most preferably the temperature of the T-max horizontal slice is in the range of from 2 to 8° C. higher than the temperature of the T-min horizontal slice. The temperature of the T-max horizontal slice is preferably in the range of from about 125 to about 200° C., more preferably in the range of from about 140 to about 180° C., and most preferably in the range of from 150 to 170° C.

Typically, the T-max horizontal slice will be located near the center of the primary reaction medium, while the T-min horizontal slice will be located near the bottom of the primary reaction medium. Preferably, the T-min horizontal slice is one of the 10 lower-most horizontal slices of the 15 lowest horizontal slices. Most preferably, the T-min horizontal slice is one of the 5 lower-most horizontal slices of the 15 lowest horizontal slices. For example, FIG. 17 illustrates the T-min horizontal slice as the second horizontal slice from the bottom of the reactor. Preferably, the T-max horizontal slice is one of the 20 middle horizontal slices of the 30 discrete horizontal slices. Most preferably, the T-min horizontal slice is one of the 14 middle horizontal slices of the 30 discrete horizontal slices. For example, FIG. 17 illustrates the T-max horizontal slice as the twentieth horizontal slice from the bottom of the reactor (i.e., one of the middle 10 horizontal slices). It is preferred for the vertical spacing between the T-min and T-max horizontal slices to be at least about 2W, more preferably at least about 4W, and most preferably at least 6W. It is preferred for the vertical spacing between the T-min and T-max horizontal slices to be at least about 0.2H, more preferably at least about 0.4H, and most preferably at least 0.6H.

As discussed above, when a vertical temperature gradient exists in the primary reaction medium, it can be advantageous to withdraw the primary reaction medium at an elevated location where the temperature of primary reaction medium is highest, especially when the withdrawn product is subjected to further downstream processing at higher temperatures. Thus, when primary reaction medium 36 is withdrawn from the reaction zone via one or more elevated outlets, as illustrated in FIGS. 15 and 16, it is preferred for the elevated outlet(s) to be located near the T-max horizontal slice. Preferably, the elevated outlet is located within 10 horizontal slices of the T-max horizontal slice, more preferably within 5 horizontal slices of the T-max horizontal slice, and most preferably within 2 horizontal slices of the T-max horizontal slice.

It is now noted that many of the inventive features described herein can be employed in multiple oxidation reactor systems—not just systems employing a single primary oxidation reactor. In addition, certain inventive features described herein can be employed in mechanically-agitated and/or flow-agitated oxidation reactors—not just bubble-agitated reactors (i.e., bubble column reactors). For example, the inventors have discovered certain advantages associated with staging/varying oxygen concentration and/or oxygen consumption rate throughout the primary reaction medium. The advantages realized by the staging of oxygen concentration/consumption in the primary reaction medium can be realized whether the total volume of the reaction medium is contained in a single vessel or in multiple vessels. Further, the advantages realized by the staging of oxygen concentration/consumption in the primary reaction medium can be realized whether the reaction vessel(s) is mechanically-agitated, flow-agitated, and/or bubble-agitated.

One way of quantifying the degree of staging of oxygen concentration and/or consumption rate in a primary reaction medium is to compare two or more distinct 20-percent continuous volumes of the primary reaction medium. These 20-percent continuous volumes need not be defined by any particular shape. However, each 20-percent continuous volume must be formed of a contiguous volume of the primary reaction medium (i.e., each volume is "continuous"), and the 20-percent continuous volumes must not overlap one another (i.e., the volumes are "distinct"). These distinct 20-percent continuous volumes can be located in the same reactor or in multiple reactors.

Figure 18:
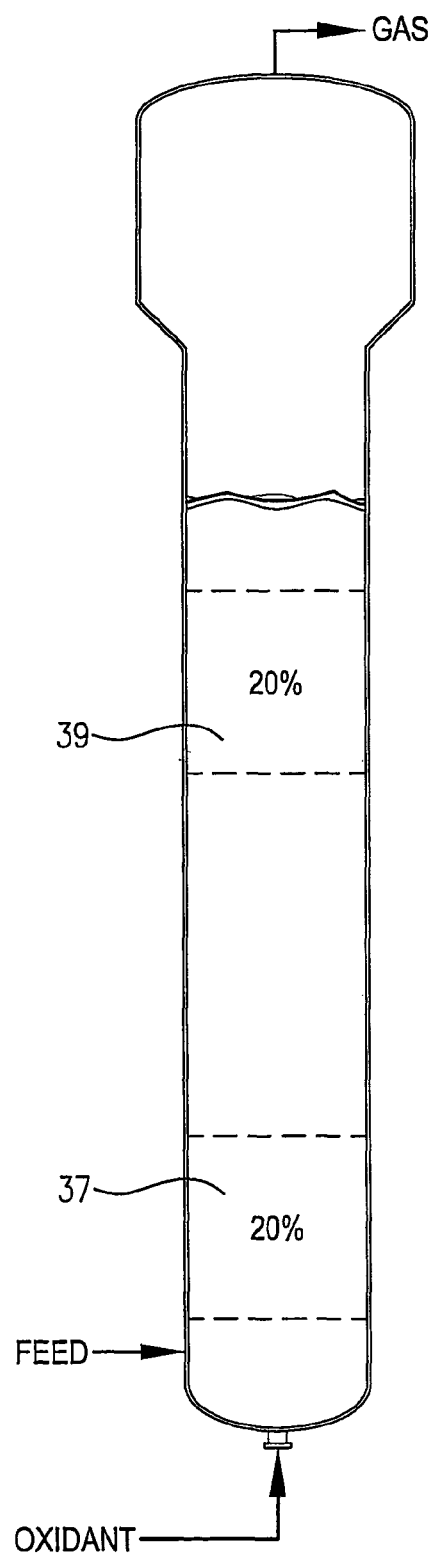
FIG. 18 is a side view of a bubble column reactor containing a multi-phase reaction medium, particularly illustrating first and second discrete 20-percent continuous volumes of the reaction medium that have substantially different oxygen concentrations and/or oxygen consumption rates.

Referring now to FIG. 18, the primary oxidation bubble column reactor is illustrated as containing a primary reaction medium that includes a first distinct 20-percent continuous volume 37 and a second distinct 20-percent continuous volume 39. The staging of oxygen availability in the primary reaction medium can be quantified by referring to the 20-percent continuous volume of primary reaction medium having the most abundant mole fraction of oxygen in the gas phase and by referring to the 20-percent continuous volume of primary reaction medium having the most depleted mole fraction of oxygen in the gas phase. In the gas phase of the distinct 20-percent continuous volume of the primary reaction medium containing the highest concentration of oxygen in the gas phase, the time-averaged and volume-averaged oxygen concentration, on a wet basis, is preferably in the range of from about 3 to about 18 mole percent, more preferably in the range of from about 3.5 to about 14 mole percent, and most preferably in the range of from 4 to 10 mole percent. In the gas phase of the distinct 20-percent continuous volume of the primary reaction medium containing the lowest concentration of oxygen in the gas phase, the time-averaged and volume-averaged oxygen concentration, on a wet basis, is preferably in the range of from about 0.3 to about 5 mole percent, more preferably in the range of from about 0.6 to about 4 mole percent, and most preferably in the range of from 0.9 to 3 mole percent. Furthermore, the ratio of the time-averaged and volume-averaged oxygen concentration, on a wet basis, in the most abundant 20-percent continuous volume of primary reaction medium compared to the most depleted 20-percent continuous volume of primary reaction medium is preferably in the range of from about 1.5:1 to about 20:1, more preferably in the range of from about 2:1 to about 12:1, and most preferably in the range of from 3:1 to 9:1.

The staging of oxygen consumption rate in the primary reaction medium can be quantified in terms of an oxygen-STR, initially described above. Oxygen-STR was previously describe in a global sense (i.e., from the perspective of the average oxygen-STR of the entire primary reaction medium); however, oxygen-STR may also be considered in a local sense (i.e., a portion of the primary reaction medium) in order to quantify staging of the oxygen consumption rate throughout the primary reaction medium.

The inventors have discovered that it is very useful to cause the oxygen-STR to vary throughout the primary reaction medium in general harmony with the desirable gradients disclosed herein relating to pressure in the primary reaction medium and to the mole fraction of molecular oxygen in the gas phase of the primary reaction medium. Thus, it is preferable that the ratio of the oxygen-STR of a first distinct 20-percent continuous volume of the primary reaction medium compared to the oxygen-STR of a second distinct 20-percent continuous volume of the primary reaction medium be in the range of from about 1.5:1 to about 20:1, more preferably in the range of from about 2:1 to about 12:1, and most preferably in the range of from 3:1 to 9:1. In one embodiment the "first distinct 20-percent continuous volume" is located closer than the "second distinct 20-percent continuous volume" to the location where molecular oxygen is initially introduced into the primary reaction medium. These large gradients in oxygen-STR are desirable whether the partial oxidation primary reaction medium is contained in a bubble column oxidation reactor or in any other type of reaction vessel in which gradients are created in pressure and/or mole fraction of molecular oxygen in the gas phase of the primary reaction medium (e.g., in a mechanically agitated vessel having multiple, vertically disposed stirring zones achieved by using multiple impellers having strong radial flow, possibly augmented by generally horizontal baffle assemblies, with oxidant flow rising generally upwards from a feed near the lower portion of the reaction vessel, notwithstanding that considerable back-mixing of oxidant flow may occur within each vertically disposed stirring zone and that some back-mixing of oxidant flow may occur between adjacent vertically disposed stirring zones). That is, when a gradient exists in the pressure and/or mole fraction of molecular oxygen in the gas phase of the primary reaction medium, the inventors have discovered that it is desirable to create a similar gradient in the chemical demand for dissolved oxygen by the means disclosed herein.

A preferred means of causing the local oxygen-STR to vary is by controlling the locations of feeding the aromatic compound and by controlling the mixing of the liquid phase of the primary reaction medium to control gradients in concentration of aromatic compound according to other disclosures of the present invention. Other useful means of causing the local oxygen-STR to vary include causing variation in reaction activity by causing local temperature variation and by changing the local mixture of catalyst and solvent components (e.g., by introducing an additional gas to cause evaporative cooling in a particular portion of the primary reaction medium and by adding a solvent stream containing a higher amount of water to decrease activity in a particular portion of the primary reaction medium).

When the oxidation reactor has a reactor-in-reactor configuration, as described above with respect to FIGS. 12-14, it is preferred for the concentration gradients, temperature gradients, and oxygen-STR gradients described herein with reference to FIGS. 17-18 to apply to the portion of the reaction medium located inside the external reactor and outside the internal reactor (e.g., reaction medium 220a in FIG. 12).

In accordance with one embodiment of the present invention, the purity of the solvent portion of the primary oxidation feed (i.e., the "solvent feed") and the purity of the aromatic compound portion of the primary oxidation feed (i.e., the "aromatic compound feed") are controlled within certain ranges specified below. Along with other embodiments of the present invention, this enables the purity of the liquid phase and, if present, the solid phase and the combined slurry (i.e., solid plus liquid) phase of the primary oxidation reaction medium to be controlled in certain preferred ranges, outlined below.

With respect to the solvent feed, it is known to oxidize an aromatic compound(s) in a primary oxidation reactor/zone to produce a polycarboxylic acid, wherein the solvent feed introduced into the reaction medium is a mixture of analytical-purity acetic acid and water, as is often employed at laboratory scale and pilot scale. Likewise, it is known to conduct primary oxidation wherein the solvent (i.e., initial liquid) leaving the reaction medium is separated from the produced polycarboxylic acid (i.e., initial solid) and then recycled back to the primary oxidation reactor/zone as feed solvent, primarily for reasons of manufacturing cost. This solvent recycling causes certain feed impurities and process by-products to accumulate over time in the recycled solvent. Various means are known in the art to help purify recycled solvent before re-introduction into the reaction medium. Generally, a higher degree of purification of the recycled solvent leads to significantly higher manufacturing cost than does a lower degree of purification by similar means. One embodiment of the present invention relates to understanding and defining the preferred ranges of a large number of impurities within the solvent feed, many of which were heretofore thought largely benign, in order to find an optimal balance between overall manufacturing cost and overall product purity. "Recycled solvent feed" is defined herein as solvent feed that was previously part of a reaction medium subjected to primary oxidation in a primary oxidation zone/reactor and exited the primary oxidation zone/reactor as part of the initial slurry product. For example, recycled solvent feed to a partial oxidation reaction medium for oxidizing para-xylene to form TPA is solvent that originally formed part of the partial oxidation reaction medium, was removed from the reaction medium as a liquid phase of a TPA slurry, was separated away from most solid TPA mass, and was then returned to the partial oxidation reaction medium. As described above, such recycled solvent feed is prone to accumulate all manner of undesirable impurities unless specific auxiliary process steps are provided for solvent purification, at considerable capital and operating cost. For economic reasons, it is preferable that at least about 20 weight percent of the solvent feed to the primary reaction medium of the present invention is recycled solvent, more preferably at least about 40 weight percent, still more preferably at least about 80 weight percent, and most preferably at least 90 weight percent. For reasons of solvent inventory and of on-stream time in a manufacturing unit, it is preferable that portions of recycled solvent pass through primary reaction medium at least once per day of operation, more preferably at least once per day for at least seven consecutive days of operation, and most preferably at least once per day for at least 30 consecutive days of operation.

The inventors have discovered that, for reasons of reaction activity and for consideration of metallic impurities left in the polycarboxylic acid product, the concentrations of selected multivalent metals within the recycled solvent feed are preferably in ranges specified immediately below. The concentration of iron in recycled solvent is preferably below about 150 ppmw, more preferably below about 40 ppmw, and most preferably between 0 and 8 ppmw. The concentration of nickel in recycled solvent is preferably below about 150 ppmw, more preferably below about 40 ppmw, and most preferably between 0 and 8 ppmw. The concentration of chromium in recycled solvent is preferably below about 150 ppmw, more preferably below about 40 ppmw, and most preferably between 0 and 8 ppmw. The concentration of molybdenum in recycled solvent is preferably below about 75 ppmw, more preferably below about 20 ppmw, and most preferably between 0 and 4 ppmw. The concentration of titanium in recycled solvent is preferably below about 75 ppmw, more preferably below about 20 ppmw, and most preferably between 0 and 4 ppmw. The concentration of copper in recycled solvent is preferably below about 20 ppmw, more preferably below about 4 ppmw, and most preferably between 0 and 1 ppmw. Other metallic impurities are also typically present in recycled solvent, generally varying at lower levels in proportion to one or more of the above listed metals. Controlling the above listed metals in the preferred ranges will keep other metallic impurities at suitable levels.

These metals can arise as impurities in any of the incoming process feeds (e.g., in incoming aromatic compound, solvent, oxidant, and catalyst compounds). Alternatively, the metals can arise as corrosion products from any of the process units contacting reaction medium and/or contacting recycled solvent. The means for controlling the metals in the disclosed concentration ranges include the appropriate specification and monitoring of the purity of various feeds and the appropriate usage of materials of construction, including, but not limited to, many commercial grades of titanium and of stainless steels including those grades known as duplex stainless steels and high molybdenum stainless steels.

The inventors have also discovered preferred ranges for selected aromatic compounds in the recycled solvent feed. These include both precipitated and dissolved aromatic compounds within the recycled solvent.

Surprisingly, even precipitated product (e.g., TPA) from a partial oxidation of para-xylene, is a contaminant to be managed in recycled solvent. Because there are surprisingly preferred ranges for the levels of solids within the primary reaction medium, any precipitated product in the solvent feed directly subtracts from the amount of aromatic compound that can be fed in concert. Furthermore, feeding precipitated TPA solids in the recycled solvent at elevated levels has been discovered to affect adversely the character of the particles formed within a precipitating oxidation medium, leading to undesirable character in downstream operations (e.g., product filtration, solvent washing, oxidative digestion of crude product, dissolution of crude product for further processing, and so on). Another undesirable characteristic of precipitated solids in the recycle solvent feed is that these often contain very high levels of precipitated impurities, as compared to impurity concentrations in the bulk of the solids within the TPA slurries from which much of the recycled solvent is obtained. Possibly, the elevated levels of impurities observed in solids suspended in recycled solvent may relate to nucleation times for precipitation of certain impurities from the recycled solvent and/or to cooling of the recycled solvent, whether intentional or due to ambient losses. For example, concentrations of highly-colored and undesirable 2,6-dicarboxyfluorenone have been observed at far higher levels in solids present in recycled solvent at 80° C. than are observed in TPA solids separated from recycled solvent at 160° C. Similarly, concentrations of isophthalic acid have been observed at much higher levels in solids present in recycled solvent compared to levels observed in TPA solids from the primary reaction medium. Exactly how specific precipitated impurities entrained within recycled solvent behave when re-introduced to the primary reaction medium appears to vary. This depends perhaps upon the relative solubility of the impurity within the liquid phase of the primary reaction medium, perhaps upon how the precipitated impurity is layered within the precipitated solids, and perhaps upon the local rate of TPA precipitation where the solid first re-enters the primary reaction medium. Thus, the inventors have found it useful to control the level of certain impurities in the recycled solvent, as disclosed below, without respect to whether these impurities are present in the recycled solvent in dissolved form or are entrained particulates therein.

The amount of precipitated solids present in recycled solvent is determined by a gravimetric method as follows. A representative sample is withdrawn from the solvent supply to the primary reaction medium while the solvent is flowing in a conduit toward the primary reaction medium. A useful sample size is about 100 grams captured in a glass container having about 250 milliliters of internal volume. Before being released to atmospheric pressure, but while continuously flowing toward the sample container, the recycled solvent is cooled to less than 100° C.; this cooling is in order to limit solvent evaporation during the short interval before being sealed closed in the glass container. After the sample is captured at atmospheric pressure, the glass container is sealed closed immediately. Then the sample is allowed to cool to about 20° C. while surrounded by air at about 20° C. and without forced convection. After reaching about 20° C., the sample is held at this condition for at least about 2 hours. Then, the sealed container is shaken vigorously until a visibly uniform distribution of solids is obtained. Immediately thereafter, a magnetic stirrer bar is added to the sample container and rotated at sufficient speed to maintain effectively uniform distribution of solids. A 10 milliliter aliquot of the mixed liquid with suspended solids is withdrawn by pipette and weighed. Then the bulk of the liquid phase from this aliquot is separated by vacuum filtration, still at about 20° C. and effectively without loss of solids. The moist solids filtered from this aliquot are then dried, effectively without sublimation of solids, and these dried solids are weighed. The ratio of the weight of the dried solids to the weight of the original aliquot of slurry is the fraction of solids, typically expressed as a percentage and referred to herein as the amount of "precipitated solids at 20° C." in the solvent feed.

The inventors have discovered that aromatic compounds dissolved in the liquid phase of the reaction medium and comprising aromatic carboxylic acids lacking non-aromatic hydrocarbyl groups (e.g., isophthalic acid, benzoic acid, phthalic acid, 2,5,4'-tricarboxybiphenyl) are surprisingly pernicious components. Although these compounds are much reduced in chemical activity in the subject reaction medium compared to aromatic compounds having non-aromatic hydrocarbyl groups, the inventors have discovered that these compounds nonetheless undergo numerous detrimental reactions. Thus, it is advantageous to control the content of these compounds in preferred ranges in the liquid phase of the reaction medium. This leads to preferred ranges of select compounds in recycled solvent feed and also to preferred ranges of select precursors in the oxidizable aromatic compound feed.

For example, in the liquid-phase partial oxidation of para-xylene to terephthalic acid (TPA), the inventors have discovered that the highly-colored and undesirable impurity 2,7-dicarboxyfluorenone (2,7-DCF) is virtually undetectable in the reaction medium and product off-take when meta-substituted aromatic compounds are at very low levels in the reaction medium. The inventors have discovered that when isophthalic acid impurity is present at increasing levels in the solvent feed, the formation of 2,7-DCF rises in almost direct proportion. The inventors have also discovered that when meta-xylene impurity is present in the feed of para-xylene, the formation of 2,7-DCF again rises almost in direct proportion. Furthermore, even if the solvent feed and aromatic compound feed are devoid of meta-substituted aromatic compounds, the inventors have discovered that some isophthalic acid is formed during a typical partial oxidation of very pure para-xylene, particularly when benzoic acid is present in the liquid phase of the reaction medium. This self-generated isophthalic acid may, owing to its greater solubility than TPA in solvent comprising acetic acid and water, build up over time in commercial units employing recycled solvent. Thus, the amount of isophthalic acid within solvent feed, the amount of meta-xylene within aromatic compound feed, and the rate of self-creation of isophthalic acid within the reaction medium are all appropriately considered in balance with each other and in balance with any reactions that consume isophthalic acid. Isophthalic acid has been discovered to undergo additional consumptive reactions besides the formation of 2,7-DCF, as are disclosed below. In addition, the inventors have discovered that there are other issues to consider when setting appropriate ranges for the meta-substituted aromatic species in the partial oxidation of para-xylene to TPA. Other highly-colored and undesirable impurities, such as 2,6-dicarboxyfluorenone (2,6-DCF), appear to relate greatly to dissolved, para-substituted aromatic species, which are always present with para-xylene feed to a liquid-phase oxidation. Thus, the suppression of 2,7-DCF is best considered in perspective with the level of other colored impurities being produced.

For example, in the liquid-phase partial oxidation of para-xylene to TPA, the inventors have discovered that the formation of trimellitic acid rises as the levels isophthalic acid and phthalic acid rise within the reaction medium. Trimellitic acid is a tri-functional carboxylic acid leading to branching of polymer chains during production of PET from TPA. In many PET applications, branching levels must be controlled to low levels and hence trimellitic acid must be controlled to low levels in purified TPA. Besides leading to trimellitic acid, the presence of meta-substituted and ortho-substituted species in the reaction medium also give rise to other tricarboxylic acids (e.g., 1,3,5-tricarboxybenzene). Furthermore, the increased presence of tricarboxylic acids in the reaction medium increases the amount of tetracarboxylic acid formation (e.g., 1,2,4,5-tetracarboxybenzene). Controlling the summed production of all aromatic carboxylic acids having more than two carboxylic acid groups is one factor in setting the preferred levels of meta-substituted and ortho-substituted species in the recycled solvent feed, in the aromatic compound feed, and in the reaction medium according to the present invention.

For example, in the liquid-phase partial oxidation of para-xylene to TPA, the inventors have discovered that increased levels in the liquid phase of the reaction medium of several dissolved aromatic carboxylic acids lacking non-aromatic hydrocarbyl groups leads directly to the increased production of carbon monoxide and carbon dioxide. This increased production of carbon oxides represents a yield loss on both oxidant and on aromatic compound, the later since many of the co-produced aromatic carboxylic acids, which on the one hand may be viewed as impurities, on the other hand also have commercial value. Thus, appropriate removal of relatively soluble carboxylic acids lacking non-aromatic hydrocarbyl groups from recycle solvent has an economic value in preventing yield loss of oxidizable aromatic compound and of oxidant, in addition to suppressing the generation of highly undesirable impurities such as various fluorenones and trimellitic acid.

For example, in the liquid-phase partial oxidation of para-xylene to TPA, the inventors have discovered that formation of 2,5,4'-tricarboxybiphenyl is seemingly unavoidable. The 2,5,4'-tricarboxybiphenyl is an aromatic tricarboxylic acid formed by the coupling of two aromatic rings, perhaps by the coupling of a dissolved para-substituted aromatic species with an aryl radical, perhaps an aryl radical formed by decarboxylation or decarbonylation of a para-substituted aromatic species. Fortunately, the 2,5,4'-tricarboxybiphenyl is typically produced at lower levels than trimellitic acid and does not usually lead to significantly increased difficulties with branching of polymer molecules during production of PET. However, the inventors have discovered that elevated levels of 2,5,4'-tricarboxybiphenyl in a reaction medium comprising oxidation of alkyl aromatics according to preferred embodiments of the present invention lead to increased levels of highly-colored and undesirable 2,6-DCF. The increased 2,6-DCF is possibly created from the 2,5,4'-tricarboxybiphenyl by ring closure with loss of a water molecule, though the exact reaction mechanism is not known with certainty. If 2,5,4'-tricarboxybiphenyl, which is more soluble in solvent comprising acetic acid and water than is TPA, is allowed to build up too high within recycled solvent, conversion rates to 2,6-DCF can become unacceptably large.

For example, in the liquid-phase partial oxidation of para-xylene to TPA, the inventors have discovered that aromatic carboxylic acids lacking non-aromatic hydrocarbyl groups (e.g., isophthalic acid) generally lead to mild suppression of the chemical activity of the reaction medium when present in the liquid phase at sufficient concentration.

For example, in the liquid-phase partial oxidation of para-xylene to TPA, the inventors have discovered that precipitation is very often non-ideal (i.e. non-equilibrium) with respect to the relative concentrations of different chemical species in the solid phase and in the liquid phase. Perhaps, this is because the precipitation rate is very fast at the space-time reaction rates preferred herein, leading to non-ideal co-precipitation of impurities, or even occlusion. Thus, when it is desired to limit the concentration of certain impurities (e.g., trimellitic acid and 2,6-DCF) within crude TPA, owing to the configuration of downstream unit operations, it is preferable to control their concentration in solvent feed as well as their generation rate within the reaction medium.

For example, the inventors have discovered that benzophenone compounds (e.g., 4,4'-dicarboxybenzophenone and 2,5,4'-tricarboxybenzophenone) made during partial oxidation of para-xylene, have undesirable effects in a PET reaction medium even though benzophenone compounds are not as highly colored in TPA per se as are fluorenones and anthraquinones. Accordingly, it is desirable to limit the presence of benzophenones and select precursors in recycled solvent and in aromatic compound feed. Furthermore, the inventors have discovered that the presence of elevated levels of benzoic acid, whether admitted in recycled solvent or formed within the reaction medium, leads to elevated rates of production of 4,4 '-dicarboxybenzophenone.

In review, the inventors have discovered and sufficiently quantified a surprising array of reactions for aromatic compounds lacking non-aromatic hydrocarbyl groups that are present in the liquid-phase partial oxidation of para-xylene to TPA. Recapping just the single case of benzoic acid, the inventors have discovered that increased levels of benzoic acid in the reaction medium of certain embodiments of the present invention lead to greatly increased production of the highly colored and undesirable 9-fluorenone-2-carboxylic acid, to greatly increased levels of 4,4'-dicarboxybiphenyl, to increased levels of 4,4'-dicarboxybenzophenone, to a mild suppression of chemical activity of the intended oxidation of para-xylene, and to increased levels of carbon oxides and attendant yield losses. The inventors have discovered that increased levels of benzoic acid in the reaction medium also lead to increased production of isophthalic acid and phthalic acid, the levels of which are desirably controlled in low ranges according to similar aspects of the current invention. The number and importance of reactions involving benzoic acid are perhaps even more surprising since some recent inventors contemplate using benzoic acid in place of acetic acid as a primary component of solvent (See, e.g., U.S. Pat. No. 6,562,997). Additionally, the present inventors have observed that benzoic acid is self-generated during oxidation of para-xylene at rates that are quite important relative to its formation from impurities, such as toluene and ethylbenzene, commonly found in aromatic compound feed comprising commercial-purity para-xylene.

On the other hand, the inventors have discovered little value from additional regulation of recycled solvent composition in regard to the presence of oxidizable aromatic compound and in regard to aromatic reaction intermediates that both retain non-aromatic hydrocarbyl groups and are also relatively soluble in the recycled solvent. In general, these compounds are either fed to or created within the primary reaction medium at rates substantially greater than their presence in recycled solvent; and the consumption rate of these compounds within the primary reaction medium is great enough, retaining one or more non-aromatic hydrocarbyl groups, to limit appropriately their build-up within recycled solvent. For example, during partial oxidation of para-xylene in a multi-phase reaction medium, para-xylene evaporates to a limited extent along with large quantities of solvent. When this evaporated solvent exits the reactor as part of the off-gas and is condensed for recovery as recycled solvent, a substantial portion of the evaporated para-xylene condenses therein as well. It is not necessary to limit the concentration of this para-xylene in recycled solvent. For example, if solvent is separated from solids upon slurry exiting a para-xylene oxidation reaction medium, this recovered solvent will contain a similar concentration of dissolved para-toluic acid to that present at the point of removal from the reaction medium. Although it may be important to limit the standing concentration of para-toluic acid within the liquid phase of the reaction medium, see below, it is not necessary to regulate separately the para-toluic acid in this portion of recycled solvent owing to its relatively good solubility and to its low mass flow rate relative to the creation of para-toluic acid within the reaction medium. Similarly, the inventors have discovered little reason to limit the concentrations in recycled solvent of aromatic compounds with methyl substituents (e.g. toluic acids), aromatic aldehydes (e.g., terephthaldehyde), of aromatic compounds with hydroxy-methyl substituents (e.g., 4-hydroxymethylbenzoic acid), and of brominated aromatic compounds retaining at least one non-aromatic hydrocarbyl group (e.g., alpha-bromo-para-toluic acid) below those inherently found in the liquid phase exiting from the reaction medium occurring in the partial oxidation of xylene according to preferred embodiments of the present invention. Surprisingly, the inventors have also discovered that it is also not necessary to regulate in recycled solvent the concentration of selected phenols intrinsically produced during partial oxidation of xylene, for these compounds are created and destroyed within the primary reaction medium at rates much greater than their presence in recycled solvent. For example, the inventors have discovered that 4-hydroxybenzoic acid has relatively small effects on chemical activity in the preferred embodiments of the present invention when co-fed at rates of over 2 grams of 4-hydroxybenzoic acid per 1 kilogram of para-xylene, far higher than the natural presence in recycled solvent, despite being reported by others as a significant poison in similar reaction medium (See, e.g., W. Partenheimer, *Catalysis Today* 23 (1995) p. 81).

Thus, there are numerous reactions and numerous considerations in setting the preferred ranges of various aromatic impurities in the solvent feed as now disclosed. These discoveries are stated in terms of the aggregated weight average composition of all solvent streams being fed to the primary reaction medium during the course of a set time period, preferably one day, more preferably one hour, and most preferably one minute. For example, if one solvent feed flows substantially continuously with a composition of 40 ppmw of isophthalic acid at a flow rate of 7 kilograms per minute, a second solvent feed flows substantially continuously with a composition of 2,000 ppmw of isophthalic acid at a flow rate of 10 kilograms per minute, and there are no other solvent feed streams entering the primary reaction medium, then the aggregated weight average composition of the solvent feed is calculated as (40*7+2,000 *10)/(7+10)=1,193 ppmw of isophthalic acid. It is notable that the weight of any aromatic compound feed or of any oxidant feed that are perhaps commingled with the solvent feed before entering the primary reaction medium are not considered in calculating the aggregated weight average composition of the solvent feed.

Table 1, below, lists preferred values for certain components in the solvent feed introduced into the primary reaction medium. The solvent feed components listed in Table 1 are as follows: 4-carboxybenzaldehyde (4-CBA), 4,4'-dicarboxystilbene (4,4'-DCS), 2,6-dicarboxyanthraquinone (2,6-DCA), 2,6-dicarboxyfluorenone (2,6-DCF), 2,7-dicarboxyfluorenone (2,7-DCF), 3,5-dicarboxyfluorenone (3,5-DCF), 9-fluorenone-2-carboxylic acid (9F-2CA), 9-fluorenone-4-carboxylic acid (9F-4CA), total fluorenones including other fluorenones not individually listed (total fluorenones), 4,4'-dicarboxybiphenyl (4,4'-DCB), 2,5,4'-tricarboxybiphenyl (2,5,4'-TCB), phthalic acid (PA), isophthalic acid (IPA), benzoic acid (BA), trimellitic acid (TMA), 2,6-dicarboxybenzocoumarin (2,6-DCBC), 4,4'-dicarboxybenzil (4,4'-DCBZ), 4,4'-dicarboxybenzophenone (4,4'-DCBP), 2,5,4'-tricarboxybenzophenone (2,5,4'-TCBP), terephthalic acid (TPA), precipitated solids at 20° C., and total aromatic carboxylic acids lacking non-aromatic hydrocarbyl groups. Table 1, below provides the preferred amounts of these impurities in solvent feed to primary oxidation according to an embodiment of the present invention.

TABLE 1

Components of Solvent Feed Introduced into Primary Oxidation

| Component Identification | Preferred Amt. (ppmw) | More Preferred Amt. (ppmw) | Most Preferred Amt. (ppmw) |
|---|---|---|---|
| 4-CBA | <1,200 | 30-600 | 60-300 |
| 4,4'-DCS | <3 | <2 | <1 |
| 2,6-DCA | <6 | 0.1-3 | 0.2-1 |
| 2,6-DCF | <20 | 0.1-10 | 0.5-5 |
| 2,7-DCF | <10 | 0.1-5 | 0.5-2 |
| 3,5-DCF | <10 | <5 | <2 |
| 9F-2CA | <10 | 0.1-5 | 0.5-2 |
| 9F-4CA | <5 | <3 | <1 |
| Total fluorenones | <40 | <20 | 1-8 |
| 4,4'-DCB | <45 | <15 | 0.5-5 |
| 2,5,4'-TCB | <45 | 0.1-15 | 0.5-5 |
| PA | <1,000 | 15-400 | 40-150 |
| IPA | 2,500 | 40-1,200 | 120-400 |
| BA | <4,500 | 50-1,500 | 150-500 |
| TMA | <1,000 | 15-400 | 40-150 |
| 2,6-DCBC | <40 | <20 | <5 |
| 4,4'-DCBZ | <40 | <20 | <5 |
| 4,4'-DCBP | <40 | <20 | <5 |
| 2,5,4'-TCBP | <40 | <20 | 0.5-5 |
| TPA | <9,000 | 200-6,000 | 400-2,000 |
| Precipitated Solids at 20° C. | <9,000 | 200-6,000 | 600-2,000 |
| Total Aromatic Carboxylic Acids Lacking Non-Aromatic Hydrocarbyl Groups | <18,000 | 300-9,000 | 450-3,000 |

Many other aromatic impurities are also typically present in recycled solvent, generally varying at even lower levels and/or in proportion to one or more of the disclosed aromatic compounds. Methods for controlling the disclosed aromatic compounds in the preferred ranges will typically keep other aromatic impurities at suitable levels.

When bromine is used within the reaction medium, a large number of ionic and organic forms of bromine are known to exist in a dynamic equilibrium. These various forms of bromine have different stability characteristics once leaving the reaction medium and passing through various unit operations pertaining to recycled solvent. For example, alpha-bromo-para-toluic acid may persist as such at some conditions or may rapidly hydrolyze at other conditions to form 4-hydroxymethylbenzoic acid and hydrogen bromide. In the present invention, it is preferable that at least about 40 weight percent, more preferable that at least about 60 weight percent, and most preferable that at least about 80 weight percent of the total mass of bromine present in the aggregated solvent feed to the primary reaction medium is in one or more of the following chemical forms: ionic bromine, alpha-bromo-para-toluic acid, and bromoacetic acid.

Although the importance and value of controlling the aggregated weight average purity of solvent feed within the disclosed, desired ranges of the present invention has not heretofore been discovered and/or disclosed, suitable means for controlling the solvent feed purity may be assembled from various methods already known in the art. First, any solvent evaporated from the primary reaction medium is typically of suitable purity providing that liquid or solids from the primary reaction medium are not entrained with the evaporated solvent. The feeding of reflux solvent droplets into the off-gas disengaging space above the primary reaction medium, as disclosed herein, appropriately limits such entrainment; and recycled solvent of suitable purity with respect to aromatic compound can be condensed from such off-gas. Second, the more difficult and costly purification of recycled solvent feed typically relates to solvent taken from the primary reaction medium in liquid form and to solvent that subsequently contacts the liquid and/or solid phases of the reaction medium withdrawn from the primary reaction vessel (e.g., recycled solvent obtained from a filter in which solids are concentrated and/or washed, recycled solvent obtained from a centrifuge in which solids are concentrated and/or washed, recycled solvent taken from a crystallization operation, and so on). However, means are also known in the art for effecting the necessary purification of these recycled solvent streams using one or more prior disclosures. With respect to controlling precipitated solids in recycled solvent to be within the ranges specified, suitable control means include, but are not limited to, gravimetric sedimentation, mechanical filtration using filter cloth on rotary belt filters and rotary drum filters, mechanical filtration using stationary filter medium within pressure vessels, hydro-cyclones, and centrifuges. With respect to controlling dissolved aromatic species in recycled solvent to be within the ranges specified, the control means include, but are not limited to, those disclosed in U.S. Pat. No. 4,939,297 and U.S. Pat. App. Pub. No. 2005-0038288, incorporated herein by reference. However, none of these prior inventions discovered and disclosed the preferred levels of purity in the aggregated solvent feed as disclosed herein. Rather, these prior inventions merely provided means to purify selected and partial streams of recycled solvent without deducing the present inventive, optimal values of the composition of the aggregated weight average solvent feed to the primary reaction medium.

Turning now to the purity of the feed of aromatic compound, it is known that certain levels of isophthalic acid, phthalic acid, and benzoic acid are present and tolerable at low levels in purified TPA used for polymer production. Moreover, it is known these species are relatively more soluble in many solvents and may be advantageously removed from purified TPA by crystallization processes. However, from an embodiment of the invention disclosed herein, it is now known that controlling the level of several relatively soluble aromatic species, notably including isophthalic acid, phthalic acid, and benzoic acid, in the liquid phase of the primary oxidation reaction medium is surprisingly important for controlling the level of polycyclic and colored aromatic compounds created in the reaction medium, for controlling compounds with more than 2 carboxylic acid functions per molecule, for controlling reaction activity within the partial oxidation reaction medium, and for controlling yield losses of oxidant and of aromatic compound.

It is known within the art that isophthalic acid, phthalic acid, and benzoic acid are formed in the reaction medium as follows. Meta-Xylene feed impurity oxidizes in good conversion and yield to IPA. Ortho-Xylene feed impurity oxidizes in good conversion and yield to phthalic acid. Ethylbenzene and toluene feed impurities oxidize in good conversion and yield to benzoic acid. However, the inventors have observed that significant amounts of isophthalic acid, phthalic acid, and benzoic acid are also formed within a reaction medium comprising para-xylene by means other than oxidation of meta-xylene, ortho-xylene, ethylbenzene, and toluene. These other intrinsic chemical routes possibly include decarbonylation, decarboxylation, the re-organization of transition states, and addition of methyl and carbonyl radicals to aromatic rings.

In determining preferred ranges of impurities in the feed of aromatic compound, many factors are relevant. Any impurity in the feed is likely to be a direct yield loss and a product purification cost if the purity requirements of the oxidized product are sufficiently strict (e.g., in a reaction medium for partial oxidation of para-xylene, toluene and ethylbenzene typically found in commercial-purity para-xylene lead to benzoic acid, and this benzoic acid is largely removed from most commercial TPA). When the partial oxidation product of a feed impurity participates in additional reactions, factors other than simple yield loss and removal become appropriate when considering how much feed purification cost to incur (e.g., in a reaction medium for partial oxidation of para-xylene, ethylbenzene leads to benzoic acid, and benzoic acid subsequently leads to highly colored 9-fluorenone-2-carboxylic acid, to isophthalic acid, to phthalic acid, and to increased carbon oxides, among others). When the reaction medium self-generates additional amounts of an impurity by chemical mechanisms not directly related to feed impurities, the analysis becomes still more complex (e.g., in a reaction medium for partial oxidation of para-xylene, benzoic acid is also self-generated from para-xylene itself). In addition, the downstream processing of the crude polycarboxylic acid product may affect the considerations for preferred feed purity. For example, the cost of removing to suitable levels a direct impurity (benzoic acid) and subsequent impurities (isophthalic acid, phthalic acid, 9-fluorenone-2-carboxylic acid, et al.) may be one and the same, may be different from each other, and may be different from the requirements of removing a largely unrelated impurity (e.g., incomplete oxidation product 4-CBA in the oxidation of para-xylene to TPA).

The following disclosed feed purity ranges for para-xylene are preferred where para-xylene is fed with solvent and oxidant to a reaction medium for partial oxidation to produce TPA. These ranges are more preferred in TPA production process having post-oxidation steps to remove from reaction medium impurities other than oxidant and solvent (e.g., catalyst metals). These ranges are still more preferred in TPA production processes that remove additional 4-CBA from CTA (e.g., by conversion of CTA to dimethyl terephthalate plus impurity esters and subsequent separation of the methyl ester of 4-CBA by distillation, by oxidative digestion methods for converting 4-CBA to TPA, by hydrogenation methods for converting 4-CBA to para-toluic acid, which is then separated by partial-crystallization methods). These ranges are most preferred in TPA production processes that remove additional 4-CBA from CTA by oxidative digestion methods for converting 4-CBA to TPA.

Using new knowledge of preferred ranges of recycling aromatic compounds and of the relative amounts of the aromatic compounds formed directly from oxidation of feed impurities as compared to other intrinsic chemical routes, improved ranges for impurities have been discovered for impure para-xylene being fed to a partial oxidation process for TPA production. Table 2 below provides preferred values for the amount of meta-xylene, ortho-xylene, and ethylbenzene+toluene in the para-xylene feed expressed in parts per million by weight of para-xylene.

TABLE 2

Components of Impure Para-Xylene Feed to Primary Oxidation

| Component Identification | Preferred Amt. (ppmw) | More Preferred Amt. (ppmw) | Most Preferred Amt. (ppmw) |
| --- | --- | --- | --- |
| meta-xylene | 20-800 | 50-600 | 100-400 |
| ortho-xylene | 10-300 | 20-200 | 30-100 |
| ethylbenzene + toluene* | 20-700 | 50-500 | 100-300 |
| total | 50-900 | 100-800 | 200-700 |

*Specification for ethylbenzene + toluene is each separately and in sum

Those skilled in the art will now recognize the above impurities within impure para-xylene may have their greatest effect on the reaction medium after their partial oxidation products have accumulated in recycled solvent. For example, feeding the upper amount of the most preferred range of meta-xylene, 400 ppmw, will immediately produce about 200 ppmw of isophthalic acid within the liquid phase of the reaction medium when operating with about 33 weight percent solids in the reaction medium. This compares with an input from the upper amount of the most preferred range for isophthalic acid in recycled solvent of 400 ppmw that, after allowing for a typical solvent evaporation to cool the reaction medium, amounts to about 1,200 ppmw of isophthalic acid within the liquid phase of the reaction medium. Thus, it is the accumulation of partial oxidation products over time within recycled solvent that represents the greatest probable impact of the meta-xylene, ortho-xylene, ethylbenzene, and toluene impurities in the feed of impure para-xylene. Accordingly, the above ranges for impurities in impure para-xylene feed are preferred to be maintained for at least one-half of each day of operation of any partial oxidation reaction medium in a particular manufacturing unit, more preferably for at least three-quarters of each day for at least seven consecutive days of operation, and most preferably when the mass-weighted averages of the impure para-xylene feed composition are within the preferred ranges for at least 30 consecutive days of operation.

Means for obtaining impure para-xylene of preferred purity are already known in the art and include, but are not limited to, distillation, partial crystallization methods at sub-ambient temperatures, and molecular sieve methods using selective pore-size adsorption. However, the preferred ranges of purity specified herein are, at their high end, more demanding and expensive than characteristically practiced by commercial suppliers of para-xylene; and yet at the low end, the preferred ranges avoid overly costly purification of para-xylene for feeding to a partial oxidation reaction medium by discovering and disclosing where the combined effects of impurity self-generation from para-xylene itself and of impurity consumptive reactions within the reaction medium become more important than the feed rates of impurities within impure para-xylene.

When the xylene-containing feed stream contains selected impurities, such as ethyl-benzene and/or toluene, oxidation of these impurities can generate benzoic acid. As used herein, the term "impurity-generated benzoic acid" shall denote benzoic acid derived from any source other than xylene during xylene oxidation.

As disclosed herein, a portion of the benzoic acid produced during xylene oxidation is derived from the xylene itself. This production of benzoic acid from xylene is distinctly in addition to any portion of benzoic acid production that may be impurity-generated benzoic acid. Without being bound by theory, it is believed that benzoic acid is derived from xylene within the reaction medium when various intermediate oxidation products of xylene spontaneously decarbonylate (carbon monoxide loss) or decarboxylate (carbon dioxide loss) to thereby produce aryl radicals. These aryl radicals can then abstract a hydrogen atom from one of many available sources in the reaction medium and produce self-generated benzoic acid. Whatever the chemical mechanism, the term "self-generated benzoic acid," as used herein, shall denote benzoic acid derived from xylene during xylene oxidation.

As also disclosed herein, when para-xylene is oxidized to produce terephthalic acid (TPA), the production of self-generated benzoic acid causes para-xylene yield loss and oxidant yield loss. In addition, the presence of self-generated benzoic acid in the liquid phase of the reaction medium correlates with increases for many undesirable side reactions, notably including generation of highly colored compounds called monocarboxy-fluorenones. Self-generated benzoic acid also contributes to the undesirable accumulation of benzoic acid in recycled solvent, which further elevates the concentration of benzoic acid in the liquid phase of the reaction medium. Thus, formation of self-generated benzoic acid is desirably minimized, but this is also appropriately considered simultaneously with impurity-generated benzoic acid, with factors affecting consumption of benzoic acid, with factors pertaining to other issues of reaction selectivity, and with overall economics.

The inventors have discovered that the self-generation of benzoic acid can be controlled to low levels by appropriate selection of, for example, temperature, xylene distribution, and oxygen availability within the reaction medium during oxidation. Not wishing to be bound by theory, lower temperatures and improved oxygen availability appear to suppress the decarbonylation and/or decarboxylation rates, thus avoiding the yield loss aspect of self-generated benzoic acid. Sufficient oxygen availability appears to direct aryl radicals toward other more benign products, in particular hydroxybenzoic acids. Distribution of xylene in the reaction medium may also affect the balance between aryl radical conversion to benzoic acid or to hydroxybenzoic acids. Whatever the chemical mechanisms, the inventors have discovered reaction conditions that, although mild enough to reduce benzoic acid production, are severe enough to oxidize a high fraction of the hydroxybenzoic acid production to carbon monoxide and/or carbon dioxide, which are easily removed from the polycarboxylic acid product.

In a preferred embodiment of the present invention, the oxidation reactor is configured and operated in a manner such that the formation of self-generated benzoic acid is minimized and the oxidation of hydroxybenzoic acids to carbon monoxide and/or carbon dioxide is maximized. When the oxidation reactor is employed to oxidize para-xylene to terephthalic acid, it is preferred that para-xylene makes up at least about 50 weight percent of the total xylene in the feed stream introduced into the reactor. More preferably, para-xylene makes up at least about 75 weight percent of the total xylene in the feed stream. Still more preferably, para-xylene makes up at least 95 weight percent of the total xylene in the feed stream. Most preferably, para-xylene makes up substantially all of the total xylene in the feed stream.

When the reactor is employed to oxidize para-xylene to terephthalic acid, it is preferred for the rate of production of terephthalic acid to be maximized, while the rate of production of self-generated benzoic acid is minimized. Preferably, the ratio of the rate of production (by weight) of terephthalic acid to the rate of production (by weight) of self-generated benzoic acid is at least about 500:1, more preferably at least about 1,000:1, and most preferably at least 1,500:1. As will be seen below, the rate of production of self-generated benzoic acid is preferably measured when the concentration of benzoic acid in the liquid phase of the reaction medium is below 2,000 ppmw, more preferably below 1,000 ppmw, and most preferably below 500 ppmw, because these low concentrations suppress to suitably low rates reactions that convert benzoic acid to other compounds.

Combining the self-generated benzoic acid and the impurity-generated benzoic acid, the ratio of the rate of production (by weight) of terephthalic acid to the rate of production (by weight) of total (self-generated and impurity-generated) benzoic acid is preferably at least about 400:1, more preferably at least about 700:1, and most preferably at least 1,100:1. As will be seen below, the summed rate of production of self-generated benzoic acid plus impurity-generated benzoic acid is preferably measured when the concentration of benzoic acid in the liquid phase of the reaction medium is below 500 ppmw, because these low concentrations suppress to suitably low rates reactions that convert benzoic acid to other compounds.

As disclosed herein, elevated concentrations of benzoic acid in the liquid phase of the oxidative digestion reaction medium lead to increased formation of many other aromatic compounds, several of which are noxious impurities in TPA; and, as disclosed herein, elevated concentrations of benzoic acid in the liquid phase of the reaction medium lead to increased formation of carbon oxide gases, the formation of which represents yield loss on oxidant and on aromatic compounds and/or solvent. Furthermore, it is now disclosed that the inventors have discovered a considerable portion of this increased formation of other aromatic compounds and of carbon oxides derives from reactions that convert some of the benzoic acid molecules themselves, as contrasted to benzoic acid catalyzing other reactions without itself being consumed. Accordingly, the "net generation of benzoic acid" is defined herein as the time-averaged weight of all benzoic acid exiting the reaction medium minus the time-averaged weight of all benzoic acid entering the reaction medium during the same period of time. This net generation of benzoic acid is often positive, driven by the formation rates of impurity-generated benzoic acid and of self-generated benzoic acid. However, the inventors have discovered that the conversion rate of benzoic acid to carbon oxides, and to several other compounds, appears to increase approximately linearly as the concentration of benzoic acid is increased in the liquid phase of the reaction medium, measured when other reaction conditions comprising temperature, oxygen availability, STR, and reaction activity are maintained appropriately constant. Thus, when the concentration of benzoic acid in the liquid-phase of the reaction medium is great enough, perhaps due to an elevated concentration of benzoic acid in recycled solvent, then the conversion of benzoic acid molecules to other compounds, including carbon oxides, can become equal to or greater than the chemical generation of new benzoic acid molecules. In this case, the net generation of benzoic acid can become balanced near zero or even negative. The inventors have discovered that when the net generation of benzoic acid is positive, then the ratio of the rate of production (by weight) of terephthalic acid in the reaction medium compared to the rate of net generation of benzoic acid in the reaction medium is preferably above about 700:1, more preferably above about 1,100:1, and most preferably above 4,000:1. The inventors have discovered that when the net generation of benzoic acid is negative, the ratio of the rate of production (by weight) of terephthalic acid in the reaction medium compared to the rate of net generation of benzoic acid in the reaction medium is preferably above about 200:(−1), more preferably above about 1,000:(−1), and most preferably above 5,000:(−1).

Another embodiment of the current invention relates to partial oxidation of aromatic compound with appropriate balancing of the suppression of noxious aromatic impurities on the one hand against the production of carbon dioxide and carbon monoxide, collectively carbon oxides (COx), on the other. These carbon oxides typically exit the reaction vessel in the off-gas, and they correspond to a destructive loss of solvent and of aromatic compound, including the ultimately preferred oxidized derivatives (e.g., acetic acid, para-xylene, and TPA). The inventors have discovered lower bounds for the production of carbon oxides below which it seems the high creation of noxious aromatic impurities, as described below, and the low overall conversion level are inevitably too poor to be of economic utility. The inventors have also discovered upper bounds of carbon oxides above which the generation of carbon oxides continues to increase with little further value provided by reduction in generation of noxious aromatic impurities.

The inventors have discovered that reducing the liquid-phase concentrations of aromatic compound feed and of aromatic intermediate species within a reaction medium leads to lower generation rates for noxious impurities during the partial oxidation of aromatic compound. These noxious impurities include coupled aromatic rings and/or aromatic molecules containing more than the desired number of carboxylic acid groups (e.g., in the oxidation of para-xylene the noxious impurities include 2,6-dicarboxyanthraquinone, 2,6-dicarboxyfluorenone, trimellitic acid, 2,5,4'-tricarboxybiphenyl, and 2,5,4'-benzophenone). The aromatic intermediate species include aromatic compounds descended from the feed of oxidizable aromatic compound and still retaining non-aromatic hydrocarbyl groups (e.g., in the oxidation of para-xylene the aromatic intermediate species comprise para-tolualdehyde, terephthaldehyde, para-toluic acid, 4-CBA, 4-hydroxymethylbenzoic acid, and alpha-bromo-para-toluic acid). The aromatic compound feed and the aromatic intermediate species retaining non-aromatic hydrocarbyl groups, when present in the liquid phase of the reaction medium, appear to lead to noxious impurities in a manner similar to that already disclosed herein for dissolved aromatic species lacking non-aromatic hydrocarbyl groups (e.g., isophthalic acid).

Set against this need for higher reaction activity to suppress formation of noxious aromatic impurities during partial oxidation of oxidizable aromatic compound, the inventors have discovered that the undesirable attendant result is increased production of carbon oxides. It is important to appreciate that these carbon oxides represent a yield loss of aromatic compound and oxidant, not just solvent. Explicitly, a substantial and sometimes principal fraction of the carbon oxides comes from the aromatic compound, and its derivatives, rather than from solvent; and often the aromatic compound costs more per carbon unit than does solvent. Furthermore, it is important to appreciate that the desired product carboxylic acid (e.g., TPA) is also subject to over-oxidation to carbon oxides when present in the liquid phase of the reaction medium.

It is also important to appreciate that the present invention relates to reactions in the liquid phase of the reaction medium and to reactant concentrations therein. This is in contrast to some prior inventions that relate directly to the creation in precipitated solid form of aromatic compound retaining non-aromatic hydrocarbyl groups. Specifically, for the partial oxidation of para-xylene to TPA, certain prior inventions pertain to the amount of 4-CBA precipitated in the solid phase of CTA. However, the present inventors have discovered a variance of greater than two to one for the ratio of 4-CBA in the solid phase to 4-CBA in the liquid phase, using the same specifications of temperature, pressure, catalysis, solvent composition and space-time reaction rate of para-xylene, depending upon whether the partial oxidation is conducted in a well-mixed autoclave or in a reaction medium with oxygen and para-xylene staging according to the present invention. Further, the inventors have observed that the ratio of 4-CBA in the solid phase to 4-CBA in the liquid phase can also vary by over two to one in either well-mixed or staged reaction medium depending upon the space-time reaction rate of para-xylene at otherwise similar specifications of temperature, pressure, catalysis, and solvent composition. Additionally, 4-CBA in the solid phase CTA does not appear to contribute to the formation of noxious impurities, and 4-CBA in the solid phase can be recovered and oxidized on to TPA simply and at high yield (e.g., by oxidative digestion of the initial slurry as is described herein); whereas the removal of noxious impurities is far more difficult and costly than removal of solid phase 4-CBA, and the production of carbon oxides represents a permanent yield loss. Thus, it is important to distinguish that this aspect of the present invention relates to liquid-phase compositions in the reaction medium.

Whether sourced from solvent or aromatic compound, the inventors have discovered that at conversions of commercial utility the production of carbon oxides relates strongly to the level of overall reaction activity despite wide variation in the specific combination of temperature, metals, halogens, temperature, acidity of the reaction medium as measured by pH, water concentration employed to obtain the level of overall reaction activity. The inventors have found it useful for the partial oxidation of xylene to evaluate the level of overall reaction activity using the liquid-phase concentration of toluic acids at the mid-height of the reaction medium, the bottom of the reaction medium, and the top of the reaction medium.

Thus, there arises an important simultaneous balancing to minimize the creation of noxious impurities by increasing reaction activity and yet to minimize the creation of carbon oxides by lowering reaction activity. That is, if the overall production of carbon oxides is suppressed too low, then excessive levels of noxious impurities are formed, and vice versa.

Furthermore, the inventors have discovered that the solubility and the relative reactivity of the desired carboxylic acid (e.g., TPA) and the presence of other dissolved aromatic species lacking non-aromatic hydrocarbyl groups introduce a very important fulcrum in this balancing of carbon oxides versus noxious impurities. The desired product carboxylic acid is typically dissolved in the liquid phase of the reaction medium, even when also present in solid form. For example, at temperatures in the preferred ranges, TPA is soluble in a reaction medium comprising acetic acid and water at levels ranging from about one thousand ppmw to in excess of 1 weight percent, with solubility increasing as temperature increases. Notwithstanding that there are differences in the reaction rates toward forming various noxious impurities from oxidizable aromatic compound feed (e.g., para-xylene), from aromatic reaction intermediates (e.g., para-toluic acid), from the desired product aromatic carboxylic acid (e.g., TPA), and from aromatic species lacking non-aromatic hydrocarbyl groups (e.g., isophthalic acid), the presence and reactivity of the latter two groups establishes a region of diminishing returns with regards to further suppression of the former two groups, oxidizable aromatic compound feed and aromatic reaction intermediates. For example, in a partial oxidation of para-xylene to TPA, if dissolved TPA amounts to 7,000 ppmw in the liquid phase of the reaction medium at given conditions, dissolved benzoic acid amounts to 8,000 ppmw, dissolved isophthalic acid amounts to 6,000 ppmw, and dissolved phthalic acid amounts to 2,000 ppmw, then the value toward further lowering of total noxious compounds begins to diminish as reaction activity is increased to suppress the liquid-phase concentration para-toluic acid and 4-CBA below similar levels. That is, the presence and concentration in the liquid phase of the reaction medium of aromatic species lacking non-aromatic hydrocarbyl groups is very little altered by increasing reaction activity, and their presence serves to expand upwards the region of diminishing returns for reducing the concentration of reaction intermediates in order to suppress formation of noxious impurities.

Thus, one embodiment of the present invention provides preferred ranges of carbon oxides (carbon monoxide and carbon dioxide), bounded on the lower end by low reaction activity and excessive formation of noxious impurities and on the upper end by excessive carbon losses, but at levels lower than previously discovered and disclosed as commercially useful. Accordingly, the formation of carbon oxides is preferably controlled as follows. The ratio of moles of total carbon oxides produced to moles of oxidizable aromatic compound fed is preferably in the range of from about 0.02:1 to about 0.25:1, more preferably in the range of from about 0.04:1 to about 0.22:1, still more preferably in the range of from about 0.05:1 to about 0.19:1, and most preferably in the range of from 0.06:1 to 0.15:1. The ratio of moles of carbon dioxide produced to moles of oxidizable aromatic compound fed is preferably in the range of from about 0.01:1 to about 0.21:1, more preferably in the range of from about 0.03:1 to about 0.19:1, still more preferably in the range of from about 0.04:1 to about 0.16:1, and most preferably in the range of from 0.05:1 to 0.11:1. The ratio of moles of carbon monoxide produced to moles of oxidizable aromatic compound fed is preferably in the range of from about 0.005:1 to about 0.09:1, more preferably in the range of from about 0.01:1 to about 0.07:1, still more preferably in the range of from about 0.015:1 to about 0.05:1, and most preferably in the range of from 0.02:1 to 0.04.

The content of carbon dioxide in dry off-gas from the oxidation reactor is preferably in the range of from about 0.1 to about 1.5 mole percent, more preferably in the range of from about 0.20 to about 1.2 mole percent, still more preferably in the range of from about 0.25 to about 0.9 mole percent, and most preferably in the range of from 0.30 to 0.8 mole percent. The content of carbon monoxide in dry off-gas from the oxidation reactor is preferably in the range of from about 0.05 to about 0.6 mole percent, more preferably in the range of from about 0.10 to about 0.5 mole percent, still more preferably in the range of from 0.15 to about 0.35 mole percent, and most preferably in the range of from 0.18 to 0.28 mole percent.

The inventors have discovered that an important factor for reducing the production of carbon oxides to these preferred ranges is improving the purity of the recycled solvent and of the feed of aromatic compound to reduce the concentration of aromatic compounds lacking non-aromatic hydrocarbyl groups according to disclosures of the present invention—this simultaneously reduces the formation of carbon oxides and of noxious impurities. Another factor is improving distribution of para-xylene and oxidant within the reaction vessel according to disclosures of the present invention. Other factors enabling the above preferred levels of carbon oxides are to operate with the gradients in the reaction medium as disclosed herein for pressure, for temperature, for concentration of aromatic compound in the liquid phase, and for oxidant in the gas phase. Other factors enabling the above preferred levels of carbon oxides are to operate within the disclosures herein preferred for space-time reaction rate, pressure, temperature, solvent composition, catalyst composition, and mechanical geometry of the reaction vessel.

One possible benefit of operating within the preferred ranges of carbon oxide formation is that the usage of molecular oxygen can be reduced, though not to stoichiometric values. Notwithstanding the good staging of oxidant and aromatic compound according to the present invention, an excess of oxygen must be retained above the stoichiometric value, as calculated for feed of aromatic compound alone, to allow for some losses to carbon oxides and to provide excess molecular oxygen to control the formation of noxious impurities. Specifically for the case where xylene is the feed of aromatic compound, the feed ratio of weight of molecular oxygen to weight of xylene is preferably in the range of from about 0.9:1 to about 1.5:1, more preferably in the range of from about 0.95:1 to about 1.3:1, and most preferably in the range of from 1:1 to 1.15:1. Specifically for xylene feed, the time-averaged content of molecular oxygen in the dry off-gas from the oxidation reactor is preferably in the range of from about 0.1 to about 6 mole percent, more preferably in the range of from about 1 to about 2 mole percent, and most preferably in the range of from 1.5 to 3 mole percent.

Another possible benefit of operating within the preferred ranges of carbon oxide formation is that less aromatic compound is converted to carbon oxides and other less valuable forms. This benefit is evaluated using the sum of the moles of all aromatic compounds exiting the reaction medium divided by the sum of the moles of all aromatic compounds entering the reaction medium over a continuous period of time, preferably one hour, more preferably one day, and most preferably 30 consecutive days. This ratio is hereinafter referred to as the "molar survival ratio" for aromatic compounds through the reaction medium and is expressed as a numerical percentage. If all entering aromatic compounds exit the reaction medium as aromatic compounds, albeit mostly in oxidized forms of the entering aromatic compounds, then the molar survival ratio has its maximum value of 100 percent. If exactly 1 of every 100 entering aromatic molecules is converted to carbon oxides and/or other non-aromatic molecules (e.g., acetic acid) while passing through reaction medium, then the molar survival ratio is 99 percent. Specifically for the case where xylene is the principal feed of oxidizable aromatic compound, the molar survival ratio for aromatic compounds through the reaction medium is preferably in the range of from about 98 to about 99.9 percent, more preferably in the range of from about 98.5 to about 99.8 percent, and most preferably in the range of from 99.0 to 99.7 percent.

Another aspect of the current invention involves the production of methyl acetate in a reaction medium comprising acetic acid and one or more oxidizable aromatic compounds. This methyl acetate is relatively volatile compared to water and acetic acid and thus tends to follow the off-gas unless additional cooling or other unit operations are employed to recover it and/or to destroy it prior to releasing the off-gas back to the environment. The formation of methyl acetate thus represents an operating cost and also a capital cost. Perhaps the methyl acetate is formed by first combining a methyl radical, perhaps from decomposition of acetic acid, with oxygen to produce methyl hydroperoxide, by subsequently decomposing to form methanol, and by finally reacting the produced methanol with remaining acetic acid to form methyl acetate. Whatever the chemical path, the inventors have discovered that whenever methyl acetate production is at too low a rate, then the production of carbon oxides are also too low and the production of noxious aromatic impurities are too high. If methyl acetate production is at too high a rate, then the production of carbon oxides are also unnecessarily high leading to yield losses of solvent, aromatic compound and oxidant. When employing the preferred embodiments disclosed herein, the production ratio of moles of methyl acetate produced to moles of oxidizable aromatic compound fed is preferably in the range of from about 0.005:1 to about 0.09:1, more preferably in the range of from about 0.01:1 to about 0.07:1, and most preferably in the range of from 0.02:1 to about 0.04:1.

When the generation of carbon dioxide, carbon monoxide, their sum, and/or methyl acetate are below the preferred ranges disclosed herein or when the molar survival ratio for aromatic compounds is above the preferred ranges disclosed herein, the reaction activity should be increased or the STR should be reduced. One activity accelerator is increased temperature, within the preferred ranges disclosed herein. Another activity accelerator is increased catalytic activity as provided by the mixture of catalytic chemicals and solvent. Generally, increasing cobalt and/or bromine concentrations will accelerate reaction activity, if these are being used within the ranges preferred herein. Adjusting the concentration within the reaction medium of other catalyst components and of water can also be used to accelerate reaction activity. STR is decreased by decreasing the feed rate of aromatic compound and/or by increasing the volume of reaction medium.

When the generation of carbon dioxide, carbon monoxide, their sum, and/or methyl acetate is greater than the preferred ranges disclosed herein and/or when the molar survival ratio for aromatic compounds is below the preferred ranges disclosed herein, preferable control actions include a reverse of the above actions, again within the preferred ranges disclosed herein. The inventors note that it is particularly helpful to raise the STR as far as possible into the ranges herein while maintaining a good quality of oxidation as measured by noxious impurities in the CTA and in the reaction medium. The inventors again note that it is difficult to maintain this quality of oxidation at such high STR and that very careful attention is required with respect toward the following: to feed dispersion upon entering the reaction medium, to aeration quality throughout the reaction medium, to de-aeration upon exit from the reaction medium, to oxygen-STR and dissolved oxygen throughout the reaction medium, to excess oxidant exiting the reaction medium, to the desirable spatial gradient of oxygen-STR, to the desirable spatial gradient of aromatic compound concentration, to the desirable spatial gradient of oxidant concentration, to the overhead pressure, to the desirable spatial gradient of pressure, and to the preferred temperature at the mid-height of the reaction medium, and as are all disclosed herein. In further addition and in order to achieve lower carbon dioxide, carbon monoxide, and/or their sum and/or in order to increase the molar survival ratio for aromatic compounds, the inventors have discovered that it is useful to suppress within the reaction medium the concentration of soluble aromatic compounds lacking non-aromatic hydrocarbyl groups (e.g. isophthalic acid, phthalic acid and benzoic acid); this suppression may be effected by using purer feed of aromatic compound and/or purer solvent, especially within the preferred ranges for each as disclosed herein.

In a reaction medium continuously oxidizing para-xylene to terephthalic acid at the preferred STR disclosed herein, it is preferred that the amount of para-toluic acid in the liquid phase of the reaction medium be maintained in the range from about 200 to about 10,000 ppmw, more preferably from about 800 to about 8,000 ppmw and most preferably from 1,600 to 6,000 ppmw. Furthermore, conversion of para-xylene to terephthalic acid within the reaction medium is preferably maintained above about 50 mole percent, more preferably above about 90 mole percent, still more preferably above about 95 mole percent, and most preferably above 97 mole percent.

As discussed above, the initial slurry produced via primary oxidation carried out in accordance with one or more of the embodiments described herein is surprisingly superior and useful. For example, the preferred initial slurry includes an initial liquid that is relatively low in concentration of important impurities, and this importantly reduces the creation of other even more undesirable impurities as disclosed herein. In addition, the initial slurry composition importantly aids the subsequent processing of the initial liquid to become suitably pure recycled solvent, according to other embodiments of the present invention. Further, when the improved primary oxidation system described herein is used to carry out the liquid-phase partial oxidation of para-xylene to crude terephthalic acid (CTA), the spatial profiles of local reaction intensity, of local evaporation intensity, and of local temperature combined with the liquid flow patterns within the reaction medium and the preferred, relatively low oxidation temperatures contribute to the formation of CTA particles having unique and advantageous properties.

FIGS. 19A and 19B illustrate base CTA particles produced by the improved primary oxidation system described herein. FIG. 19A shows the base CTA particles at 500 times magnification, while FIG. 19B zooms in on one of the base CTA particles and shows that particle at 2,000 times magnification. As perhaps best illustrated in FIG. 19B, each base CTA particle is typically formed of a large number of small, agglomerated CTA subparticles, thereby giving the base CTA particle a relatively high surface area, high porosity, low density, and good dissolvability. Unless otherwise specified, the various properties of the inventive CTA, described below, are measured using a representative sample of the CTA, where the representative sample weighs at least 1 gram and/or is formed of at least 10,000 individual CTA particles. The base CTA particles typically have a mean particle size in the range of from about 20 to about 150 microns, more preferably in the range of from about 30 to about 120 microns, and most preferably in the range of from 40 to 90 microns. The CTA subparticles typically have a mean particle size in the range of from about 0.5 to about 30 microns, more preferably from about 1 to about 15 microns, and most preferably in the range of from 2 to 5 microns. The relatively high surface area of the base CTA particles illustrated in FIGS. 19A and 19B, can be quantified using a Braunauer-Emmett-Teller (BET) surface area measurement method. Preferably, the base CTA particles have an average BET surface of at least about 0.6 meters squared per gram ($m^2/g$). More preferably, the base CTA particles have an average BET surface area in the range of from about 0.8 to about 4 $m^2/g$. Most preferably, the base CTA particles have an average BET surface area in the range of from 0.9 to 2 $m^2/g$. The physical properties (e.g., particle size, BET surface area, porosity, and dissolvability) of the base CTA particles formed by optimized oxidation process of a preferred embodiment of the present invention permit purification of the CTA particles by more effective and/or economical methods, as described in further detail below with respect to FIGS. 22-26.

The mean particle size values provided above were determined using polarized light microscopy and image analysis. The equipment employed in the particle size analysis included a Nikon E800 optical microscope with a 4× Plan Flour N.A. 0.13 objective, a Spot RT™ digital camera, and a personal computer running Image Pro Plus™ V4.5.0.19 image analysis software. The particle size analysis method included the following main steps: (1) dispersing the CTA powders in mineral oil; (2) preparing a microscope slide/cover slip of the dispersion; (3) examining the slide using polarized light microscopy (crossed polars condition—particles appear as bright objects on black background); (4) capturing different images for each sample preparation (field size=3×2.25 mm; pixel size=1.84 microns/pixel); (5) performing image analysis with Image Pro Plus™ software; (6) exporting the particle measures to a spreadsheet; and (7) performing statistical characterization in the spreadsheet. Step (5) of "performing image analysis with Image Pro Plus™ software" included the substeps of: (a) setting the image threshold to detect white particles on dark background; (b) creating a binary image; (c) running a single-pass open filter to filter out pixel noise; (d) measuring all particles in the image; and (e) reporting the mean diameter measured for each particle. The Image Pro Plus™ software defines mean diameter of individual particles as the number average length of diameters of a particle measured at 2 degree intervals and passing through the particle's centroid. Step 7 of "performing statistical characterization in the spreadsheet" comprises calculating the volume-weighted mean particle size as follows. The volume of each of the n particles in a sample is calculated as if it were spherical using pi/6*$d_i$^3; multiplying the volume of each particle times its diameter to find pi/6*$d_i$^4; summing for all particles in the sample of the values of pi/6*$d_i$^4; summing the volumes of all particles in the sample; and calculating the volume-weighted particle diameter as sum for all n particles in the sample of (pi/6*$d_i$^4) divided by sum for all n particles in the sample of (pi/6*$d_{i^3}$). As used herein, "mean particle size" refers to the volume-weighted mean particle size determined according to the above-described test method; and it is also referred to as D(4,3).

$$D(4,3) = \frac{\sum_{i=1}^{n} \frac{\pi}{6} d_i^4}{\sum_{i=1}^{n} \frac{\pi}{6} d_i^3}$$

In addition, step 7 comprises finding the particle sizes for which various fractions of the total sample volume are smaller. For example, D(v,0.1) is the particle size for which 10 percent of the total sample volume is smaller and 90 percent is larger; D(v,0.5) is the particle size for which one-half of the sample volume is larger and one-half is smaller; D(v,0.9) is the particle size for which 90 percent of the total sample volume is smaller; and so on. In addition, step 7 comprises calculating the value of D(v,0.9) minus D(v,0.1), which is herein defined as the "particle size spread"; and step 7 comprises calculating the value of the particle size spread divided by D(4,3), which is herein defined as the "particle size relative spread."

Furthermore, it is preferable that the D(v,0. 1) of the CTA particles as measured above be in the range from about 5 to about 65 microns, more preferably in the range from about 15 to about 55 microns and most preferably in the range from 25 to 45 microns. It is preferable that the D(v,0.5) of the CTA particles as measured above be in the range from about 10 to about 90 microns, more preferably in the range from about 20 to about 80 microns, and most preferably in the range from 30 to 70 microns. It is preferable that the D(v,0.9) of the CTA particles as measured above be in the range from about 30 to about 150 microns, more preferably in the range from about 40 to about 130 microns, and most preferably in the range from 50 to 110 microns. It is preferable that the particle size relative spread be in the range from about 0.5 to about 2.0, more preferably in the range from about 0.6 to about 1.5, and most preferably in the range from 0.7 to 1.3.

The BET surface area values provided above were measured on a Micromeritics ASAP2000 (available from Micromeritics Instrument Corporation of Norcross, Ga.). In the first step of the measurement process, a 2 to 4 gram of sample of the particles was weighed and dried under vacuum at 50° C. The sample was then placed on the analysis gas manifold and cooled to 77°0 K. A nitrogen adsorption isotherm was measured at a minimum of 5 equilibrium pressures by exposing the sample to known volumes of nitrogen gas and measuring the pressure decline. The equilibrium pressures were appropriately in the range of $P/P_0$=0.01-0.20, where P is equilibrium pressure and $P_0$ is vapor pressure of liquid nitrogen at 77° K. The resulting isotherm was then plotted according to the following BET equation:

$$\frac{P}{V_a(P_o - P)} = \frac{1}{V_m C} + \frac{C-1}{V_m C}\left(\frac{P}{P_o}\right)$$

where $V_a$ is volume of gas adsorbed by sample at P, $V_m$ is volume of gas required to cover the entire surface of the sample with a monolayer of gas, and C is a constant. From this plot, $V_m$ and C were determined. $V_m$ was then converted to a surface area using the cross sectional area of nitrogen at 77° K by:

$$A = \sigma \frac{V_m}{RT}$$

where σ is cross sectional area of nitrogen at 77° K, T is 77° K, and R is the gas constant.

As alluded to above, CTA produced by the improved primary oxidation system described herein exhibits superior dissolution properties verses conventional CTA made by other processes. This enhanced dissolution rate allows the inventive CTA to be purified by more efficient and/or more effective purification processes. The following description addresses the manner in which the rate of dissolution of CTA can be quantified.

The rate of dissolution of a known amount of solids into a known amount of solvent in an agitated mixture can be measured by various protocols. As used herein, a measurement method called the "timed dissolution test" is defined as follows. An ambient pressure of about 0.1 megapascal is used throughout the timed dissolution test. The ambient temperature used throughout the timed dissolution test is about 22° C. Furthermore, the solids, solvent and all dissolution apparatus are fully equilibrated thermally at this temperature before beginning testing, and there is no appreciable heating or cooling of the beaker or its contents during the dissolution time period. A solvent portion of fresh, HPLC analytical grade of tetrahydrofuran (>99.9 percent purity), hereafter THF, measuring 250 grams is placed into a cleaned KIMAX tall form 400 milliliter glass beaker (Kimble® part number 14020, Kimble/Kontes, Vineland, N.J.), which is uninsulated, smooth-sided, and generally cylindrical in form. A Tefloncoated magnetic stirring bar (VWR part number 58948-230, about 1-inch long with ⅜-inch diameter, octagonal cross section, VWR International, West Chester, Pa. 19380) is placed in the beaker, where it naturally settles to the bottom. The sample is stirred using a Variomag® multipoint 15 magnetic stirrer (H&P Labortechnik AG, Oberschleissheim, Germany) magnetic stirrer at a setting of 800 revolutions per minute. This stirring begins no more than 5 minutes before the addition of solids and continues steadily for at least 30 minutes after adding the solids. A solid sample of crude or purified TPA particulates amounting to 250 milligrams is weighed into a non-sticking sample weighing pan. At a starting time designated as t=0, the weighed solids are poured all at once into the stirred THF, and a timer is started simultaneously. Properly done, the THF very rapidly wets the solids and forms a dilute, well-agitated slurry within 5 seconds. Subsequently, samples of this mixture are obtained at the following times, measured in minutes from t=0: 0.08, 0.25, 0.50, 0.75, 1.00, 1.50, 2.00, 2.50, 3.00, 4.00, 5.00, 6.00, 8.00, 10.00, 15.00, and 30.00. Each small sample is withdrawn from the dilute, well-agitated mixture using a new, disposable syringe (Becton, Dickinson and Co, 5 milliliter, REF 30163, Franklin Lakes, N.J. 07417). Immediately upon withdrawal from the beaker, approximately 2 milliliters of clear liquid sample is rapidly discharged through a new, unused syringe filter (25 mm diameter, 0.45 micron, Gelman GHP Acrodisc GF®, Pall Corporation, East Hills, N.Y. 11548) into a new, labeled glass sample vial. The duration of each syringe filling, filter placement, and discharging into a sample vial is correctly less than about 5 seconds, and this interval is appropriately started and ended within about 3 seconds either side of each target sampling time. Within about five minutes of each filling, the sample vials are capped shut and maintained at approximately constant temperature until performing the following chemical analysis. After the final sample is taken at a time of 30 minutes past t=0, all sixteen samples are analyzed for the amount of dissolved TPA using a HPLC-DAD method generally as described elsewhere within this disclosure. However, in the present test, the calibration standards and the results reported are both based upon milligrams of dissolved TPA per gram of THF solvent (hereafter "ppm in THF"). For example, if all of the 250 milligrams of solids were very pure TPA and if this entire amount fully dissolved in the 250 grams of THF solvent before a particular sample were taken, the correctly measured concentration would be about 1,000 ppm in THF.

When CTA produced by the improved primary oxidation system described herein is subjected to the timed dissolution test described above, it is preferred that a sample taken at one minute past t=0 dissolves to a concentration of at least about 500 ppm in THF, more preferably to at least 600 ppm in THF. For a sample taken at two minutes past t=0, it is preferred that CTA according to the current invention will dissolve to a concentration of at least about 700 ppm in THF, more preferably to at least 750 ppm in THF. For a sample taken at four minutes past t=0, it is preferred that CTA according to the current invention will dissolve to a concentration of at least about 840 ppm in THF, more preferably to at least 880 ppm in THF.

The inventors have found that a relatively simple negative exponential growth model is useful to describe the time dependence of the entire data set from a complete timed dissolution test, notwithstanding the complexity of the particulate samples and of the dissolution process. The form of the equation, hereinafter the "timed dissolution model," is as follows:

$$S=A+B*(1-\exp(-C*t)), \text{ where}$$

t=time in units of minutes;

S=solubility, in units of ppm in THF, at time t;

exp=exponential function in the base of the natural logarithm of 2;

A, B=regressed constants in units of ppm in THF, where A relates mostly to the rapid dissolution of the smaller particles at very short times, and where the sum of A+B relates mostly to the total amount of dissolution near the end of the specified testing period; and C=a regressed time constant in units of reciprocal minutes.

The regressed constants are adjusted to minimize the sum of the squares of the errors between the actual data points and the corresponding model values, which method is commonly called a "least squares" fit. A preferred software package for executing this data regression is JMP Release 5.1.2 (SAS Institute Inc., JMP Software, SAS Campus Drive, Cary, N.C. 27513).

When CTA produced by the improved primary oxidation system described herein is tested with the timed dissolution test and fitted to the timed dissolution model described above, it is preferred for the CTA to have a time constant "C" greater than about 0.5 reciprocal minutes, more preferably greater than about 0.6 reciprocal minutes, and most preferably greater than 0.7 reciprocal minutes.

FIGS. 20A and 20B illustrate a conventional CTA particle made by a conventional high-temperature oxidation process in a continuous stirred tank reactor (CSTR). FIG. 20A shows the conventional CTA particle at 500 times magnification, while FIG. 20B zooms in and shows the CTA particle at 2,000 times magnification. A visual comparison of the inventive CTA particles illustrated in FIGS. 19A and 19B and the conventional CTA particle illustrated in FIGS. 20A and 20B shows that the conventional CTA particle has a higher density, lower surface area, lower porosity, and larger particle size than the CTA particles produced by the improved primary oxidation system described herein. In fact, the conventional CTA represented in FIGS. 20A and 20B has a mean particle size of about 205 microns and a BET surface area of about 0.57 m$^2$g.

CTA produced from primary oxidation according to an embodiment of the present invention contains less impurities of selected types than CTA produced by conventional processes and apparatuses, notably those employing recycled solvent. Impurities that may be present in CTA include the following: 4-carboxybenzaldehyde (4-CBA), 4,4'-dicarboxystilbene (4,4'-DCS), 2,6-dicarboxyanthraquinone (2,6-DCA), 2,6-dicarboxyfluorenone (2,6-DCF), 2,7-dicarboxyfluorenone (2,7-DCF), 3,5-dicarboxyfluorenone (3,5-DCF), 9-fluorenone-2-carboxylic acid (9F-2CA), 9-fluorenone-4-carboxylic acid (9F-4CA), total fluorenones including other fluorenones not individually listed (total fluorenones), 4,4'-dicarboxybiphenyl (4,4'-DCB), 2,5,4'-tricarboxybiphenyl (2,5,4'-TCB), phthalic acid (PA), isophthalic acid (IPA), benzoic acid (BA), trimellitic acid (TMA), paratoluic acid (PTAC), 2,6-dicarboxybenzocoumarin (2,6-DCBC), 4,4'-dicarboxybenzil (4,4'-DCBZ), 4,4'-dicarboxybenzophenone (4,4'-DCBP), 2,5,4'-tricarboxybenzophenone (2,5,4'-TCBP). Table 3, below provides the preferred amounts of these impurities in CTA produced according to an embodiment of the present invention.

TABLE 3

Initial CTA Impurities

| Impurity Identification | Preferred Amt. (ppmw) | More Preferred Amt. (ppmw) | Most Preferred Amt. (ppmw) |
|---|---|---|---|
| 4-CBA | <15,000 | 100-8,000 | 400-2,000 |
| 4,4'-DCS | <12 | <6 | <3 |
| 2,6-DCA | <9 | <6 | <2 |
| 2,6-DCF | <100 | 2-50 | 5-25 |
| 2,7-DCF | <30 | <15 | <5 |
| 3,5-DCF | <16 | <8 | <2 |
| 9F-2CA | <16 | <8 | <4 |
| 9F-4CA | <8 | <4 | <2 |
| Total fluorenones | <100 | 2-60 | 4-35 |
| 4,4'-DCB | <64 | 1-32 | 2-8 |
| 2,5,4'-TCB | <24 | <12 | <8 |
| PA | <200 | 3-100 | 5-50 |
| IPA | <800 | 10-400 | 20-200 |
| BA | <600 | 5-300 | 15-100 |
| TMA | <800 | 10-400 | 20-200 |
| PTAC | <2,000 | 10-1,000 | 50-500 |
| 2,6-DCBC | <64 | <32 | <8 |
| 4,4'-DCBZ | <12 | <8 | <4 |
| 4,4'-DCBP | <40 | <30 | <20 |
| 2,5,4'-TCBP | <32 | <16 | <4 |

TABLE 4

Initial Slurry Impurities

| Impurity Identification | Preferred Amt. (ppmw) | More Preferred Amt. (ppmw) | Most Preferred Amt. (ppmw) |
|---|---|---|---|
| 4-CBA | <8,000 | <5,000 | <2,500 |
| 4,4'-DCS | <4 | <2 | <1 |
| 2,6-DCA | <6 | <3 | <1 |
| 2,6-DCF | <70 | 2-40 | 4-20 |
| 2,7-DCF | <12 | <8 | <4 |
| 3,5-DCF | <12 | <8 | <4 |
| 9F-2CA | <12 | <8 | <4 |
| 9F-4CA | <8 | <4 | <2 |
| Total fluorenones | <90 | 2-60 | 5-30 |
| 4,4'-DCB | <64 | 1-16 | 2-4 |
| 2,5,4'-TCB | <60 | 2-40 | 4-20 |
| PA | <3,000 | 25-1,500 | 75-500 |
| IPA | 9,000 | 75-4,500 | 225-1,500 |
| BA | <15,000 | 100-6,000 | 300-2,000 |
| TMA | <3,000 | 25-1,500 | 75-500 |
| PTAC | <8,000 | 100-4,000 | 200-2,000 |
| 4,4'-DCBZ | <5 | <4 | <3 |
| 4,4'-DCBP | <240 | <160 | <80 |
| 2,5,4'-TCBP | <120 | <80 | <40 |

In addition, it is preferred for CTA produced according to an embodiment of the present invention to have reduced color content relative to CTA produced by conventional processes and apparatuses, notably those employing recycled solvent. Thus, it is preferred for CTA produced in accordance to one embodiment of the present invention to have a percent transmittance percent at 340 nanometers (nm) of at least about 25 percent, more preferably of at least about 50 percent, still more preferably of at least about 60 percent, and most preferably of at least 70 percent. It is further preferred for CTA produced in accordance to one embodiment of the present invention to have a percent transmittance percent at 400 nanometers (nm) of at least about 88 percent, more preferably of at least about 90 percent, and most preferably of at least 92 percent.

The test for percent transmittance provides a measure of the colored, light-absorbing impurities present within TPA or CTA. As used herein, the test refers to measurements done on a portion of a solution prepared by dissolving 2.00 grams of dry solid TPA or CTA in 20.0 milliliters of dimethyl sulfoxide (DMSO), analytical grade or better. A portion of this solution is then placed in a Hellma semi-micro flow cell, PN 176.700, which is made of quartz and has a light path of 1.0 cm and a volume of 0.39 milliliters. (Hellma USA, 80 Skyline Drive, Plainview, N.Y. 11803). An Agilent 8453 Diode Array Spectrophotometer is used to measure the transmittance of different wavelengths of light through this filled flow cell. (Agilent Technologies, 395 Page Mill Road, Palo Alto, Calif. 94303). After appropriate correction for absorbance from the background, including but not limited to the cell and the solvent used, the percent transmittance results, characterizing the fraction of incident light that is transmitted through the solution, are reported directly by the machine. Percent transmittance values at light wavelengths of 340 nanometers and 400 nanometers are particularly useful for discriminating pure TPA from many of the impurities typically found therein.

The preferred ranges of various aromatic impurities in the initial slurry (initial solid+initial liquid) withdrawn from the primary oxidation reactor/zone are provided below in Table 4.

These preferred compositions for the initial slurry embody the preferred composition of the liquid phase of the reaction medium while usefully avoiding experimental difficulties pertaining to precipitation of additional liquid phase components from the reaction medium into solid phase components during sampling from the reaction medium, separation of liquids and solids, and shifting to analytical conditions.

Many other aromatic impurities are also typically present in the slurry phase of the reaction medium and in CTA of the reaction medium, generally varying at even lower levels and/or in proportion to one or more of the disclosed aromatic compounds. Controlling the disclosed aromatic compounds in the preferred ranges will keep other aromatic impurities at suitable levels. These advantaged compositions for the initial slurry and for the solid CTA taken directly from the initial slurry are enabled by operating with embodiments of the invention disclosed herein for partial oxidation of para-xylene to TPA.

In a preferred embodiment of the present invention, the weight ratio of time-averaged concentration of PTAL to para-xylene in the liquid component of the initial slurry (i.e., the initial liquid) is at least about 3, 4, 5, or 6. Preferably, the weight ratio of the time-averaged concentration of para-toluic acid PTAC to para-xylene in the initial liquid is at least about 20, 30, 40, or 60. Preferably, the weight ratio of the time-averaged concentration of 4-CBA to para-xylene in the initial liquid is at least about 6, 8, 10, or 12. Preferably, the total concentration of all dissolved aromatic compounds in the liquid phase of any oxidation reaction product slurry (e.g., the initial slurry from primary oxidation and/or the slurry product from any stage of oxidative digestion) and/or any oxidation reaction medium is less than about 16, 10, 6, or 4 weight percent.

Measurement of the concentration of low level components in the solvent, recycled solvent, CTA, initial slurry, and PTA are performed using liquid chromatography methods. Two interchangeable embodiments are now described.

The method referred to herein as HPLC-DAD comprises high pressure liquid chromatography (HPLC) coupled with a diode array detector (DAD) to provide separation and quantitation of various molecular species within a given sample. The instrument used in this measurement is a model 1100

HPLC equipped with a DAD, provided by Agilent Technologies (Palo Alto, Calif.), though other suitable instruments are also commercially available and from other suppliers As is known in the art, both the elution time and the detector response are calibrated using known compounds present in known amounts, compounds and amounts that are appropriate to those occurring in actual unknown samples.

The method referred to herein as HPLC-MS comprises high pressure liquid chromatography (HPLC) coupled with mass spectrometry (MS) to provide separation, identification, and quantitation of various molecular species within a given sample. The instruments used in this measurement is an Alliance HPLC and ZQ MS provided by Waters Corp. (Milford, Mass.), though other suitable instruments are also commercially available and from other suppliers. As is known in the art, both the elution time and the mass spectrometric response are calibrated using known compounds present in known amounts, compounds and amounts that are appropriate to those occurring in actual unknown samples.

FIG. 21 illustrates a conventional process for making purified terephthalic acid (PTA). In the conventional PTA process, para-xylene is partially oxidized in a mechanically agitated high temperature primary oxidation reactor 700. An initial slurry comprising CTA is withdrawn from reactor 700 and then purified in a purification system 702. The PTA product of purification system 702 is introduced into a separation system 706 for separation and drying of the PTA particles. Purification system 702 represents a large portion of the costs associated with producing PTA particles by conventional methods. Purification system 702 generally includes a water addition/exchange system 708, a dissolution system 710, a hydrogenation system 712, and three separate crystallization vessels 704a,b,c. In water addition/exchange system 708, a substantial portion of the mother liquor is displaced with water. After water addition, the water/CTA slurry is introduced into the dissolution system 710 where the water/CTA mixture is heated until the CTA particles fully dissolve in the water. After CTA dissolution, the CTA-in-water solution is subjected to hydrogenation in hydrogenation system 712. The hydrogenated effluent from hydrogenation system 712 is then subjected to three crystallization steps in crystallization vessels 704a,b,c, followed by PTA separation in separation system 706.

FIG. 22 illustrates an improved process for producing PTA employing a primary oxidation reactor 800 configured and operated in accordance with an embodiment of the present invention. An initial slurry comprising solid CTA particles and a liquid mother liquor is withdrawn from reactor 800. Typically, the initial slurry may contain in the range of from about 10 to about 50 weight percent solid CTA particles, with the balance being liquid mother liquor. The solid CTA particles present in the initial slurry typically contain at least about 400 ppmw of 4-carboxybenzaldehyde (4-CBA), more typically at least about 800 ppmw of 4-CBA, and most typically in the range of from 1,000 to 15,000 ppmw of 4-CBA. The initial slurry withdrawn from reactor 800 is introduced into a purification system 802 to reduce the concentration of 4-CBA and other impurities present in the CTA. A purer/purified slurry is produced from purification system 802 and is subjected to separation and drying in a separation system 804 to thereby produce purer solid terephthalic acid particles comprising less than about 400 ppmw of 4-CBA, more preferably less than about 250 ppmw of 4-CBA, and most preferably in the range of from 10 to 200 ppmw of 4-CBA.

Purification system 802 of the PTA production system illustrated in FIG. 22 provides a number of advantages over purification system 802 of the prior art system illustrated in FIG. 21. Preferably, purification system 802 generally includes a liquor exchange system 806, a digester 808, and a single crystallizer 810. In liquor exchange system 806, at least about 50 weight percent of the mother liquor present in the initial slurry is replaced with a fresh replacement solvent to thereby provide a solvent-exchanged slurry comprising CTA particles and the replacement solvent. The solvent-exchanged slurry exiting liquor exchange system 806 is introduced into digester (or oxidative digestion reactor) 808. In digester 808, an oxidative digestion reaction is preformed at slightly higher temperatures than were used in the initial/primary oxidation reaction carried out in bubble column reactor 800. As discussed above, the high surface area, small particle size, and low density of the CTA particles produced in primary oxidation reactor 800 cause certain impurities trapped in the CTA particles to become available for oxidation in digester 808 without requiring complete dissolution of the CTA particles in digester 808. Thus, the temperature in digester 808 can be lower than many similar prior art processes. The oxidative digestion carried out in digester 808 preferably reduces the concentration of 4-CBA in the CTA by at least 200 ppmw, more preferably at least about 400 ppmw, and most preferably in the range of from 600 to 6,000 ppmw. Preferably, the oxidative digestion temperature in digester 808 is at least about 10° C. higher than the primary oxidation temperature in bubble column reactor 800, more preferably about 20 to about 80° C. higher than the primary oxidation temperature in reactor 800, and most preferably 30 to 50° C. higher than the primary oxidation temperature in reactor 800. The oxidative digestion temperature is preferably in the range of from about 160 to about 240° C., more preferably in the range of from about 180 to about 220° C. and most preferably in the range of from 190 to 210° C. The purified product from digester 808 requires only a single crystallization step in crystallizer 810 prior to separation in separation system 804.

CTA particles with the preferred morphology disclosed herein are particularly useful in the above-described oxidative digestion process for reduction of 4-CBA content. In addition, these preferred CTA particles provide advantages in a wide range of other post-processes involving dissolution and/or chemical reaction of the particles. These additional post-processes include, but are not limited too, reaction with at least one hydroxyl-containing compound to form ester compounds, especially the reaction of CTA with methanol to form dimethyl terephthalate and impurity esters; reaction with at least one diol to form ester monomer and/or polymer compounds, especially the reaction of CTA with ethylene glycol to form polyethylene terephthalate (PET); and full or partial dissolution in solvents, including, but not limited too, water, acetic acid, and N-methyl-2-pyrrolidone, which may include further processing, including, but not limited too, reprecipitation of a more pure terephthalic acid and/or selective chemical reduction of carbonyl groups other than carboxylic acid groups. Notably included is the substantial dissolution of CTA in a solvent comprising water coupled with partial hydrogenation that reduces the amount of aldehydes, especially 4-CBA, fluorenones, phenones, and/or anthraquinones.

As mentioned above, the improved purity of the initial slurry produced by the primary oxidation system, previously described, allows the initial slurry to be processed using novel techniques. In particular, FIGS. 23-26 schematically illustrate TPA production systems that employ one or more embodiments of the present invention. Each of the TPA production systems illustrated in FIGS. 23-26 include a primary oxidation stage, at least one oxidative digestion stage, an optional cooling stage, a separation stage, and an optional drying stage. The inventors note that the various step/stages illustrated in FIGS. 23-26 can be substituted for or added into one another. For example, the primary oxidation stage 900 of FIG. 23 can be replaced by the primary oxidation stage 930 of FIG. 25. By way of further example, heating stage 956 of FIG. 26 could be added between the early and later oxidative digestion stages 912 and 914 of FIG. 24.

Figure 23:
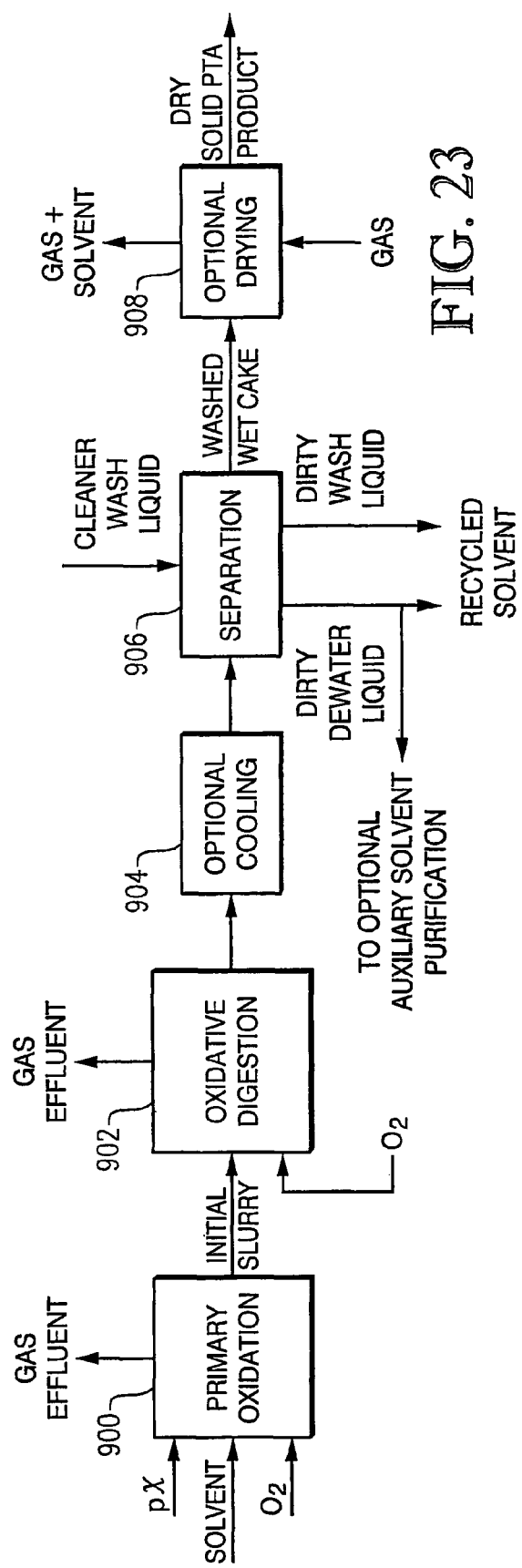
FIG. 23 is a simplified process flow diagram of a process for making PTA in accordance with one embodiment of the present invention, particular illustrating a configuration with reduced and/or eliminated liquor exchange between primary oxidation and oxidative digestion.
Figure 24:
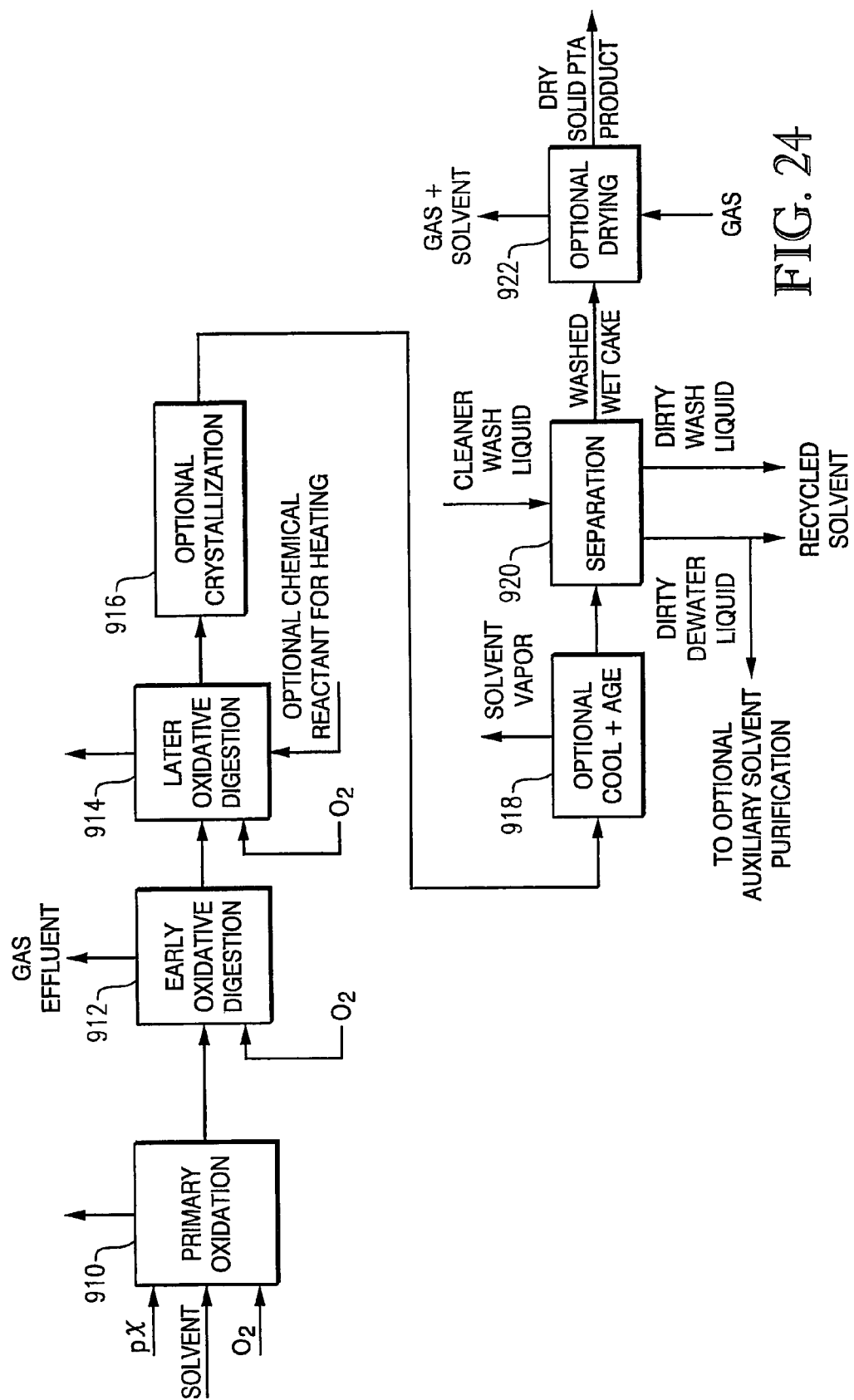
FIG. 24 is a simplified process flow diagram of a process for making PTA in accordance with one embodiment of the present invention, particularly illustrating a configuration employing multi-stage oxidative digestion, heating of the digestion reaction medium via in situ chemical reaction, and evaporative removal of solvent during post-digestion cooling.

In the illustrated embodiments of FIGS. 23 and 24, it is preferred for primary oxidation stages 900 and 910 to be carried out in an oxidation reactor configured and operated in accordance with the description provided above for the oxidation reactor configurations illustrated in FIGS. 1-11. The primary oxidation stage 930 of FIG. 25 preferably employs a reactor that is configured and operated in accordance with the description provided above for the reactor system configurations illustrated in FIGS. 12-14. The primary oxidation stage 950 and sidedraw oxidative digestion stage 952 of FIG. 26 are preferably carried out in a reactor system configured and operated in accordance with the description provided above with reference to FIGS. 15 and 16.

Each of the TPA production systems illustrated in FIGS. 23-26 employ at least one stage of oxidative digestion wherein at least a portion of the initial slurry produced from primary oxidation is subjected to purification by oxidative digestion. As used herein, the term "oxidative digestion" denotes oxidation of a slurry containing a polycarboxylic acid produced via primary oxidation. Preferably, oxidative digestion is carried out under conditions that permit continuous dissolution and reprecipitation of the polycarboxylic acid particles. In one embodiment of the present invention, described in more detail below, oxidative digestion is carried out in a single digestion reactor/zone (e.g., oxidative digestion stage 902 of FIG. 23). In another embodiment of the present invention, described in more detail below, oxidative digestion is carried out in two digestion reactors/zones (e.g., oxidative digestion stages 912 and 914 of FIG. 24, oxidative digestion stages 934 and 938/940 of FIG. 25, and oxidation digestion stages 952 and 954 of FIG. 26). In an alternative embodiment of the present invention, one or more stages of oxidative digestion can be replaced by one or more stages of crystallization (e.g., in FIG. 24, crystallization step 916 could replace later oxidative digestion stage 914). These crystallization stages are preferably carried out in the same manner as the oxidative digestion stages being replaced, except that molecular oxygen is not added to the crystallization stage(s). Typically, the vapor space and gaseous effluent, if any, of the crystallization stage(s) contains less than about 0.001 mole percent molecular oxygen.

In one embodiment of the present invention, it is preferred for at least about 10, 50, 90, or 95 weight percent of the initial solid withdrawn from primary oxidation to be supplied to oxidative digestion within less than about 32, 8, 2, or 0.5 minutes after being withdrawn from primary oxidation. The inventors have discovered that a delay in supplying the initial solid to oxidative digestion increases the amount of 4-CBA retained in solid TPA withdrawn from oxidative digestion. Furthermore, the importance of closely following (i.e., oxidative digestion closely following primary oxidation) becomes greater when the temperature of the initial slurry withdrawn from primary oxidation is greater than about 165° C., 175° C., 185° C., or 190° C.

In the TPA production systems illustrated in FIGS. 23-26 at least a portion of the product (i.e., initial slurry) exiting primary oxidation is subsequently introduced into oxidative digestion without substantial withdrawal of initial liquid and/or without substantial addition of cleaner solvent. Therefore, in one embodiment of the present invention, liquor exchange between primary oxidation and oxidative digestion is substantially eliminated.

The inventors have discovered that when the product of the improved primary oxidation system, described herein, is subsequently processed in accordance with certain embodiments of the present invention, the full or partial removal of catalyst compounds upstream of oxidative digestion is not necessary to control carbon burn during oxidative digestion. As used herein, the term "carbon burn" denotes the formation of carbon monoxide and/or carbon dioxide from an organic compound. Exemplary organic compounds include para-xylene, TPA, reaction intermediates, aromatic impurities, and acetic acid. Furthermore, the inventors have discovered that, even in a continuous process using recycled solvent (defined above), separation of soluble, noxious aromatic impurities away from solid TPA by withdrawal of impurity laden liquor is not necessary to form a solid TPA product suitable for forming PET polymers having high molecular weight, low color, and high overall quality. Quite the contrary, the retention of and eventual precipitation of increased fractions of relatively unreactive aromatic impurities, both colored and uncolored, along with the solid TPA product is surprisingly a preferred mode, given the proper combination of other process steps, as is disclosed in greater detail below.

As used herein, the term "noxious aromatic impurities" denotes colored aromatic impurities and those aromatic compounds containing more or less than two carboxylic acid functions (e.g., BA, PTAC, 4-CBA, TMA, and 2,5,4'-tricarboxybiphenyl). As used herein, the term "relatively unreactive aromatic impurities" denotes aromatic impurities lacking at least one of either a non-aromatic hydrocarbyl group or an oxygen atom covalently bonded to another oxygen atom. As used herein, the term "aromatic impurities" denotes aromatic compounds other than para-xylene and TPA. As used herein, the term "colored aromatic impurities" denotes aromatic impurities not appearing neutrally white to the human eye under typical ambient lighting conditions (e.g., various stilbenes, fluorenones, anthraquinones, and terphenyls). As used herein, the term "aromatic reaction intermediates" denotes aromatic compounds, other than para-xylene, comprising at least one non-aromatic hydrocarbyl group or at least one oxygen atom covalently bonded to another oxygen atom.

When liquor exchange between primary oxidation and oxidative digestion is substantially eliminated in accordance with one embodiment of the present invention, it is preferred for at least about 30, 60, 80, or 95 weight percent of the initial liquid originally present in the initial slurry withdrawn from primary oxidation to be retained in the slurry subjected to oxidative digestion. Thus, it may be preferred for less than about 70, 40, 20, or 5 weight percent of the initial liquid originally present in the initial slurry withdrawn from primary oxidation to be removed from the slurry subjected to oxidative digestion. Preferably, the weight ratio of cobalt, other catalyst compounds, and/or benzoic acid in the slurry entering oxidative digestion to the same compound in the initial slurry produced from primary oxidation is at least about 0.3, 0.6, 0.8, or 0.95. More preferably, the weight ratio of cobalt, other catalyst compounds, and/or benzoic acid in the slurry exiting oxidative digestion to the same compound in the initial slurry produced from primary oxidation is at least about 0.3, 0.6, 0.8, or 0.95. When oxidative digestion is carried out in multiple stages, the description in this paragraph can apply to any or all stages of oxidative digestion, most preferably including the last stage of oxidative digestion.

When liquor exchange between primary oxidation and oxidative digestion is substantially eliminated, it is preferred for the addition of cleaner solvent to the initial slurry to be reduced or eliminated. As used herein, the term "cleaner solvent" denotes solvent having a liquid phase concentration of total catalyst compounds that is less than the concentration of total catalyst compounds in the liquid phase of the slurry to which the cleaner solvent is added. Preferably, the cleaner solvent contains less than about 90, 50, 10, or 2 weight percent of the liquid-phase concentration of total catalyst compounds and/or less than about 90, 50, 10, or 2 weight percent of the liquid-phase concentration of total aromatic compounds compared to the liquid phase of the slurry to which the cleaner solvent is added. Reduced and/or eliminated addition of cleaner solvent minimizes the hydraulic and thermal loads and costs in the overall process for forming the solid TPA product. In addition, reduced and/or eliminated addition of cleaner solvent increases the surprisingly preferred precipitation of sparingly soluble aromatic impurities with the solid TPA in subsequent process steps, as discussed in more detail below.

In a preferred embodiment of the present invention, the mass of cleaner solvent added to the slurry subjected to oxidative digestion is less than about 50, 35, 20, or 10 weight percent of the mass of the initial slurry produced from primary oxidation. Preferably, the ratio of the solids fraction of the slurry entering oxidative digestion to the solids fraction of the initial slurry exiting primary oxidation is at least about 0.5, 0.65, 0.80, or 0.90, based on weight fractions. Preferably, the ratio of the time-averaged concentration of cobalt, other catalyst compounds, and/or benzoic acid in the liquid phase of the slurry subjected to oxidative digestion to the time-averaged concentration of the same compound in the initial liquid of the initial slurry is at least about 0.5, 0.65, 0.80, or 0.90. Preferably, the mass of cleaner solvent added to the slurry subjected to oxidative digestion is less than about 50, 35, 20, or 10 weight percent of the mass of the initial slurry. Preferably, the ratio of the solids fraction of the slurry exiting oxidative digestion to the solids fraction in the initial slurry is at least about 0.5, 0.65, 0.80, or 0.90, based on weight fractions. Preferably, the ratio of the time-averaged concentration of cobalt, other catalyst compounds, and/or benzoic acid in the liquid phase of the slurry exiting oxidative digestion to the time-averaged concentration of the same compound in the initial slurry is at least about 0.5, 0.65, 0.80, or 0.90. When oxidative digestion is carried out in multiple stages, the description in this paragraph can apply to any or all stages of oxidative digestion, most preferably including the last stage of oxidative digestion.

Each of the TPA production systems illustrated in FIGS. 23-26 can optionally employ at least one cooling stage downstream of oxidative digestion (see, cooling stages 904, 918, 942, and 958 in FIG. 23, 24, 25, and 26, respectively). When liquor exchange between primary oxidation and oxidative digestion is substantially eliminated, the slurry produced from oxidative digestion may have a saturated or supersaturated concentration of dissolved aromatic compounds therein. Cooling of a post-digestion slurry having a saturated or supersaturated concentration of dissolved aromatic compounds naturally promotes increased precipitation of sparingly soluble aromatic impurities, both colored and uncolored, with the solid TPA. Thus, a greater fraction of noxious aromatic impurities remain with the solid TPA, and a lesser fraction is sent with the recycled solvent. However, the inventors have discovered that solid TPA product of good color and quality can surprisingly be formed thereby, especially using the purer initial slurry produced in accordance with embodiments of the present invention discussed above. Furthermore, such cooling beneficially reduces the requirements for purification of the recycled solvent using auxiliary process steps, as is discussed in further detail below.

In accordance with one embodiment of the present invention, when a post-digestion cooling stage is employed, it is preferred for liquor exchange between primary oxidation and post-digestion cooling and/or between oxidative digestion and post-digestion cooling to be substantially eliminated. Accordingly, it is preferred for at least about 30, 60, 80, or 95 weight percent of the liquid exiting an oxidation reaction step (e.g., primary oxidation and/or oxidative digestion) to be retained with the slurry produced from the oxidation reaction step until the slurry is cooled by at least about 40° C., 60° C., 80° C., 100° C., or 130° C. below the highest prevailing temperature within the oxidation reaction step. It is preferred for at least about 30, 60, 80, or 95 weight percent of the liquid exiting the oxidation reaction step to be retained with the slurry produced from the oxidation reaction step until the slurry is cooled to a temperature less than about 145° C., 110° C., 80° C., or 55° C. It is preferred for at least about 30, 60, 80, or 95 weight percent of the cobalt, other catalyst compounds, and/or benzoic acid present in the slurry produced from the oxidation reaction step to be retained in the slurry until the slurry is cooled by at least about 40° C., 60° C., 80° C., or 100° C. below the highest prevailing temperature within the oxidation reaction step. It is preferred for at least about 30, 60, 80, or 95 weight percent of the cobalt, other catalyst compounds, and/or benzoic acid present in the slurry produced from the oxidation reaction step to be retained in the slurry until the slurry is cooled to less than about 145° C., 110° C., 80° C., or 55° C. The oxidation reaction step described in this paragraph can be primary oxidation or oxidative digestion. When multi-stage oxidative digestion is employed, the oxidation reaction step described in this paragraph can be primary oxidation or any stage of oxidative digestion, preferably the last stage of oxidative digestion.

In one embodiment of the present invention, it is preferred for the mass of cleaner solvent added to the slurry produced from at least one oxidation reaction step (e.g., primary oxidation and/or oxidative digestion) to be less than about 50, 35, 20, or 10 weight percent of the mass of the slurry produced by the oxidation reaction step prior to cooling the slurry by at least about 40° C., 60° C., 80° C., or 100° C. below the highest prevailing temperature in the oxidation reaction step. It is preferred for the mass of cleaner solvent added to the slurry produced by the oxidation reaction step to be less than about 50, 35, 20, or 10 weight percent of the mass of the slurry produced by the oxidation reaction step prior to cooling the slurry to a temperature less than about 145° C., 110° C., 80° C., or 55° C. It is preferred for at least about 50, 65, 80, or 90 weight percent of the cobalt, other catalyst compounds, and/ or benzoic acid in the slurry produced by the oxidation reaction step to be retained in the slurry until the slurry is cooled by at least about 40° C., 60° C., 80° C., or 100° C. below the highest prevailing temperature within the oxidation reaction step. It is preferred for at least about 50, 65, 80, or 90 weight percent of the cobalt, other catalyst compounds, and/or benzoic acid in the slurry produced by the oxidation reaction step to be retained in the slurry until the slurry is cooled to less than about 145° C., 110° C., 80° C., or 55° C. The oxidation reaction step described in this paragraph can be primary oxidation or any stage of oxidative digestion. In a preferred embodiment, the oxidation reaction step described in this paragraph is primary oxidation.

In accordance with one embodiment of the present invention, it is preferred for at least one stage of oxidative digestion to be carried out at a temperature that is greater than the temperature of the primary oxidation stage and/or the temperature of an early oxidative digestion stage. In such a scenario, it may be necessary to heat the slurry prior to introduction into the digestion reactor/zone or heat the reaction medium in the digestion reactor/zone. The temperature of the reaction medium subjected to oxidative digestion can be increased above the temperature of the prior oxidation reaction step (e.g., primary oxidation and/or an early oxidative digestion stage) by any means known in the art.

In one embodiment of the present invention, the means of increasing the temperature and/or enthalpy of the reaction medium subjected to subsequent oxidative digestion (hereinafter, the "subsequent reaction medium") compared to the reaction medium from a prior oxidation reaction step (hereinafter, the "prior reaction medium") uses the heat of reaction from at least one in situ chemical reaction (i.e., chemical reaction occurring within the subsequent reaction medium). This type of heating configuration is schematically illustrated in the later oxidative digestion stage 914 of FIG. 24. Although FIG. 24 illustrates an embodiment where the chemical reactant is introduced directly into the digestion reactor/zone, the chemical reactant could also be injected upstream of the digestion reactor/zone via addition into the slurry fed to the digestion reactor/zone. The in situ chemical reaction preferably has a heat of reaction that provides at least about 10, 20, 40, or 80 percent of the increase in temperature and/or enthalpy of the subsequent reaction medium compared to the prior reaction medium. The in situ reaction preferably has a heat of reaction sufficient to increase the temperature of subsequent reaction medium by at least about 4° C., 8° C., 12° C., or 16° C. above the temperature of the prior reaction medium. The in situ reaction preferably has a heat of reaction sufficient to increase the enthalpy of the subsequent reaction medium by at least about 2, 4, 6, or 8 kilocalories per kilogram above the enthalpy of the prior reaction medium. In one embodiment of the present invention, the added chemical reactant is acetic anhydride and the in situ heat of reaction from reacting acetic anhydride with water to form acetic acid provides the above-described increase in temperature and/or enthalpy of the subsequent reaction medium. In such an embodiment, it is preferred for the weight of acetic anhydride supplied to the subsequent reaction medium as a percentage of the weight of para-xylene fed to primary oxidation to be in the range of from about 0.1 to about 12, about 0.2 to about 10, about 0.4 to about 8, or 1 to 6 percent.

In an alternative embodiment of the present invention, the means of increasing the temperature of the subsequent reaction medium employs heat of reaction from oxidizing at least one oxidizable compound with molecular oxygen in situ (i.e., within reaction medium of the oxidative digestion stage). Preferably, the in situ oxidized compound comprises a component of solvent, ethanol, acetaldehyde, a xylene, an aromatic reaction intermediate, an aromatic impurity, and/or TPA. When acetaldehyde is employed as the in situ oxidized compound, it is preferred for the weight of acetaldehyde supplied to the subsequent oxidative digestion as a percentage of the weight of para-xylene fed to primary oxidation to be in the range of from about 0.1 to about 12, about 0.2 to about 10, about 0.4 to about 8, or 1 to 6 percent. When ethanol is employed as the in situ oxidized compound, it is preferred for the weight of ethanol supplied to the subsequent oxidative digestion as a percentage of the weight of para-xylene fed to primary oxidation to be in the range of from about 0.1 to about 12, about 0.2 to about 10, about 0.4 to about 8, or 1 to 6 percent. The in situ oxidized compound preferably comprises para-xylene and/or an aromatic reaction intermediate. When para-xylene is employed as the in situ oxidized compound, it is preferred for the weight of para-xylene supplied to the subsequent oxidative digestion as a percentage of the weight of para-xylene supplied to primary oxidation to be in the range of from about 0.1 to about 16, about 0.5 to about 12, about 1 to about 10, or 2 to 8 percent.

In one embodiment of the present invention, the means of increasing the temperature of the subsequent reaction medium uses the heat of reaction from combusting at least one oxidizable compound with molecular oxygen ex situ (i.e., outside the digestion reaction medium) and supplying at least a portion of the heated reaction product therefrom to contact and/or condense into a liquid phase of the digestion reaction medium. Preferably, the heated reaction product of ex situ combustion is supplied to the digestion reactor/zone at multiple locations including at least about 2, 4, 16, or 64 separated openings. Preferably, at least a portion of the heated compound is supplied to the subsequent reaction medium via at least one opening in the lower 50, 30, 10, or 5 percent of the total height of the subsequent reaction medium. Preferably, the heated reaction product has an initial temperature (i.e., prior to being used for heating) of at least about 250° C., 300° C., 400° C., or 500° C. Preferably, the heated reaction product comprises carbon dioxide and/or water, more preferably both. Preferably, the heated reaction product comprises less than about 8, 6, 4, or 2 mole percent molecular oxygen. Preferably, the pressure of the heated reaction product is greater than the pressure of the subsequent oxidative digestion. The ex situ oxidizable compound can comprise a component of solvent, a xylene, an aromatic reaction intermediate, an aromatic impurity, methane, commercial fuel oil, and/or TPA. Preferably, the ex situ oxidizable compound comprises at least one aromatic impurity and at least one of methane or fuel oil.

In an alternative embodiment of the present invention, the means of increasing the temperature of the subsequent reaction medium includes heating at least one compound, not itself a reaction product of an ex situ combustion reaction, to form a heated compound and supplying at least a portion of the heated compound to contact with and/or condense into a liquid phase of the subsequent reaction medium. Preferably, at least a portion of the heated compound is supplied to the subsequent reaction medium at multiple locations via at least about 2, 4, 16, or 64 separated openings. Preferably, at least a portion of the heated compound is supplied to the subsequent reaction medium via at least one opening in the lower 50, 30, 10, or 5 percent of the total height of the subsequent reaction medium. Preferably, at least a portion of the heated compound is supplied to the subsequent reaction medium via at least one opening in the upper 50, 30, 10, or 5 percent of the total height of the subsequent reaction medium. The energy sources for heating the heated compound can include electrical energy and/or thermal energy transferred across a solid surface from a heat transfer fluid (e.g., via an indirect heat exchanger apparatus). Preferably, the heat transfer fluid essentially comprises a heated organic compound or substantially vaporized water. Preferably, at least a portion of the heated organic compound is recirculated and at least a portion thereof is also used to provide thermal energy to a process for forming PET, including but not limited to providing thermal energy to a process stream essentially comprising ethylene glycol. Preferably, the temperature of the heated compound exceeds the temperature prevailing in the oxidative digestion stage by at least about 20° C., 40° C., 60° C., or 80° C. Preferably, the temperature of the heated compound is at least about 200° C., 220° C., 240° C., or 260° C. The heated compound preferably comprises air, a component of solvent, or a slurry comprising solvent, an aromatic reaction intermediate, and solid TPA.

In one embodiment of the present invention, the heated compound comprises slurry containing mass from a prior oxidation reaction step (e.g., primary oxidation and/or early oxidative digestion). This type of configuration is schematically illustrated by the optional heating step 936 in FIG. 25. Preferably, at least about 10, 50, 90, or 95 weight percent of the heated slurry from a prior oxidation reaction step is supplied to subsequent oxidative digestion within less than about 32, 8, 2, or 0.5 minutes of being heated. The inventors have discovered that supplying the heated slurry to oxidative digestion soon after heating provides significant advantages over delayed supply of heated slurry. A delay supplying heated slurry to the digestion reaction medium markedly increases the amount of 4-CBA retained in solid TPA withdrawn from the subsequent digestion reaction medium. Furthermore, the importance of closely following (i.e., oxidative digestion closely following slurry heating) is magnified when the temperature of the heated slurry is above about 170° C., 180° C., 190° C., or 200° C. Without being bound by theory, the inventors suggest that the rate of crystalline rearrangement is accelerated by a preferred temperature increase. A delay in supplying molecular oxygen to form reaction medium may perhaps allow greater incorporation of a portion of 4-CBA in a portion of the rearranged, more perfected crystalline structure of solid TPA, making this portion of 4-CBA more difficult to access during subsequent oxidative digestion.

In one embodiment of the present invention, the heated compound comprises at least one vaporized compound. This type of configuration is schematically illustrated in optional heating step 956 of FIG. 26. The vaporized compound preferably comprises solvent (i.e., acetic acid and water), more preferably a portion of the recycled solvent. Preferably, the vaporized compound is formed from recycled solvent containing less than about 4, 2, 1, or 0.2 weight percent total aromatic compounds and/or less than about 400, 200, 100, or 50 ppmw of all catalyst compounds combined. Preferably, the vaporized solvent comprises either acetic acid with less than about 20, 17, 14, or 11 weight percent water or water with less than about 60, 20, 10, or 2 weight percent acetic acid. Preferably, at least about 20, 40, 60, or 80 weight percent of the water in the vaporized solvent is formed by oxidation of the aromatic compound in primary oxidation. Most preferably, the vaporized solvent comprises a portion of a stream withdrawn from a non-extractive distillation step also being used to form a portion of the recycled solvent. Preferably, at least a portion of the vaporized solvent is commingled with at least a portion of an oxidant stream to form a commingled heated stream before being supplied to oxidative digestion.

In one embodiment of the present invention, an oxidant stream is pressurized from a lesser pressure to a pressure above that of at least one oxidation reaction step (e.g., primary oxidation and/or a stage of oxidative digestion). The oxidant stream preferably has the composition of the oxidant stream described above as being introduced into primary oxidation reactor 20 of FIGS. 1-11. Preferably, the oxidant stream is compressed by a mechanical device such as, for example, a reciprocating-piston-type compressor apparatus, a rotating-screw-type compressor apparatus, and/or a rotating-centrifugal-type compressor apparatus. In a preferred embodiment, the oxidant stream is compressed to a pressure above that of primary oxidation and thereafter supplied to primary oxidation.

In an alternative embodiment, the oxidant stream is compressed to a pressure above that of primary oxidation and above that of at least one stage of oxidative digestion. The compressed oxidant is thereafter split and fed to primary oxidation and at least one stage of oxidative digestion. In such a common-compressor, split-feed configuration, it is preferred for the majority of the oxidant stream to be supplied to primary oxidation, while a minor portion of the oxidant stream is supplied to oxidative digestion. Thus, a single compressor can be used to compress the oxidant streams fed to both primary oxidation and oxidative digestion.

Figure 25:
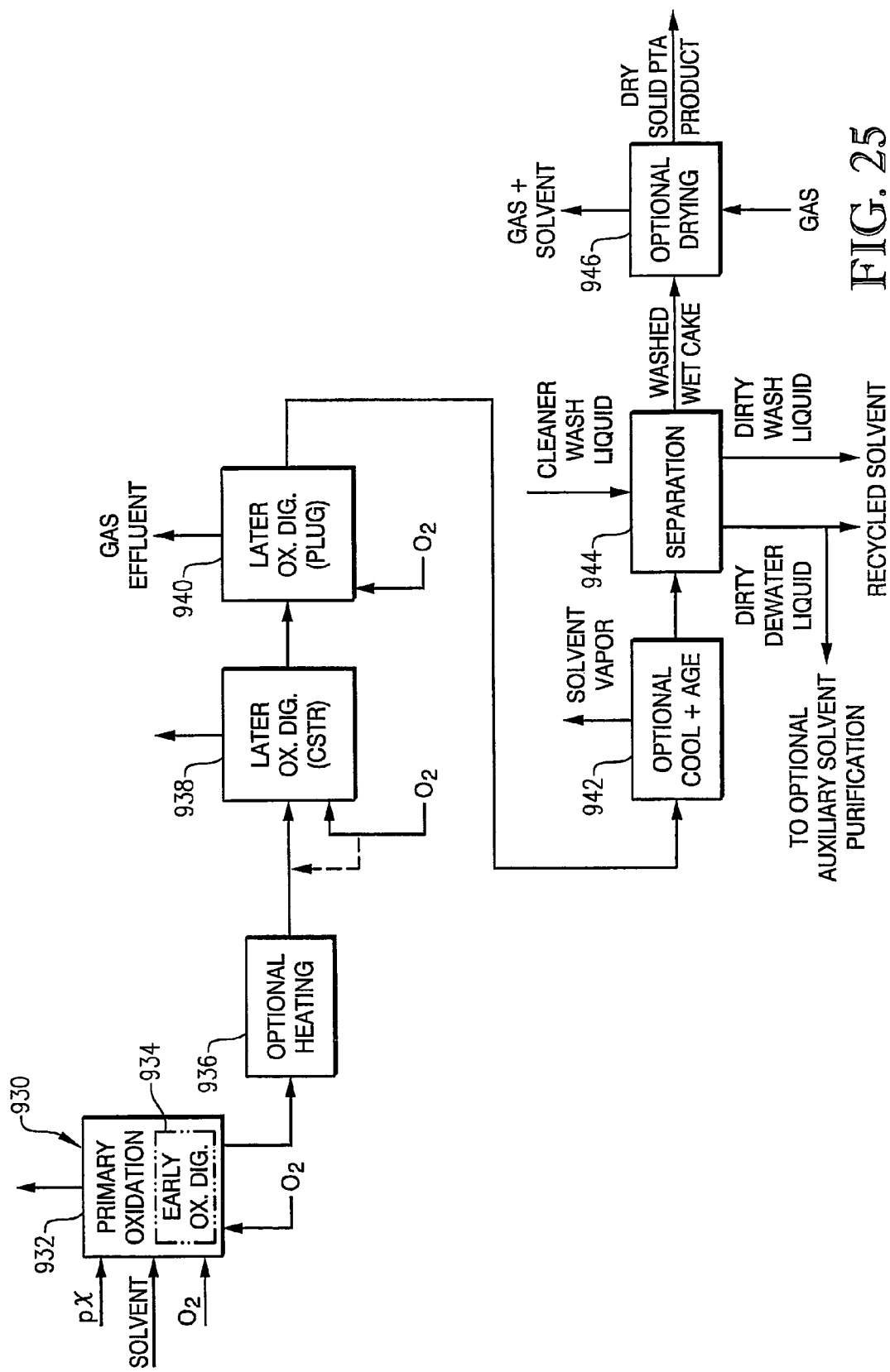
FIG. 25 is a simplified process flow diagram of a process for making PTA in accordance with one embodiment of the present invention, particularly illustrating a configuration employing an early oxidative digestion stage that is internal to the primary oxidation reactor, heating of slurry prior to the later stage of oxidative digestion, and a later oxidative digestion stage having optimized residence time distribution.

In order to carry out oxidative digestion, a secondary oxidant stream comprising molecular oxygen is added either directly into the digestion reactor/zone (FIGS. 23, 24, and 26) or can be added to the feed slurry immediately upstream of the oxidative digestion zone (FIG. 25). Preferably, the mole fraction, measured on a dry basis, of molecular oxygen in the secondary oxidant stream fed to oxidative digestion is in the range of from about 1 mole percent to about 100 mole percent, from about 4 mole percent to about 50 mole percent, from about 10 mole percent to about 30 mole percent, or about the same as atmospheric air. Preferably, the molar ratio of molecular oxygen supplied to primary oxidation to molecular oxygen supplied to oxidative digestion is at least about 2:1, about 4:1 to about 200:1, or 10:1 to 100:1. Preferably, molecular oxygen is supplied to the digestion reactor/zone at multiple locations via at least 2, 4, 16, or 64 separated openings. Preferably, at least about 20, 40, 60, or 80 mole percent of the molecular oxygen supplied to digestion is supplied via at least one opening in the lower 50, 30, 10, or 5 percent of the total height of the digestion reaction medium therein. Preferably, molecular oxygen is supplied by at least one gas distributor conforming to various embodiments disclosed herein for a gas distributor in a primary oxidation bubble column reactor. Preferably, molecular oxygen is supplied to digestion at multiple elevations including at least 2, 3, 4, or 5 separate elevations. In one embodiment, the separated elevations for supplying molecular oxygen to digestion comprise at least one opening in the upper half of the digestion reaction medium and at least one opening in the lower half of the digestion reaction medium.

A predominantly gaseous effluent is withdrawn from oxidative digestion through at least one opening that communicates with a disengaging space provided above the operating level of the reaction medium in the digestion reactor/zone. The predominantly gaseous effluent is preferably withdrawn from the digestion reactor/zone through at least one opening in the upper 50, 30, 10, or 5 percent of the total height of the digestion reactor/zone. When multi-stage oxidative digestion is employed (FIGS. 24-26) it is preferred for the mole fraction, measured on a dry basis, of molecular oxygen in the gaseous effluent withdrawn from an early oxidative digestion stage to be in the range of from about 0.01 to about 8, from about 0.1 to about 5, or from 1 to 3 mole percent, while the mole fraction, measured on a dry basis, of molecular oxygen in the gaseous effluent withdrawn from a later oxidative digestion stage is in the range of from about 0.001 to about 8, from about 0.01 to about 2, or from 0.05 to 0.5 mole percent.

In one embodiment of the present invention, carbon burn losses during oxidative digestion are reduced despite retaining high liquid-phase concentration of catalyst compound in the initial slurry, by using at least two oxidative digestion stages carried out in separate digestion reactors/zones under different conditions. Preferably, oxidative digestion is carried out in a manner such that the moles of total carbon oxides produced in all oxidative digestion stages summed together divided by moles of TPA withdrawn from the stages is in the range of from about 0.0001 to about 0.12, more preferably in the range of from about 0.0005 to about 0.08, still more preferably in the range of from about 0.001 to about 0.06, and most preferably in the range of from 0.006 to 0.04. Preferably, the moles of carbon dioxide produced in all oxidative digestion stages summed together divided by moles of TPA withdrawn from the stages is in the range of from about 0.00008 to about 0.08, more preferably in the range of from about 0.0004:1 to about 0.05, still more preferably in the range of from about 0.0008:1 to about 0.04, and most preferably in the range of from 0.004 to 0.03. Preferably, the moles of carbon monoxide produced in all oxidative digestion stages summed together divided by moles of TPA withdrawn from the stages is in the range of from about 0.00005 to about 0.06, more preferably in the range of from about 0.0002 to about 0.04, still more preferably in the range of from about 0.0005 to about 0.03, and most preferably in the range of from 0.002 to 0.02.

When multi-stage oxidative digestion is employed, it is preferred for the early and later oxidative digestion stages to employ temperatures, pressures, residence times, and/or oxygen amounts that are substantially different from each other. The early stage of oxidative digestion is preferably carried out at a temperature near the temperature of primary oxidation, while the later stage of oxidative digestion is preferably carried out at a temperature greater than the temperature of primary oxidation and the temperature of the early oxidative digestion stage. Preferably, the later stage of oxidative digestion is carried out under "oxygen-starved" conditions, where a very low concentration of molecular oxygen is present in the gaseous effluent.

FIGS. 24-26 schematically illustrate various configurations for multi-stage oxidative digestion. FIG. 24 depicts an early oxidative digestion stage 912 that follows the primary oxidation stage 910, and a later oxidative digestion stage 914 that follows the early oxidative digestion stage 912. FIG. 25 depicts an early oxidative digestion stage 934 that is carried out in a digestion reactor/zone that is contained in the primary oxidation reaction vessel (e.g., as disclosed in FIGS. 12-13 and description relating thereto). In FIG. 25, a later oxidative digestion stage 938 follows an early oxidative digestion stage 934, with an optional heating step 936 located therebetween. FIG. 26 depicts a bubble column early oxidative digestion stage 952 following the primary oxidation stage 950 (e.g., as disclosed in FIGS. 15-16 and description relating thereto). In FIG. 26, a later oxidative digestion stage 954 follows the bubble column early oxidative digestion stage 952, with an optional heating step 956 employed therebetween.

When multi-stage oxidative digestion is employed, it is preferred for at least about 10, 50, 90, or 95 weight percent of the solids withdrawn from the early oxidative digestion stage to be supplied to the later oxidative digestion stage within less than about 32, 8, 2, or 0.5 minutes of being withdrawn. The importance of minimizing the delay between early and later oxidative digestion becomes more important when the temperature of the withdrawn solid is at least about 170° C., 180° C., 190° C., or 200° C.

The temperature of the early oxidative digestion stage relative to the temperature of primary oxidation, measured where the respective slurry predominantly exits primary oxidation and the early oxidative digestion stage, is preferably in the range of from about 10° C. below to about 30° C. above, from about 5° C. below to about 20° C. above, or from about the same as to about 10° C. above. Preferably, the temperature of the later oxidative digestion stage relative to the temperature of primary oxidation, measured where the respective slurry predominantly exits primary oxidation and the later oxidative digestion stage, is in the range of from about 10° C. above to about 100° C. above, from about 15° C. above to about 70° C. above, or from about 20° C. above to about 50° C. above. Preferably, the temperature of the later oxidative digestion stage relative to the temperature of the early oxidative digestion stage, measured where the respective slurry predominantly exits from the early and later oxidative digestion stages, is in the range of from about 5° C. above to about 90° C. above, from about 10° C. above to about 60° C. above, or from about 15° C. above to about 40° C. above. Preferably, the temperature of the early oxidative digestion stage, measured where slurry predominantly exits the early oxidative digestion stage, is in the range of from about 125° C. to about 200° C., from about 140° C. to about 185° C., or from about 150° C. to about 175° C. Preferably, the temperature of the later oxidative digestion stage, measured where slurry predominantly exits from the later oxidative digestion stage, is in the range of from about 150° C. to about 280° C., from about 160° C. to about 240° C., or from 170° C. to about 210° C. When only one oxidation stage is employed, it is preferably operated under the conditions described herein for the later oxidative digestion stage.

When at least two stages of oxidative digestion are employed, it is preferred for the pressure of the early oxidative digestion reaction stage relative to the pressure of primary oxidation, measured where the respective gaseous effluent predominantly exits primary oxidation and the early oxidative digestion stage, to be in the range of from about 0.2 MPa below to about 2 MPa above, from about 0.1 MPa below to about 1 MPa above, or from about the same as to about 0.2 MPa above. Preferably, the pressure of the later oxidative digestion stage relative to the pressure of primary oxidation, measured where the respective gaseous effluent predominantly exits primary oxidation and the early oxidative digestion stage, is in the range of from about the same as to about 8 MPa above, from about 0.5 MPa above to about 4 MPa above, or from about 1 MPa above to about 2 MPa above. Preferably, the pressure of the later oxidative digestion stage relative to the pressure of the early oxidative digestion stage, measured where the respective gaseous effluent predominantly exits from the early and later oxidative digestion stages, is in the range of from about the same as to about 4 MPa above, from about 0.5 MPa above to 3 MPa above, or from about 1 MPa above to about 2 MPa above. Preferably, the pressure of the early oxidative digestion stage, measured where the gaseous effluent predominantly exits the early oxidative digestion stage, is in the range of from about 0.2 MPa to about 3 MPa, from about 0.3 MPa to about 2 MPa, or from about 0.4 MPa to about 1 MPa. Preferably, the pressure of the later oxidative digestion stage, measured where the gaseous effluent predominantly exits the later oxidative digestion stage, is in the range of from about 0.4 MPa to about 8 MPa, from about 0.5 MPa to about 4 MPa, or from 1 MPa to 2 MPa.

In one embodiment of the present invention, it is preferred for the mass-averaged residence time of the slurry phase in the early oxidative digestion stage to be at least about 1, about 2 to about 60, or 5 to 30 minutes. Preferably, the mass-averaged residence time of the slurry phase for an oxidative digestion stage other than the first oxidative digestion stage is in the range of from about 10 to about 480, about 20 to about 360, or 40 to 120 minutes. Preferably, the mass-averaged residence time of the slurry phase for all oxidative digestion stages other than the first oxidative digestion stage sums to a total in the range of from about 10 to about 480, about 20 to about 360, or 40 to 120 minutes.

In one embodiment of the present invention, at least one process step is used for mechanical comminution of the solid TPA prior to oxidative digestion. Preferably, the mechanical comminution reduces the mean particle size of the solid TPA by at least about 5, 10, 20, or 40 percent. Preferably, the mechanical comminution is provided by a centrifugal pump and/or by any other means known in the art.

In one embodiment of the present invention, at least about 2, 3, 4, or 6 oxidative digestion stages are substantially carried out within one pressure containing enclosure (e.g., a vessel or conduit) with mechanical partitions forming compartments having substantial segregation in chemical composition between the reaction medium in adjacent compartments. This type of configuration is schematically illustrated by the later oxidative digestion stage 954 of FIG. 26. The substantial chemical segregation of the compartments creates a condition where the time-averaged solid-phase concentration of 4-CBA of the slurry in at least one compartment is at least about 5, 10, 20, or 30 percent different from the time-averaged solid-phase concentration of 4-CBA of slurry in a directly adjacent compartment. In one embodiment of the invention, the pressure containing enclosure comprises a substantially horizontal cylindrical portion. Preferably, the substantially horizontal cylindrical enclosure portion comprises at least one substantially upright mechanical partition, and the centroids of reaction medium in the adjacent compartments are horizontally displaced from each other by a distance equal to or greater than their vertical displacement. Preferably, the substantially upright mechanical partition presents surfaces that are substantially flat in shape. In another embodiment of the invention, the pressure containing enclosure comprises a substantially upright cylindrical portion. Preferably, the substantially upright cylindrical enclosure portion comprises at least one substantially horizontal mechanical partition, and the centroids of reaction medium in the adjacent compartments are vertically displaced from each other by a distance equal to or greater than their horizontal displacement. Preferably, the substantially horizontal mechanical partition presents surfaces that are substantially flat, ellipsoidal, and/or conical in shape.

Figure 27:
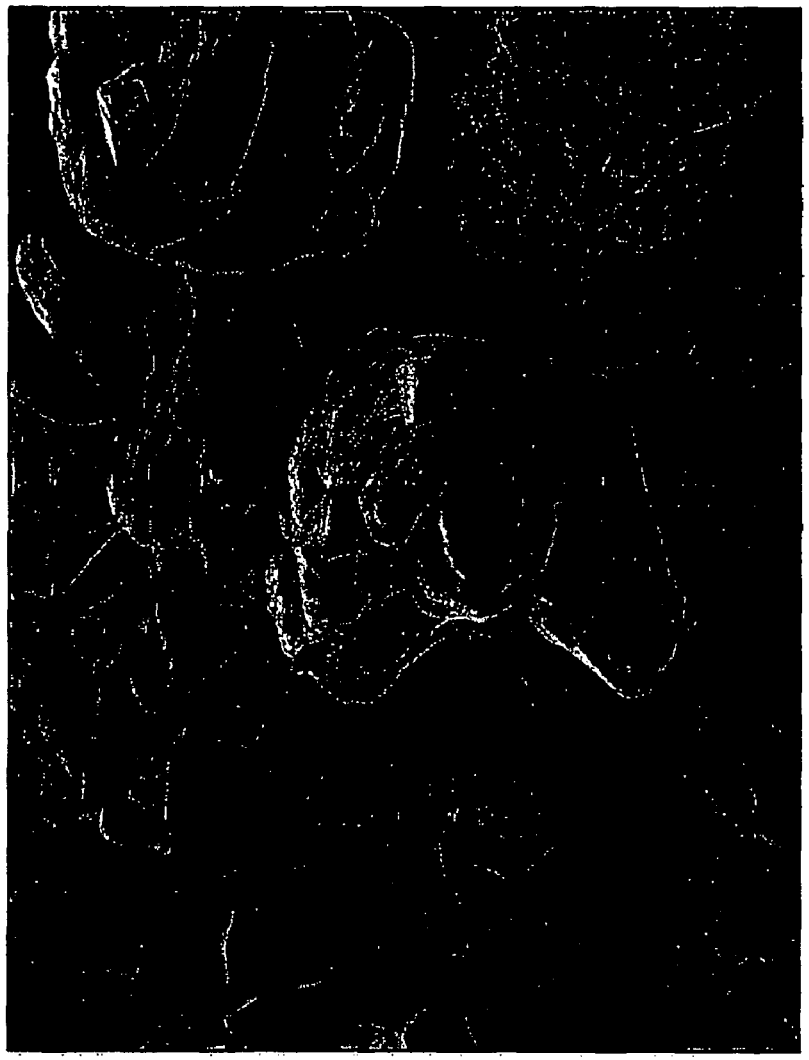
FIG. 27 is a magnified view of TPA particles discharged from a conventional oxidative digester, particularly illustrating that the physical structure of a particle having undesirably low residence time in the digester (e.g., the particle in the bottom right corner) is quite different from the physical structure of properly digested particles.

In accordance with an embodiment of the present invention, oxidative digestion is optimized by controlling the residence time distribution (RTD) of the solid and/or liquid phase of the reaction medium subjected to oxidative digestion. The microphotograph of FIG. 27 illustrates the importance of proper residence time distribution in the digestion reactor/zone. In particular, FIG. 27 shows conventionally-digested TPA particles. The particle in the lower, right corner of the microphotograph is a particle that did not have sufficient residence time in oxidative digestion. Thus, relative to properly digested TPA particles, this particle has more impurities, smaller particle size, higher surface area, less density, and higher dissolvability.

The principles of RTD for mass flow through a chemical reactor and their utility in chemical reactor design and operation are well established. See, for example, Chemical Engineering Kinetics, J. M. Smith, second edition 1970, McGraw-Hill, especially chapter 6, "Deviations from Ideal Reactor Performance." A residence time distribution (RTD) function is defined and described on pages 246 ff therein. A perfectly mixed single tank reactor, often called a continuous flow stirred tank reactor (CSTR) is one idealized case. Another idealized case for flow behavior is plug flow, sometimes called tubular flow or piston flow, where there is negligible convective mixing of mass with surrounding mass while flowing through a reaction zone. Methods for determining experimentally the residence time distribution function for actual, physical reaction zones are defined and described on pages 248 ff of Smith. The methods include introducing step inputs and/or pulse inputs of an inert tracer compound into the flow entering a reaction zone and then measuring the mass of the tracer exiting the reaction zone as a function of time. In recent years, using step and/or pulse inputs of a radioactive tracer material has proven particularly useful, in part because radioactive measurements on exiting flow provide a continuous, non-invasive determination of the mass of tracer exiting as a function of time. Acquisition of such data and reconstruction of the RTD function, including calculation of the mass-averaged residence time, using radioactive tracer methods are available on a commercial, contractual basis from multiple contractors, including for example Tracerco (Houston, Tex.) and Quest TruTec (La Porte, Tex.).

In the following disclosure, a notation is adopted wherein "t" is time; the residence distribution function of time "J(t)" is the cumulative fraction of mass initially supplied to a phase of the reaction zone at time t=0 that then exits the reaction zone before time t; "tavg" is the mass-averaged residence time determined from J(t); "t/tavg" is reduced time meaning time divided by mass-averaged residence time; and "CMF(t/tavg)" is the residence distribution function of reduced time. For example, CMF(0.2) is the cumulative mass fraction initially supplied to a phase of the reaction zone at time t=0 that then exits the reaction zone before a reduced time of 0.2. The mass average residence time (tavg) of an aliquot of mass initially fed to an enclosure at time t=0 is calculated as [(t)*(mass of the aliquot exiting at time t)]/(total mass of the aliquot) integrated from time zero until at least about 99.9 percent of the mass of the aliquot has exited the enclosure. The units of tavg are simply any unit of time.

Figure 28:
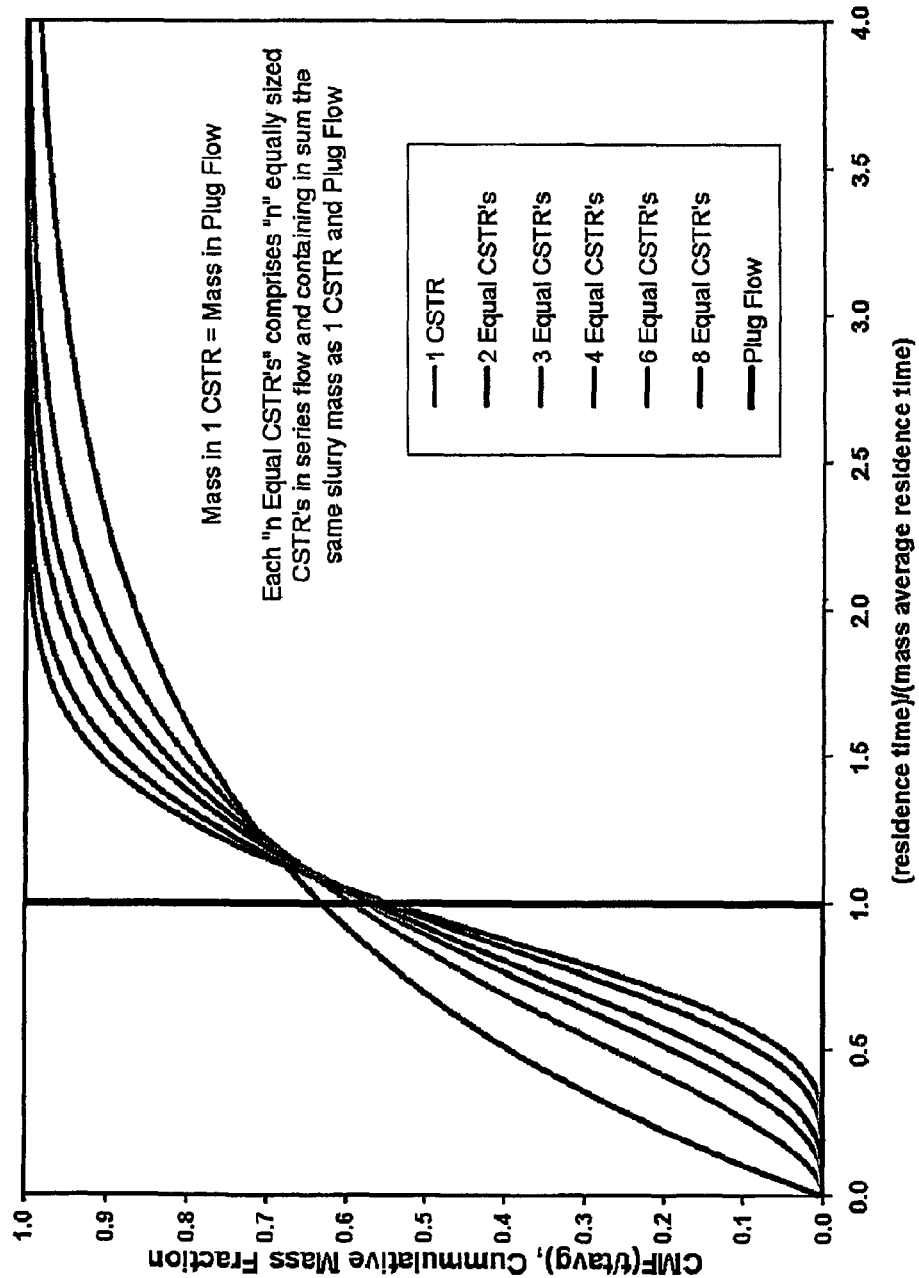
FIG. 28 is a residence time distribution curve plotting cumulative mass fraction (CMF) versus reduced time for a plug flow reactor and for multiple continuous stirred tank reactors (CSTRs) connected in series.

FIG. 28 shows the RTD functions for 1 CSTR, 2 CSTRs, 3 CSTRs, 4 CSTRs, 5 CSTRs, 6 CSTRs, 7 CSTRs, 8 CSTRs, and plug flow. It can be seen that as more CSTRs are employed in series, the RTD approaches idealized plug flow. The inventors have discovered that oxidative digestion is preferably carried out under conditions such that the RTD approaches neither idealized plug flow nor idealized CSTR flow. On the one hand, the mixing and RTD of a CSTR are preferred with respect to a liquid phase so that the liquid-phase concentrations of aromatic reaction intermediates are quickly reduced to low concentrations upon entering oxidative digestion. In particular, this promotes a reduced incorporation of 4-CBA into solid TPA product as the particles rearrange and grow larger and more crystalline in structure, on average. On the other hand, a plug flow behavior is preferred with respect to a solid phase of the reaction medium. With the RTD of a CSTR, many individual particles of solid TPA have relatively short residence in an oxidative digestion reaction step, or series of steps, and these particles tend to retain more of their entering character, which is, on average, undesirably high in solid-phase 4-CBA and undesirably small in particle size.

With this discovery, the inventors can now specify preferred ranges of RTD for at least one oxidative digestion stage and/or a series of oxidative digestion stages that process the initial solid and/or the initial slurry. The inventors note that the liquid, solid, and gas phases can be induced to move through oxidative digestion at different rates by the particular mechanical design of the digestion reactor/zone. In such a case, testing RTD with a solid inert tracer, separately with a liquid inert tracer, and separately with a gaseous inert tracer will give distinct results for J(t) of each phase separately. The disclosures following pertain to a solid phase separately, a liquid phase separately, and/or for a slurry combination thereof.

Figure 29:
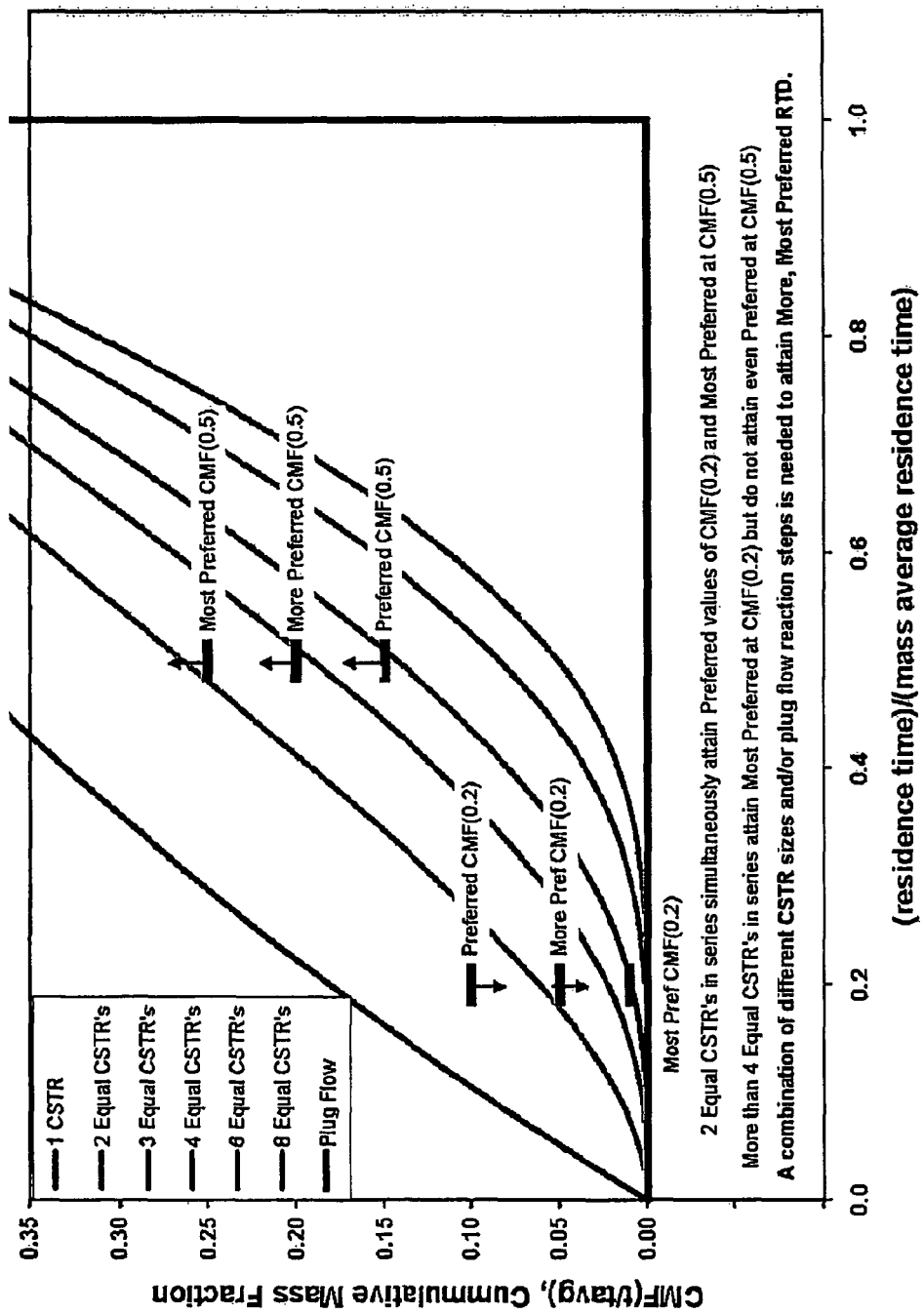
FIG. 29 is an enlarged view of the residence time distribution curve of FIG. 28, better illustrating the portions of the residence time distribution curves at a reduced time value less than 1.0.

Referring now to FIG. 29, in a preferred embodiment of the present invention, at least one oxidative digestion stage and/or a series of oxidative digestion stages process initial solid and/or initial slurry in a manner such that CMF(0.5) is at least about 0.15, 0.20, or 0.25. Further, it is preferred for CMF(0.2) to be less than about 0.10, 0.05, or 0.01. The oxidative digestion stage and/or series of oxidative digestion stages may be carried out in a single fluid enclosure or multiple enclosures with fluidic connection.

To achieve the preferred balance of RTD parameters, a limitless number of mechanical configurations may be employed, of which a few examples follow. One such embodiment is where the mass of reaction medium of all oxidative digestion stages present in a TPA process is split essentially equally into three portions that are situated within three approximately identical pressure containing enclosures. Each comprises mechanical agitation sufficient to be well mixed with respect to liquid-phase and solid compositions therein. Slurry flows through each in sequence from first to last. Each conduit connecting slurry from one of the first two vessels to the next in series comprises slurry mass less than about 0.01, 0.006, 0.003, or 0.001 times the mass of slurry in a single vessel; and the conduits have an elongated ratio of their individual length to their individual maximum diameter of at least about 5:1, 10:1, 20:1, or 40:1. In such a case, CMF(0.2) will equal about 0.04, and CMF(0.5) will equal about 0.19. This provides back-mixing within a preferred range and also provides suppression of short residence times within a more preferred range. Another embodiment is similar to the one preceding wherein the mass of reaction medium in an oxidative digestion stage is split essentially equally into three well-mixed portions. However, the equal portions are situated within a single horizontally-disposed pressure containing enclosure. The equal portions are segregated from each other by upright mechanical partitions and are connected by conduits having little contained mass and little backwards mixing of forward flowing mass, as can be designed using conventional fluid dynamic modeling methods and constructed with conventional fabrication methods. In such a case, CMF(0.2) will again equal about 0.04, and CMF(0.5) will again equal about 0.19. Another embodiment is similar to the two preceding wherein the mass of reaction medium in an oxidative digestion stage is split essentially equally into three well-mixed portions. However, the equal portions are situated within a single upright, cylindrical, pressure-containing enclosure. The equal portions are segregated from each other by horizontal mechanical partitions and are connected by conduits having little contained mass and little backwards mixing of forward flowing mass, as can be designed using conventional fluid dynamic modeling methods and constructed with conventional fabrication methods. In such a case, CMF(0.2) will again equal about 0.04, and CMF(0.5) will again equal about 0.19.

A quite different embodiment of the digestion reactor/zone employs a plug flow digestion reactor/zone in combination with a CSTR zone. Such a configuration is schematically illustrated by the later oxidative digestion stages 938 (CSTR) and 940 (plug) of FIG. 25. In this embodiment, the mass of the reaction medium subjected to oxidative digestion is split to have about 25 percent in an initial digestion reactor/zone designed to approach closely to plug flow, followed by the remaining about 75 percent in a single well-mixed final digestion reactor/zone. In such a case, CMF(0.2) will be essentially nil, and CMF(0.5) will equal about 0.28, providing a desirable balance in RTD as disclosed.

Figure 30:
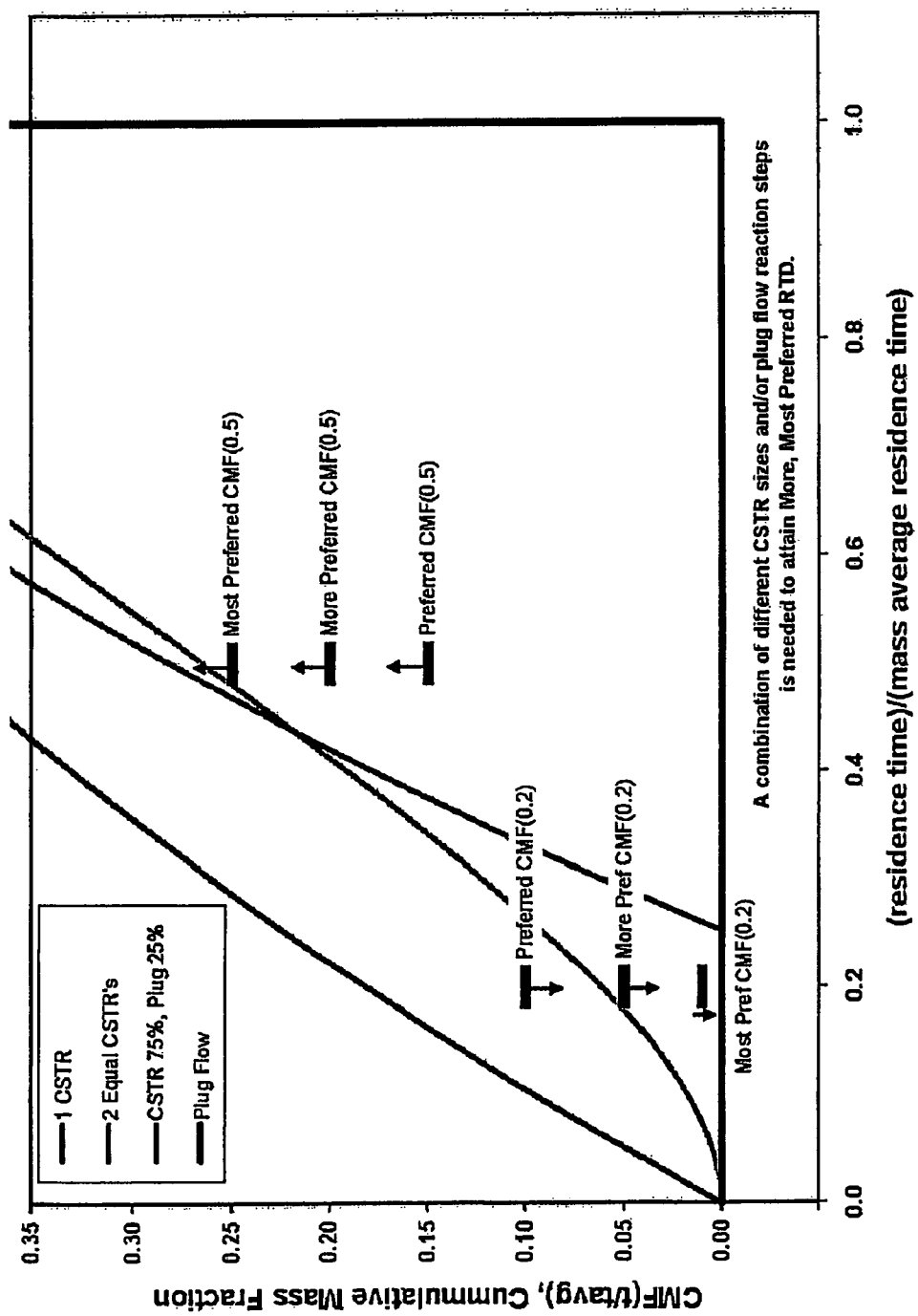
FIG. 30 is an enlarged residence time distribution curve, particularly illustrating the preferred ranges of CMF at reduced times of 0.2 and 0.5 for the an inventive oxidative digestion reactor configuration.

A particularly preferred embodiment of the present invention is similar to the one preceding wherein the mass of the reaction medium subjected to oxidative digestion is split to have about 75 percent in a single well-mixed initial and the remaining about 25 percent in a final digestion reactor/zone designed to approach closely to plug flow; however, the slurry first flows through the well-mixed digestion reactor/zone before entering the plug-flow digestion reactor/zone. FIG. 30 illustrates the RTD function for such a 75 percent CSTR followed by 25 percent plug flow digestion reactor. In such a case, CMF(0.2) will again be essentially nil, and CMF(0.5) will again equal about 0.28, providing a desirable balance in RTD as disclosed. More generally, a particularly preferred embodiment of the present invention comprises: (a) at least one oxidative digestion stage comprising a substantially well-mixed portion of oxidative digestion reaction medium, wherein CMF(0.2) for that stage alone is at least about 0.12; (b) followed by at least one oxidative digestion stage comprising a substantially plug-flow portion of oxidative digestion reaction medium, wherein CMF(0.2) for that stage alone is less than about 0.01; and (c) wherein the disclosed RTD for the combination provides values for CMF(0.2) and CMF(0.5) in the disclosed preferred ranges.

In one embodiment of the present invention, the substantially plug-flow digestion reactor/zone is oriented in a substantially upright manner such that the maximum vertical height of the reaction medium divided by the maximum dimension of the reaction medium measured in any horizontal plane is at least about 3, 5, 7, or 9. Preferably, the prevailing superficial velocity of slurry flowing in the upright plug-flow digestion reactor/zone is less than about 1, 0.3, 0.1, or 0.03 meters per second. In another embodiment of the present invention, the substantially plug-flow digestion reactor/zone is oriented in a substantially horizontal manner such that the maximum horizontal dimension of the reaction medium divided by the maximum dimension of the reaction medium measured in any vertical plane is at least about 3, 5, 7, or 9. Preferably, the prevailing superficial velocity of slurry flowing in the substantially horizontal plug-flow digestion reactor/zone is at least about 0.5, 1, 2, or 3 meters per second. In another embodiment of the present invention, at least two substantially upright plug-flow digestion reactors/zones are connected in series by at least one substantially horizontal plug-flow digestion reactor/zone. In such a configuration, it is preferred for the volume of the connected upright plug flow digestion reactors/zones divided by the volume of the connecting horizontal plug flow digestion reactor/zone to be at least about 50, 100, 200, or 400.

When oxidative digestion employs a substantially well-mixed portion of the digestion reaction medium succeeded by a substantially plug-flow portion of the digestion reaction medium, it is preferred for the mass-averaged residence time of the succeeding plug-flow digestion reaction medium to be in the range of from about 1 to about 60, about 2 to about 40, or 4 to 30 minutes. Preferably, the volume of the substantially well-mixed digestion reactor/zone divided by the volume of the succeeding substantially plug-flow digestion reactor/zone is in the range of from about 1.5 to about 40, about 2 to about 12, about 2.5 to about 10, or 3 to 8.

In a preferred embodiment of the present invention employing multi-stage oxidative digestion, the early oxidative digestion stage substantially reduces the amount of at least one aromatic reaction intermediate compound in the reaction medium. Preferably, the time-averaged concentration of PTAC in the liquid phase of the slurry withdrawn from the early oxidative digestion stage is less than about 50, 10, or 5 percent of the time-averaged concentration of PTAC in the liquid phase of the slurry introduced into the early oxidative digestion stage. Preferably, the time-averaged concentration of PTAC in the liquid phase of the slurry introduced into the early oxidative digestion stage is in the range of from about 50 to about 10,000, about 100 to about 6,000, or 500 to 5,000 ppmw. Preferably, the time-averaged concentration of PTAC in the liquid phase of the slurry withdrawn from the early oxidative digestion stage is less than about 1,000, 200, or 60 ppmw. Preferably, the time-averaged concentration of 4-CBA in the liquid phase of the slurry withdrawn from the early oxidative digestion stage is less than about 50, 10, or 5 percent of the time-averaged concentration of 4-CBA in the liquid phase of the slurry introduced into the early oxidative digestion stage. Preferably, the time-averaged concentration of 4-CBA in the liquid phase of the slurry introduced into the early oxidative digestion stage is in the range of from about 100 to about 6,000, about 200 to about 4,000, or 400 to 3,500 ppmw. Preferably, the time-averaged concentration of 4-CBA in the liquid phase of the slurry withdrawn from the early oxidative digestion stage is less than about 500, 100, or 30 ppmw. Preferably, the time-averaged concentration of 4-CBA in the solid phase of the slurry withdrawn from the early oxidative digestion stage is in the range of from about 5 to about 95, about 10 to about 90, about 20 to about 80, or 30 to 70 percent of the time-averaged concentration of 4-CBA in the solid phase of the slurry introduced into the early oxidative digestion stage. Preferably, the time-averaged concentration of 4-CBA in the solid phase of the slurry introduced into the early oxidative digestion stage is in the range of from about 100 to about 15,000, about 400 to about 8,000, or 1,000 to 6,000 ppmw. Preferably, the time-averaged concentration of 4-CBA in the solid phase of the slurry withdrawn from the early oxidative digestion stage is in the range of from about 100 to about 12,000, about 300 to about 8,000, or 800 to 4,000 ppmw.

In one embodiment of the present invention, it is preferred for the later oxidative digestion stage to substantially reduce the amount of at least one aromatic reaction intermediate compound. Preferably, the time-averaged concentration of PTAC in the liquid phase of the slurry withdrawn from the later oxidative digestion stage is less than about 50, 10, or 2 ppmw. Preferably, the time-averaged concentration of 4-CBA in the liquid phase of the slurry withdrawn from the later oxidative digestion stage is less than about 50, 10, or 2 ppmw. Preferably, the time-averaged concentration of PTAC in the solid TPA product withdrawn from the later oxidative digestion stage is in the range of from about 1 to about 1,000, about 1 to about 500, about 5 to about 125, or 10 to 60 ppmw. Preferably, the time-averaged concentration of 4-CBA in the solid TPA product withdrawn from the later oxidative digestion stage is in the range of from about 1 to about 1,000, about 1 to about 500, about 10 to about 250, or 20 to 125 ppmw. Preferably, the time-averaged concentration of 4,4'-DCS in the solid TPA product is less than about 6, 4, or 2 ppmw.

In one embodiment of the present invention, oxidative digestion is carried out in an agitated reactor defining a reaction zone that contains the digestion reaction medium. Preferably, the maximum height of the digestion reaction medium divided by the maximum diameter of the digestion reaction medium is at least about 1.5, 2, 3, or 4. Preferably, the digestion reactor/zone is equipped with at least one mechanical agitator having impellers located within the digestion reaction medium. Preferably, the mechanical agitator has at least about 2, 3, 4, or 6 different elevations of mechanical agitation impellers located within the digestion reaction medium. Preferably, the mechanical agitator comprises at least two different types of mechanical agitation impellers located within the digestion reaction medium. The mechanical agitator can employ any type of impeller known in the art as particularly apt for gas dispersion, any type of impeller known in the art as particularly apt for fluid pumping, and/or any type of impeller known in the art as particularly apt for suspending solids via fluid pumping. Preferably, at least one impeller particularly apt for suspending solids via fluid pumping is located below at least one impeller particularly apt for gas dispersion. Preferably, at least one impeller particularly apt for suspending solids via fluid pumping is located above the lowest elevation of the digestion reaction medium by less than about 4, 2, 1, or 0.5 times the maximum diameter of the digestion reaction medium. Preferably, at least two of the agitation impellers are separated in elevation by at least about 0.5, 1, 2, or 4 times the maximum diameter of the digestion reaction medium. When the oxidative digestion reactor is compartmentalized, as described above, it is preferred for at least one impeller to be located in each compartment. Preferably, the agitation impellers are located on at least one rotating agitation shaft. Though it may be oriented in any direction, preferably the rotating shaft is upright and passes near or through the centroid of the oxidative digestion reaction medium. Preferably, at least one of the mechanical shafts is supported by at least one mechanical bearing within the digestion reactor/zone.

In a preferred embodiment of the present invention, the rotating agitation shaft is driven by at least one electric motor and optional gear box with mechanical couplings, herein called an "agitator drive." Preferably, the agitator drive is located external to the pressure containing boundary of the digestion reactor/zone. Torque and power are transmitted from the external agitator drive to the rotating agitation shaft via a magnetic or non-magnetic coupling apparatus. Preferably, at least one rotating agitation shaft penetrates (i.e., passes through a pressure-containing boundary of the digestion reactor). At least one of the shaft penetrations can be located below the elevation of the centroid of the digestion reaction medium, more preferable above the elevation of the centroid of the digestion reaction medium, and most preferably near the top of the digestion reactor. In one embodiment, multiple rotating agitation shafts penetrate the pressure containing boundary of the oxidative digestion reactor at multiple elevations separated by at least 0.5, 1, 2, or 4 times the maximum diameter of the digestion reaction medium. Preferably, at least one of the rotating agitation shafts is sealed to a pressure-containing boundary of the digestion reactor using a rotating mechanical seal. The rotating mechanical seal is preferably a double mechanical seal with a seal fluid used for cooling and/or flushing the seal. The seal fluid preferably comprises at least one compound otherwise found within a TPA and/or PET process (e.g., water, acetic acid, xylene, ethylene glycol, and/or diethylene glycol).

In a preferred embodiment of the present invention, at least one opening supplying at least one of an oxidant stream, a slurry, an oxidizable compound, or a heated compound into the digestion reactor/zone is located a distance of less than about $\frac{1}{4}$, $\frac{1}{8}$, $\frac{1}{16}$, or $\frac{1}{32}$ times the maximum diameter of the digestion reaction medium away from a point of closest proximity to a part of a moving mechanical agitator shaft or impeller therein. Preferably, at least one mechanically agitated digestion reactor/zone comprises at least about 1, 2, 4, or 8 elongated structures that are located principally, more preferably entirely, within the reaction medium and are proximate to and more preferably supported by the walls of the digestion reactor. The structure is commonly known as, and herein referred to as, a "wall baffle." An important function of the wall baffle is to influence the mixing within the mechanically agitated reaction medium. Preferably, at least one wall baffle is oriented about normal to the reactor wall to which it is proximate and, more preferably, from which it is supported. The wall baffle is preferably upright and more preferably about vertical. The upright wall baffle is preferably proximate to and supported from an upright wall of the digestion reactor. Preferably, the prevailing distance between the upright wall baffle and the upright wall from which it is supported is in the range of from about 0 to about 0.20, about 0.01 to about 0.17, about 0.02 to about 0.125, or 0.03 to 0.10 times the maximum diameter of the digestion reaction medium. Preferably, the maximum height of the upright wall baffle is in the range of from about 0.1 to about 1.2, about 0.2 to about 1.0, or 0.4 to 0.8 times the maximum height of the digestion reaction medium. Preferably, the maximum width of the upright wall baffle is in the range of from about 0.01 to about 0.25, about 0.02 to about 0.17, about 0.02 to about 0.125, or 0.04 to 0.10 times the maximum diameter of the digestion reaction medium. Preferably, the average thickness of the upright wall baffle is less than about 0.04, 0.02, or 0.01 times the maximum diameter of the digestion reaction medium.

In a preferred embodiment of the present invention, the total power consumed by the mechanical agitation system during steady-state operation of the digestion reactor is in the range of from about 0.05 to about 1.5, about 0.1 to about 0.9, or 0.2 to 0.8 kilowatts per cubic meter of digestion reaction medium (kW/m3). Preferably, the average rotational speed of the impellers during steady-state operation is in the range of from about 20 to about 120 or 30 to about 90 revolutions per minute (rpm).

In an alternative embodiment of the present invention, the digestion reaction medium is agitated by at least one mechanical apparatus having at least one inlet and at least one outlet but no moving part, though process fluid flows through it. Such devices commonly include at least one stationary element encased within a pipe or other flow conduit, and such devices are known in the art by various designations including motionless mixers and static mixers. Preferably, the motionless mixer comprises a multiplicity of stationary elements. Preferably, the motionless mixer comprises at least one element known in the art as particularly apt for gas dispersion or at least one element known in the art as particularly apt for suspending solids. Though it may be oriented in any direction, preferably, the motionless mixer is oriented in an upright direction.

As schematically illustrated in FIG. 26, at least a portion of a gaseous effluent withdrawn from oxidative digestion (e.g., early oxidative digestion stage 952 and later oxidative digestion stage 954) can be processed in at least one optional separation/treatment step 964 to form at least one liquid stream and at least one treated gaseous effluent. Preferably, the separation/treatment step 964 forms at least two liquid streams wherein at least one stream is enriched in water and at least one stream is enriched in an organic compound. The stream enriched in water preferably comprises at least 50 weight percent water and less than 2, 1, 0.7, or 0.5 weight percent acetic acid, on a time-averaged basis. This water-enriched stream is herein called a "removed water stream." The stream enriched in an organic compound preferably comprises at least 50 weight percent acetic acid, more preferably in the range of from about 80 to about 98, 84 to about 95, or 88 to about 92 weight percent acetic acid. More preferably, the separation/treatment step 964 comprises at least one distillation step, still more preferably a non-extractive distillation. The stream enriched in an organic compound can be used to form a portion of the recycled solvent. Preferably, the separation/treatment step 964 also processes at least a portion of the gaseous effluent from primary oxidation.

As shown schematically in FIG. 26, in one embodiment of the present invention, energy is recovered from at least a portion of at least one stream formed in the separation/treatment step 964. Preferably, such energy is recovered from at least a portion of treated gaseous effluent formed in the separation/treatment step 964 by using at least one turbo-expander apparatus. Preferably, at least a portion of the treated gaseous effluent and/or at least a portion of the removed water are treated in a subsequent environmental process step 966 to reduce further the environmental consequences of eventual release back to ambient. The environmental process step 966 can employ catalytic oxidation, regenerative thermal oxidation, treatment in a scrubber, incineration, aerobic biologic wastewater treatment, anaerobic biologic wastewater treatment, reverse osmosis purification of wastewater, adjustment of pH, and/or any other method known in the art.

In a preferred embodiment of the present invention, a slurry is withdrawn from oxidative digestion through at least one opening in the digestion reactor. Preferably, at least about 10, 20, 40, or 99 weight percent of the slurry withdrawn from the digestion reactor is withdrawn via an opening in the lower 50, 30, 10, or 5 percent of the total height of the digestion reaction medium therein. In another embodiment, at least about 10, 20, 40, or 99 weight percent of slurry withdrawn from the digestion reactor is withdrawn via an opening in the upper 50, 30, 10, or 5 percent of the total height of the digestion reaction medium therein.

As illustrated in FIGS. 23-26, the slurry exiting the final stage of oxidative digestion is preferably subject to a cooling step prior to separation of the solid and liquid phases. In a preferred embodiment of the present invention, slurry cooling is provided by an evaporative cooling step, where at least a portion of the liquid phase is caused to evaporate. Such evaporation can be effected by reducing the pressure of the slurry and/or by sparging a gas through slurry. Evaporation of a portion of the liquid cools the remaining liquid, which in turn cools the solid and combined slurry. Evaporated solvent in the effluent gas can be recovered by any means known in the art, including cooling and condensing in a heat exchanger apparatus. One advantage of evaporative cooling over direct liquid cooling is greatly reduced fouling of heat exchange surfaces by precipitating solids. Since the vapor pressure of most aromatic species is quite low after oxidation reaction, these aromatic species do not greatly foul cooling heat exchange surfaces located in a vapor phase.

Where there is a large temperature differential between the inlet and outlet slurries of the slurry cooling step, especially where this is a continuous cooling step using evaporative cooling, the inventors note that the slurry cooling step is preferably executed in smaller sub-steps of temperature change. Such a staged cooling appears to reduce formation of very fine solid particles. For example, it is useful to perform an optimized cooling step using sub-steps wherein the maximum temperature differential between inlet and outlet of at least one sub-step, more preferably all sub-steps, is less than about 80° C., 65° C., 55° C., or 45° C. This becomes increasingly important when the highest temperature prevailing within oxidative digestion is greater than about 175° C., 185° C., 195° C., or 210° C.

In one embodiment of the present invention, specified amounts of the liquid phase of a post-digestion slurry are removed by evaporation. Evaporative removal of a solvent vapor from a liquid phase of the slurry is not to be confused with the withdrawal of the liquid phase as liquid, as described in other embodiments disclosed herein. Owing to the much lesser volatility of many aromatic impurities and catalyst compounds compared to the volatility of water, acetic acid, and other solvent components, evaporative removal of the liquid phase of a post-digestion slurry serves to substantially increase the concentration of aromatic impurities in the slurry. At a given temperature, this promotes increased precipitation of sparingly soluble aromatic impurities, both colored and uncolored, with solid TPA. Although a greater fraction of the highly colored aromatic impurities remain with solid TPA and a lesser fraction are included with the recycled solvent, the inventors have discovered that solid TPA product of good color and quality can surprisingly be formed thereby. Furthermore, such evaporative removal beneficially reduces the requirements for purification of the recycled solvent using auxiliary process steps.

In one embodiment of the present invention, it is preferred for at least about 10, 20, 25, or 30 percent of the mass of the liquid contained in a slurry exiting an oxidation reaction step (e.g., primary oxidation and/or oxidative digestion) to be removed by evaporation prior to substantial dewatering of the slurry. Preferably, the liquid removed by evaporation is removed as part of a post-digestion cooling step. Preferably, the ratio of the time-averaged concentration of cobalt, other catalyst compounds, and/or benzoic acid in the liquid phase of the slurry produced from oxidative digestion to the time-averaged concentration of the same compound in the liquid phase of the initial slurry produced from primary oxidation is at least about 0.9, 1.0, 1.1, or 1.2. Preferably, the ratio of the time-averaged concentration of cobalt, other catalyst compounds, and/or benzoic acid in the liquid phase of the slurry after post-digestion cooling to the time-averaged concentration of the same compound in the liquid phase of the initial slurry produced from oxidative digestion is at least about 0.9, 1.0, 1.1, or 1.2. Preferably the solids fraction of the slurry withdrawn from the evaporative removal step is in the range of from about 10 to about 65 percent, about 20 to about 55 percent, or 30 to 45 percent by weight of the total slurry. Preferably the ratio of the solids fraction of the slurry withdrawn from the evaporative removal step divided by the solids fraction of the slurry fed to the evaporative removal step is at least about 1.05, 1.10, 1.15, or 1.20

The inventors have discovered that it can be advantageous to employ evaporative removal of solvent that contains a high fraction of the initial liquid from primary oxidation, while minimizing and/or eliminating liquor withdrawal and/or addition of cleaner solvent prior to the evaporative removal of solvent. Applied this way, evaporative removal of solvent further increases the fraction of sparingly soluble aromatic impurities in a liquid phase, again diminishing the amount of sparingly soluble aromatic impurities that can be separated away from the solid TPA and making a less pure product. In further distinction, certain embodiments of the present invention form a solid TPA product that, after washing to remove freely soluble catalyst residues, is directly suitable for forming PET polymers having high molecular weight, low color, and high overall quality (i.e., is suitable without further purification processing by methods such as dissolution, hydrogenation, and/or recrystallization).

The inventors have also discovered a preferred range of holding time after post-digestion cooling and before subsequent dewatering of the resulting slurry. Preferably the mass-averaged residence time of a slurry after reaching a post-digestion cooling step temperature, as disclosed herein, is from about 1 to about 480, about 2 to about 120, about 4 to about 60, or 8 to 30 minutes. This holding time is referred to herein as an "aging step." Preferably at least one cooling step is combined with at least one aging step and is referred to herein as a "cooling-and-aging step."

The inventors have discovered that retaining increased fractions of aromatic impurities precipitated with the solid TPA product can surprisingly reduce the formation rate of noxious aromatic impurities when operating continuously with recycled solvent. Thus, one embodiment of the present invention provides a tolerably low total mass of noxious aromatic impurities included with the solid TPA product despite the fact that a greater fraction, and perhaps even greater total mass, of relatively unreactive aromatic impurities end up with solid TPA product. That is, the inventors have discovered that it may be preferable to precipitate more of certain aromatic impurities from solvent while they are in a relatively benign form and before greater amounts thereof are converted to noxious aromatic impurities during subsequent flow via recycled solvent through an oxidation reaction step. For example, cooling the slurry from above 160° C. to below 80° C. greatly diminishes the solubility of IPA and promotes removal of IPA solid with solid TPA product; whereas if IPA is retained in the recycled solvent and returned to an oxidation reaction step, formation of highly colored 2,7-DCF is significantly increased. Similar feedback loops involving recycled solvent exist for IPA and formation of TMA, which is a trifunctional branching monomer in PET polymers; for PA and formation of TMA; for IPA and PA and formation of various other colored fluorenone isomers; for benzoic acid and formation of IPA and PA; and for benzoic acid and formation of various additional colored fluorenone isomers.

Prior art exists for removing the full spectrum of aromatic impurities from recycled solvent, thus reducing the formation rate of noxious aromatic impurities and also the fraction thereof incorporated with solid TPA product. However, prior art is directed toward auxiliary systems for purifying a portion of the recycled solvent. In contrast, various embodiments of the present invention provide more economical methods for eliminating greater fractions of aromatic impurities via the principal process flow of solid TPA rather than in auxiliary systems. In further contrast, various embodiments of the present invention eliminate aromatic impurities in solid TPA product rather than in a waste stream. Notwithstanding elevated concentrations of certain aromatic impurities such as IPA, the solid TPA produced by one or more embodiments of the present invention has low amounts of noxious aromatic impurities and is suitable for forming PET polymers having high molecular weight, low color, and high overall quality.

The inventors note that a linkage exists between embodiments of the present invention and the pre-existing purity of the recycled solvent. If concentrations of relatively unreactive aromatic impurities have accumulated in the recycled solvent, an initial response upon applying inventions herein is quite likely an excessive amount of relatively unreactive aromatic impurities on solid TPA product, rendering it unfit for direct usage in forming PET of high quality. This response will typically last for several days or even weeks while the increased fractions of accumulated relatively unreactive aromatic impurities are de-inventoried from the recycled solvent to exit with solid TPA product. Eventually a new steady state operation is reached, though re-equilibration time will typically vary in duration according to the particular aromatic impurity species being considered. In addition, re-equilibration time depends upon the particular mass inventory of various process steps, upon the impurities present in the commercial-purity para-xylene feed and the stability thereof over time, upon the quality of oxidation reaction steps, and upon the scope of auxiliary systems for purifying recycled solvent. Thus, application of the inventive embodiments described herein in an existing operation using recycled solvent may lead to a very discouraging result persisting over an extended period of time, contributing greatly to making the inventions not obvious. Accordingly, the inventive embodiments disclosed herein are preferred to be maintained for at least one-half of each day of operation of a process for manufacturing the solid TPA product using recycled solvent, more preferably for at least three-quarters of each day for at least about seven consecutive days of operation, and most preferably continuously for a period of at least about 30 consecutive days of operation.

Referring generally to FIGS. 23-26, the slurry withdrawn from the final stage of oxidative digestion can be processed further in one or more of the following additional steps: (1) dewatering the slurry to form an initial wet cake of solid carboxylic acid (e.g., TPA) particles and a removed liquid; (2) washing the initial wet cake with a cleaner solvent to remove catalyst compounds, thereby forming a washed wet cake; (3) dewatering the washed wet cake to form a moist washed cake to remove even more catalyst compounds and solvent; and/or (4) drying the moist washed cake to form a dry solid polycarboxylic acid (e.g., TPA) product. In one embodiment of the present invention, at least a portion of the removed liquid from the slurry dewatering step is fed to an auxiliary process step for removing at least a portion of at least one relatively unreactive aromatic impurity compound (e.g., IPA). As used herein, the term "dewatering" denotes withdrawal of a liquid from a solid by means principally involving the difference in their density and/or their flow properties, rather than their relative volatilities.

In order to separate most solvent, dissolved aromatic impurities, and catalyst compounds from solid TPA, it is preferred to use a slurry dewatering step to process the post-digestion slurry from oxidative digestion and, more preferably, from a cooling and aging step, as disclosed herein. FIGS. 23-26 schematically illustrate slurry dewatering as an initial substep of separation steps 906 (FIG. 23), 920 (FIG. 24), 944 (FIG. 25), and 960 (FIG. 26). Slurry dewatering forms at least one stream enriched in solids essentially comprising solid TPA, called herein "initial wet cake," and at least one stream enriched in liquid essentially comprising solvent, dissolved aromatic impurities, and catalyst compounds, called herein "initial dewatering liquid."

Gravimetric sedimentation, centrifuging and mechanical filtering are preferred dewatering methods, and many suitable mechanical devices are commercially available. These include hydroclones and many types of centrifuges including but not limited to disc pack centrifuges, tubular bowl centrifuges, decanter centrifuges, and screen bowl decanter centrifuges. More preferably, continuously discharging rotating filters are used, especially rotating round drums and/or rotating elongated belts. Both pressure filters and vacuum filters are useful, with pressure filters being more preferred for operating temperatures above about 120° C. Many suitable mechanical devices are commercially available. Most preferably, continuously discharging, rotating, elongated belt filters are used for slurry dewatering, and suitable mechanical devices are commercially available (e.g., Pannevis horizontal belt filters from Larox Corporation, P.O. Box 29, 53101 Lappeenranta, Finland, www.larox.com and BHS horizontal belt filters from BHS-Filtration Inc., 9123-115 Monroe Road, Charlotte, N.C. 28270, www.bhs-filtration.com). Preferably, the mass of liquid in the initial wet cake divided by the mass of solid in the initial wet cake is less than about 0.4, 0.3, or 0.2. Preferably, the mass of cobalt, other catalyst compounds, and/or benzoic acid in the initial wet cake divided by the mass of the same compound in slurry supplied to the dewatering step is less than about 0.4, 0.3, or 0.2.

After forming the initial wet cake, it is preferred to wash the initial wet cake in a final substep of separation with a wash liquid to form a washed wet cake essentially comprising solid TPA. This serves to remove additional catalyst compounds from the initial wet cake while retaining most TPA solids. Preferably, the removal of the catalyst compounds is optimized versus the surprisingly preferred retention of relatively unreactive aromatic impurities, as disclosed herein. A washing step is preferably conducted using another zone integrated within a preferred filter type used for the slurry dewatering step. More preferably, a washing step is conducted using another zone integrated within a continuously discharging, rotating, elongated belt filter. The wash liquid preferably comprises a compound originating from elsewhere in the process for manufacture of TPA and/or PET. Typical examples of such wash liquid compounds include acetic acid, water, methyl acetate, para-xylene, and ethylene glycol. Preferably, the wash liquid comprises acetic acid and water. More preferably, the wash liquid includes a portion of a stream withdrawn from a non-extractive distillation step also being used to form a portion of the recycled solvent. The wash liquid preferably contains less than about 4, 2, 1, or 0.2 weight percent of total aromatic compounds and/or less than about 40, 20, 10, or 5 ppmw of total catalyst compounds. Preferably, the wash liquid comprises at least about 60, 70, 80, or 85 weight percent acetic acid with the balance being water plus trace concentrations of impurities. Preferably, the entering temperature of the wash liquid is less than about 145° C., 110° C., 80° C., or 55° C. The mass flow of wash liquid divided by the mass flow of solid through the washing step is preferably in the range of from about 0.1 to about 4, about 0.2 to about 2, or 0.3 to 1. Preferably, the mass of individual catalyst compounds (e.g. cobalt, manganese, and bromine) remaining in the washed wet cake divided by the mass of the same catalyst compound in slurry fed to the slurry dewatering step is less than about 0.02, 0.01, 0.005, or 0.003. Preferably, the mass of TPA in the washed wet cake divided by the mass of TPA in slurry fed to the slurry dewatering step is at least about 0.96, 0.98, 0.99, or 0.995. Preferably, the mass of at least one relatively unreactive, non-noxious aromatic impurity in the washed wet cake divided by either the mass of the impurity in slurry fed to the slurry dewatering step or by the mass of the impurity in the initial slurry is at least about 0.05, 0.10, 0.20, or 0.30. Preferably, the mass of IPA in the washed wet cake divided by the mass of IPA in slurry fed to the slurry dewatering step or divided by the mass of IPA in initial slurry is at least about 0.05, 0.10, 0.20, or 0.30. Preferably, the mass of 4,4'-DCB in the washed wet cake divided by the mass of 4,4'-DCB in slurry fed to the slurry dewatering step or divided by the mass of 4,4'-DCB in initial slurry is at least about 0.10, 0.20, 0.40, or 0.60. Preferably, the mass of liquid in the washed wet cake divided by the mass of solid in the washed wet cake is less than about 0.4, 0.3, or 0.2. Preferably, the washed wet cake contains less than about 100, 40, 20, or 10 parts per million by weight of total catalyst residues. Preferably, the washed wet cake contains less than about 20, 15, 10, or 5 parts per million by weight of cobalt. Preferably, the washed wet cake contains less than about 20, 15, 10, or 5 parts per million by weight of bromine.

After washing, it is preferred that the mass of liquid in the washed wet cake is reduced by an additional dewatering step to form a moist washed cake essentially comprising solid TPA product. This dewatering step removes additional liquid comprising residual concentrations of catalyst compounds, and it reduces the capital and energy requirements when a subsequent, optional drying operation is used to form a dried solid TPA product. Preferably, the additional dewatering step is conducted using another zone integrated within a preferred filter type used for the slurry dewatering step. More preferably, the additional dewatering step is conducted using another zone integrated within a continuously discharging, rotating, elongated belt filter used for the slurry dewatering and washing steps. Preferably, the mass of liquid in the moist washed cake divided by the mass of solid in the moist washed cake is less than about 0.30, 0.20, 0.15, or 0.07. Preferably, the moist washed cake contains less than about 100, 40, 20, or 10 parts per million by weight of catalyst total residues. Preferably, the moist washed cake contains less than about 20, 15, 10, or 5 parts per million by weight of cobalt. Preferably, the moist washed cake contains less than about 20, 15, 10, or 5 parts per million by weight of bromine.

Optionally, the washed wet cake and/or moist washed wet cake are dried by evaporation of solvent to form a substantially dry solid TPA product containing less than about 0.5, 0.2, 0.1, or 0.05 weight percent of residual volatiles. Such drying step is illustrated in FIG. 23 as optional drying step 908, in FIG. 24 as optional drying step 922, in FIG. 25 as optional drying step 946, and in FIG. 26 as optional drying step 962. The content of volatiles after such drying is conveniently measured by loss of weight upon heating a 100-gram sample of the TPA product spread evenly in a 5-cm diameter sample dish in an oven having ample circulation of air near atmospheric pressure at a temperature 105° C. for a period of 1 hour. Percent volatiles of a sample are calculated as 100*(initial weight−final weight)/(initial weight).

Preferably, the mass of at least one relatively unreactive, non-noxious aromatic impurity in the dry solid TPA product divided by either the mass of the impurity in slurry fed to the slurry dewatering step or by the mass of the impurity in the initial slurry is at least about 0.05, 0.10, 0.20, or 0.30. Preferably, the mass of IPA in the dry solid TPA product divided by the mass of IPA in slurry fed to the slurry dewatering step or divided by the mass of IPA in the initial slurry is at least about 0.05, 0.10, 0.20, or 0.30. Preferably, the mass of 4,4'-DCB in the dry solid TPA product divided by the mass of 4,4'-DCB in the slurry fed to the slurry dewatering step or divided by the mass of 4,4'-DCB in the initial slurry is at least about 0.10, 0.20, 0.40, or 0.60.

Preferably the color of the dry solid TPA product produced by embodiments of the disclosures herein is less than about 3.5, 3.0, 2.5, or 2.0 b* units. The b* value as used herein is one color attribute measured on a spectroscopic instrument such as a Hunter Ultrascan XE instrument (Hunter Associates Laboratory, Inc., 11491 Sunset Hills Road, Reston, Va. 20190-5280, www.hunterlab.com) using a reflectance mode. Positive readings signify the degree of yellow (or absorbance of blue), while negative readings signify the degree of blue (or absorbance of yellow). Preferably, the percent transmittance of solid TPA product produced by embodiments of disclosures herein is at least about 70, 80, 90, or 92 percent at a light wavelength of 340 nm.

Preferably, the solid TPA product formed by one or more of the inventive embodiments disclosed herein essentially comprises particles having a mean particle size, which is D(4,3), of at least about 30 microns, more preferably in the range of from about 35 to about 400 microns, still more preferably in the range of from about 40 to about 200 microns, and most preferably in the range of from 45 to 120 microns. Preferably, the solid TPA product essentially comprises particles having a measured value of D(v,0.1) in the range of from about 5 to about 65 microns, more preferably in the range of from about 10 to about 55 microns, and most preferably in the range of from 15 to 45 microns. Preferably, the solid TPA product essentially comprises particles having a measured value of median particle size, which is D(v,0.5), in the range of from about 25 to about 200 microns, more preferably in the range of from about 30 to about 120 microns, and most preferably in the range of from about 35 to 100 microns. Preferably, the solid TPA product essentially comprises particles having a measured value of D(v,0.9) in the range from about 40 to about 500 microns, more preferably in the range from about 60 to about 300 microns, and most preferably in the range from 80 to 200 microns. Preferably, the solid TPA product essentially comprises particles having a measured value of particle size relative spread in the range from about 0.6 to about 5.0, more preferably in the range from about 0.9 to about 4.0, and most preferably in the range from 1.2 to 2.5. Preferably, the solid TPA product essentially comprises particles having an average BET surface area less than about 0.25 square meters per gram (m2/g), more preferably in the range of from about 0.005 to about 0.2 m2/g, and most preferably in the range of from 0.01 to 0.18 m2/g.

In one embodiment of the present invention, at least a portion of the liquid withdrawn from the slurry dewatering step is supplied as at least a portion of liquid feed to at least one auxiliary step herein called a "recycle solvent purification step." Preferably, the recycle solvent purification step removes at least about 20, 40, 60, or 80 weight percent of at least one relatively unreactive aromatic impurity from the recycled solvent while also recovering at least about 50, 70, 90, or 95 weight percent of the acetic acid and/or at least about 80, 90, 95, or 99 weight percent of the cobalt and/or other valuable catalyst compounds in the liquid feed. A number of such auxiliary steps are disclosed in the prior art. Often, an early step in recycle solvent purification is to heat the liquid feed to evaporate a large fraction of the valuable acetic acid overhead for recovery by cooling and condensation. The aromatic impurities and catalyst compounds are less volatile than acetic acid and these become concentrated in the remaining liquid phase, herein called a sludge. For the sludge, various options have been disclosed for recovering catalyst compounds while recovering or disposing the aromatic impurities. A simple method is to burn the sludge while recovering the ash. Then the cobalt in the ash is redissolved in solvent, for example by using oxalic acid. Another sludge treatment method uses n-propyl acetate and water as extractive agents to separate the cobalt from aromatic impurities. The separated aromatic impurities can be disposed by various methods, including feeding to a subsequent process for recovery of BA, IPA and/or other aromatic species or by environmentally sound waste-water treatment and/or incineration. Yet another sludge treatment method neutralizes the pH, with caustic for example, and then precipitates the cobalt, using sodium carbonate and/or bicarbonate for example, for recovery by filtration. The dissolved aromatic impurities are then disposed by various methods including environmentally sound waste-water treatment and/or incineration. Examples of suitable recycle solvent purification steps include, but are not limited to, those disclosed in U.S. Pat. Nos. 4,356,319 and 4,939,297; U.S. Patent Application Nos. 2005/0038288 and 20050084432; PCT Application Nos. PCT WO98/008605 and WO2005/049873; European Patent Application No. EP121438; and Japanese Patent Application Nos. JP09-157214, JP05-015788, JP54-025292, and JP52-004277.

Although preferably diminished in scope by embodiments disclosed herein, the need for and scope of a recycled solvent purification step depends upon a great many particulars, including but not limited to the impurities in commercial-purity para-xylene and the quality of various oxidation reaction steps. When a recycled solvent purification step is provided, selection of a solvent purification feed can have considerable impact on economies of the step. Relatively unreactive aromatic impurities, both colored and uncolored, are an important target of the step, and relatively greater concentrations thereof reduce the sizing and operating costs for the step. In addition, para-xylene, TPA, and aromatic reaction intermediates are potential yield losses and operating costs when supplied to the step in greater amounts.

It is preferred for the solvent purification feed to comprise at least about 20, 40, 80, or 95 weight percent of its total mass flow from liquid previously processed in primary oxidation and then processed in oxidative digestion. More preferably, the solvent purification feed comprises at least about 20, 40, 80, or 95 weight percent of its total mass flow from liquid previously processed in primary oxidation and then processed in oxidative digestion using reduced and/or eliminated addition of cleaner solvent, described above. Still more preferably, the solvent purification feed comprises at least about 20, 40, 80, or 95 weight percent of its total mass flow from liquid previously processed in primary oxidation, then processed in one oxidative digestion using reduced and/or eliminated addition of cleaner solvent, and then also processed in at least one post-digestion cooling step using reduced and/or eliminated addition of cleaner solvent. Yet still more preferably, the solvent purification feed comprises at least about 20, 40, 80, or 95 weight percent of its total mass flow from liquid processed in primary oxidation, then processed in oxidative digestion using reduced and/or eliminated addition of cleaner solvent, and then also processed in at least one post-digestion cooling-and-aging step using reduced and/or eliminated addition of cleaner solvent. Most preferably, the solvent purification feed comprises at least about 20, 40, 80, or 95 weight percent of its total mass flow from liquid processed in primary oxidation, then processed in oxidative digestion, and then processed in at least one post-digestion cooling-and-aging step employing evaporative removal of solvent vapor, as described above.

Preferably, the solvent purification feed has a TPA concentration, including dissolved TPA and precipitated solid TPA, of less than about 1, 0.5, 0.1, or 0.05 weight percent. Preferably, the solvent purification feed has a concentration of precipitated solids of less than about 1, 0.5, 0.1, or 0.05 weight percent. Preferably, the precipitated solids have a concentration of solid PTAC of less than about 1,000, about 1 to about 600, about 5 to about 400, or 10 to 200 ppmw. Preferably, the precipitated solids have a concentration of solid 4-CBA of less than about 1,200, about 1 to about 800, about 10 to about 600, or 20 to 400 ppmw. Preferably, the solvent purification feed has a concentration of PTAC, including dissolved PTAC and precipitated solid PTAC, of less than about 30, 20, 10, or 2 ppmw. Preferably, the solvent purification feed has a concentration of 4-CBA, including dissolved 4-CBA and precipitated solid 4-CBA, of less than about 50, 30, 10, or 2 ppmw. Preferably, the solvent purification feed in each above disclosure has at least about 20, 40, 80, or 95 weight percent from liquid withdrawn from slurry in a preferred slurry dewatering step, according to all disclosures pertinent thereto. Preferably, the mass of the solvent purification feed is in a range of from about 0 to about 20, about 0.1 to about 15, about 0.5 to about 10, or 1 to 5 percent of the mass of the initial liquid. Preferably, the mass of the solvent purification feed is in a range of from about 0 to about 70, about 0.2 to about 40, about 1 to about 25, or 2 to 15 percent of the mass of the initial solid.

In one embodiment of the present invention, it is preferred for one or more of the operating parameters disclosed herein (including numerically-quantified operating parameters) to be maintained for a commercially-significant period of time. Preferably, operation in accordance with one or more of above-described operating parameters is maintained for at least about 1 hour, more preferably, at least about 12 hours, still more preferably at least about 36 hours, and most preferably at least 96 hours. Thus, unless otherwise indicated herein, the operating parameters described herein are intended to apply to steady-state, optimal/commercial operation—not start-up, shut-down, or sub-optimal operation.

The inventors note that for all numerical ranges provided herein, the upper and lower ends of the ranges can be independent of one another. For example, a numerical range of 10 to 100 means greater than 10 and/or less than 100. Thus, a range of 10 to 100 provides support for a claim limitation of greater than 10 (without the upper bound), a claim limitation of less than 100 (without the lower bound), as well as the full 10 to 100 range (with both upper and lower bounds). Further, when the term "about" is used to modify a numerical value, it should be understood that in one embodiment, the numerical value is the exact numerical value.

The invention has been described in detail with particular reference to preferred embodiments thereof, but will be understood that variations and modification can be effected within the spirit and scope of the invention.

We claim:

1. A process for making a polycarboxylic acid composition, said process comprising:
   (a) feeding an oxidizable aromatic compound to a primary oxidation zone and subjecting a multi-phase reaction medium to oxidation in said a primary oxidation zone under primary oxidation conditions sufficient to produce an initial slurry comprising an initial solid and an initial liquid, wherein said primary oxidation conditions include a primary oxidation temperature in the range of from about 125 to about 200° C., wherein said initial solid comprises a plurality of crude terephthalic acid (CTA) particles in liquid;
   (b) subjecting at least a portion of said initial slurry to oxidative digestion in a first digestion zone under first digestion conditions sufficient to produce a first digestion product slurry, wherein at least about 30 percent of the initial liquid present in the initial slurry withdrawn from the primary oxidation zone is retained in the initial slurry subjected to the first digestion zone and said first digestion conditions include a first digestion temperature that is within 20° C. of said primary oxidation temperature, and
   (c) subjecting at least a portion of said first digestion product slurry to oxidative digestion in a second digestion zone under second digestion conditions sufficient to produce a second digestion product slurry, wherein said second digestion conditions include a second digestion temperature that is greater than both said primary oxidation temperature and said first digestion temperature; wherein the ratio of moles of total carbon oxides produced in the process of steps a), b) and c) to moles of oxidizable aromatic compound fed is in the range of from about 0.02:1 to about 0.25:1 and the time averaged concentration of 4-carboxybenzoic acid in the solid polycarboxylic acid composition withdrawn from the second digestion zone is in the range of from 1 to 500 ppmw.

2. The process of claim 1, wherein said second digestion temperature is in the range of from about 5° C. to about 90° C. above said first digestion temperature.

3. The process of claim 1, wherein said first digestion temperature is in the range of from about 125° C. to about 200° C.

4. The process of claim 3, wherein said second digestion temperature is in the range of from about 10° C. to about 60° C. above said first digestion temperature.

5. The process of claim 4, wherein said first digestion temperature is in the range of from 0° C. to 10° C. above said primary oxidation temperature.

6. The process of claim 5, wherein said first digestion temperature is in the range of from about 140° C. to about 185° C. and said second digestion temperature is in the range of from about 160° C. to about 240° C.

7. The process of claim 1, wherein said primary oxidation, first digestion, and second digestion conditions include respective primary oxidation, first digestion, and second digestion pressures, wherein said first digestion pressure is within about 2 MPa of said primary oxidation pressure, wherein said second oxidation pressure is 0 to about 4 MPa greater than said first digestion pressure.

8. The process of claim 7, wherein said first digestion pressure is in the range of from about 0.2 MPa to about 3 MPa.

9. The process of claim 8, wherein said first digestion pressure is in the range of from about 0.1 MPa below to about 1 MPa above said primary oxidation pressure, wherein said second digestion pressure is in the range of from about 0.5 MPa to about 4 MPa above said first digestion pressure.

10. The process of claim 1, wherein at least about 10 weight percent of the solid phase of said first digestion product slurry is introduced into said second digestion zone within about 32 minutes of being withdrawn from said first digestion zone.

11. The process of claim 1, wherein at least about 90 weight percent of the solid phase of said first digestion product slurry is introduced into said second digestion zone within about 2 minutes of being withdrawn from said first digestion zone.

12. The process of claim 1, further comprising heating at least a portion of said first digestion product slurry, wherein at least about 10 weight percent of said first digestion product slurry subjected to said heating is introduced into said second digestion zone within about 32 minutes of being subjected to said heating.

13. The process of claim 1, further comprising introducing a chemical heating agent into at least a portion of said first digestion product slurry, wherein said chemical heating agent reacts in situ with at least a portion of said initial slurry, wherein at least about 10 percent of a temperature increase between said first and second digestion temperatures is attributable to the heat of reaction of said chemical heating agent with said at least a portion of said first digestion product slurry.

14. The process of claim 13, wherein said chemical heating agent undergoes exothermic in situ oxidation during said oxidative digestion in said second digestion zone.

15. The process of claim 1, wherein the mass-averaged residence time of a slurry phase in said first digestion zone is at least about 1 minute.

16. The process of claim 1, wherein the mass-averaged residence time of a slurry phase in all oxidative digestion zones other than said first digestion zone sums to a total in the range of from about 10 to about 480 minutes.

17. The process of claim 1, wherein the molar ratio of molecular oxygen supplied to said primary oxidation zone to total molecular oxygen supplied to said first and second digestion zones is at least about 2:1.

18. The process of claim 1, wherein the mole fraction, measured on a dry basis, of molecular oxygen in a gaseous effluent withdrawn from said second digestion zone is in the range of from about 0.001 to about 8 mole percent.

19. The process of claim 1, wherein said oxidative digestion is carried out in a manner such that the moles of total carbon oxides produced in said first and second digestion zones summed together divided by moles of terephthalic acid (TPA) withdrawn from said first and second digestion zones is in the range of from about 0.0001 to about 0.12, the moles of carbon monoxide produced in said first and second digestion zones summed together divided by moles of TPA withdrawn from said first and second digestion zones is in the range of from about 0.00005 to about 0.06, and/or the moles of carbon dioxide produced in first and second digestion zones summed together divided by moles of TPA withdrawn from said first and second digestion zones is in the range of from about 0.00008 to about 0.08.

20. The process of claim 1, wherein the time-averaged concentration of para-toluic acid in the liquid phase of a digestion feed slurry introduced into said first digestion zone is in the range of from about 50 to about 10,000 ppmw.

21. The process of claim 1, wherein the time-averaged concentration of para-toluic acid in the liquid phase of said first digestion product slurry is less than about 1,000 ppmw, the time-averaged concentration of 4-carboxybenzaldehyde (4-CBA) in the liquid phase of said first digestion product slurry is less than about 500 ppmw, and/or the time-averaged concentration of 4-CBA in the solid phase of said first digestion product slurry is in the range of from about 100 to about 12,000 ppmw.

22. The process of claim 1, wherein the time-averaged concentration of para-toluic acid in the liquid phase of said second digestion product slurry is less than about 50 ppmw, the time-averaged concentration of 4-CBA in the liquid phase of said second digestion product slurry is less than about 50 ppmw, the time-averaged concentration of para-toluic acid in the solid phase of said second digestion product slurry is in the range of from about 1 to about 1,000 ppmw, and/or the time-averaged concentration of 4-CBA in the solid phase of said second digestion product slurry is in the range of from about 1 to about 1,000 ppmw.

23. The process of claim 1, wherein the time-averaged concentration of para-toluic acid in the liquid phase of said second digestion product slurry is less than about 50 percent by weight of the time-averaged concentration of para-toluic acid in the liquid phase of a first digestion feed introduced into said first digestion zone, wherein the time-averaged concentration of 4-CBA in the liquid phase of said second digestion product slurry is less than about 50 percent by weight of the time-averaged concentration of 4-CBA in the liquid phase of said first digestion feed, and/or wherein the time-averaged concentration of 4-CBA in the solid phase of said second digestion product slurry is less than about 95 percent by weight of the time-averaged concentration of 4-CBA in the solid phase of said first digestion feed.

24. The process of claim 1, wherein less than about 70 weight percent of said initial liquid is removed from said initial slurry prior to introducing said initial slurry into said first digestion zone.

25. The process of claim 1, further comprising, optionally, adding a cleaner liquid to said initial slurry, wherein the amount of said cleaner liquid added to said initial slurry prior to introducing said initial slurry into said digestion zone is less than about 50 percent by weight of said initial slurry.

26. The process of claim 25, wherein the liquid-phase concentration of total catalyst compounds and/or total aromatic compounds in said cleaner liquid is less than about 50 percent, on a weight basis, of the liquid-phase concentration of the same compound or compounds in the liquid phase of said initial slurry.

27. The process of claim 1, wherein the ratio of the time-averaged concentration of cobalt and/or benzoic acid in the liquid phase of a digestion feed slurry entering said first digestion zone to the time-averaged concentration of the same component or components in the liquid phase of said initial liquid exiting said primary oxidation zone is at least about 0.5.

28. The process of claim 1, wherein the weight ratio of the amount of benzoic acid and/or cobalt present in said second digestion product slurry to the amount of the same component or components present in said initial slurry exiting said primary oxidation zone is at least about 0.3.

29. The process of claim 1, further comprising introducing a solvent feed into said primary oxidation zone, wherein at least about 20 weight percent of said solvent feed is recycled solvent.

30. The process of claim 29, wherein at least about 80 weight percent of said solvent feed is recycled solvent.

31. The process of claim 1, wherein said oxidation is maintained for at least one-half of a day of operation in a process for manufacturing terephthalic acid using recycled solvent.

32. The process of claim 1, wherein said polycarboxylic acid comprises terephthalic acid.

33. The process of claim 1, wherein said oxidation of step (a) includes oxidizing para-xylene, wherein said oxidation of step (a) is carried out in a manner such that when said multi-phase reaction medium is theoretically partitioned into 30 horizontal slices of equal volume, a pX-max horizontal slice has the maximum para-xylene concentration of all of said 30 horizontal slices and a pX-min horizontal slice has the minimum para-xylene concentration of all the horizontal slices located above said pX-max horizontal slice, wherein said para-xylene concentration is measured in a liquid phase of said multi-phase reaction medium on a time-averaged and volume-averaged weight basis, wherein the ratio of the para-xylene concentration of said pX-max horizontal slice to the para-xylene concentration of said pX-min horizontal slice is at least about 5:1.

34. The process of claim 1, wherein said primary oxidation zone is defined within a bubble column reactor.

35. The process of claim 34, wherein at least one of said first and second digestion zones is defined within a continuous stirred tank reactor.

36. The process of claim 1, further comprising dewatering, washing, and drying at least a portion of said second digestion product slurry to thereby produce a dry solid TPA product, wherein said dry solid TPA product has a b* of less than about 3.5 units, a percent transmittance of at least about 70 percent at a light wavelength of 340 nm, a mean particle size of at least about 30 microns, a median particle size in the range of from about 25 to about 200 microns, a D(v,0.1) in the range of from about 5 to about 65 microns, a D(v,0.9) in the range from about 40 to about 500 microns, and a relative spread in the range from about 0.6 to about 5.0.

* * * * *